United States Patent
Hatakeyama et al.

(10) Patent No.: US 9,523,914 B2
(45) Date of Patent: Dec. 20, 2016

(54) CHEMICALLY AMPLIFIED RESIST COMPOSITION AND PATTERNING PROCESS

(71) Applicant: SHIN-ETSU CHEMICAL CO., LTD., Tokyo (JP)

(72) Inventors: Jun Hatakeyama, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/943,248

(22) Filed: Nov. 17, 2015

(65) Prior Publication Data

US 2016/0147150 A1 May 26, 2016

(30) Foreign Application Priority Data

Nov. 25, 2014 (JP) ................. 2014-237527

(51) Int. Cl.
| | |
|---|---|
| G03F 7/004 | (2006.01) |
| C07J 9/00 | (2006.01) |
| G03F 7/038 | (2006.01) |
| C07D 233/60 | (2006.01) |
| G03F 7/20 | (2006.01) |
| G03F 7/40 | (2006.01) |
| C07J 41/00 | (2006.01) |

(52) U.S. Cl.
CPC ........... *G03F 7/0382* (2013.01); *C07D 233/60* (2013.01); *C07J 9/005* (2013.01); *C07J 41/00* (2013.01); *G03F 7/2004* (2013.01); *G03F 7/40* (2013.01)

(58) Field of Classification Search
CPC .......... G03F 7/038; G03F 7/2004; G03F 7/26; G03F 7/40; C07D 233/60; C07J 9/005; C07J 41/00
USPC .... 430/270.1, 322, 325, 329, 330, 331, 919; 552/549, 553, 554
See application file for complete search history.

(56) References Cited

U.S. PATENT DOCUMENTS

| | | | |
|---|---|---|---|
| 6,258,508 B1 * | 7/2001 | Kim | C08F 32/08 430/270.1 |
| 6,673,511 B1 | 1/2004 | Hatakeyama et al. | |
| 6,749,988 B2 | 6/2004 | Hatakeyama et al. | |
| 6,916,593 B2 | 7/2005 | Hatakeyama et al. | |
| 7,629,108 B2 | 12/2009 | Watanabe et al. | |
| 2003/0008276 A1 | 1/2003 | Tchilian et al. | |
| 2006/0136414 A1 | 6/2006 | Roach et al. | |
| 2015/0004544 A1 | 1/2015 | Namai | |
| 2016/0147149 A1 * | 5/2016 | Hatakeyama | G03F 7/039 430/270.1 |

FOREIGN PATENT DOCUMENTS

| | | |
|---|---|---|
| JP | 08015865 A * | 1/1996 |
| JP | 2001-194776 A | 7/2001 |
| JP | 2002-226470 A | 8/2002 |
| JP | 2002-363148 A | 12/2002 |
| JP | 2004-191764 A | 7/2004 |
| JP | 3790649 B2 | 6/2006 |
| JP | 2008-107513 A | 5/2008 |
| WO | 2013/137157 A1 | 9/2013 |

OTHER PUBLICATIONS

Machine translation of JP 08-015865 (no date).*
Sreekanth et al, "Design, Synthesis, and Mechanistic Investigations of Bile Acid-Tamoxifen Conjugates for Breast Cancer Therapy", Bioconjugate Chemistry, 24(9), 1468-1484 (2013).*

* cited by examiner

*Primary Examiner* — Amanda C Walke
(74) *Attorney, Agent, or Firm* — Westerman, Hattori, Daniels & Adrian, LLP

(57) ABSTRACT

A chemically amplified resist composition comprising a base polymer, an acid generator, and a basic compound which is a cholanoate having an acid labile group-protected amino group has a high contrast of alkaline dissolution rate before and after exposure and high resolution and forms a pattern of satisfactory profile with minimal roughness.

9 Claims, No Drawings

CHEMICALLY AMPLIFIED RESIST COMPOSITION AND PATTERNING PROCESS

CROSS-REFERENCE TO RELATED APPLICATION

This non-provisional application claims priority under 35 U.S.C. §119(a) on Patent Application No. 2014-237527 filed in Japan on Nov. 25, 2014, the entire contents of which are hereby incorporated by reference.

TECHNICAL FIELD

This invention relates to a chemically amplified resist composition comprising a specific basic compound, and a patterning process using the same.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

With respect to high-energy radiation of very short wavelength such as EB or x-ray, hydrocarbons and similar light elements used in resist materials have little absorption. Then polyhydroxystyrene base resist materials are under consideration.

Resist materials for EB lithography are practically used in the mask image writing application. Recently, the mask manufacturing technology becomes of greater interest. Reduction projection exposure systems or steppers have been used since the time when the exposure light was g-line. While their demagnification factor was ⅕, a factor of ¼ is now used as a result of chip size enlargement and projection lens diameter increase. It becomes of concern that a dimensional error of a mask has an impact on the dimensional variation of a pattern on wafer. It is pointed out that as the pattern feature is reduced, the value of a dimensional variation on the wafer becomes greater than the value of a dimensional error of the mask. This is evaluated by a mask error enhancement factor (MEEF) which is a dimensional variation on wafer divided by a dimensional error of mask. Patterns on the order of 45 nm often show an MEEF in excess of 4. In a situation including a demagnification factor of ¼ and a MEEF of 4, the mask manufacture needs an accuracy substantially equivalent to that for equi-magnification masks.

The exposure system for mask manufacturing made a transition from the laser beam exposure system to the EB exposure system to increase the accuracy of line width. Since a further size reduction becomes possible by increasing the accelerating voltage of the electron gun in the EB exposure system, the accelerating voltage has increased from 10 keV to 30 keV and reached 50 keV in the current mainstream system, with a voltage of 100 keV being under investigation.

Chemically amplified resist compositions comprising an acid generator capable of generating an acid upon exposure to light or EB include chemically amplified positive resist compositions wherein deprotection reaction takes place under the action of acid and chemically amplified negative resist compositions wherein crosslinking reaction takes place under the action of acid. Quenchers are often added to these resist compositions for the purpose of controlling the diffusion of the acid to unexposed areas to improve the contrast. The addition of quenchers is fully effective to this purpose. A number of amine quenchers were proposed as disclosed in Patent Documents 1 to 3.

Patent Documents 4 to 6 propose quenchers in the form of a protected amine compound having an amino group substituted with an acid labile group and adapted to generate a basic compound under the action of acid. Since acid generators such as alkyl sulfonium salts, iodonium salts, and imidosulfonates and polymers having a specific lactone or acid anhydride as adhesive group are readily decomposed with a strong base, protected amine compounds are used in such situation.

Acid diffusion may be suppressed by adding an amine quencher having a high molecular weight. A polymer having an amine quencher bound thereto is an amine quencher having the highest molecular weight, but has the problem that a slight change of copolymerization ratio invites a change of sensitivity of a resist material. A resist material to which a cholic acid ester having an amino group is added is successful in suppressing acid diffusion a degree, as described in Patent Document 7. However, since the cholic acid ester having an amino group is a strong base, the type of the acid generator and the base polymer's adhesive group which can be combined therewith is limited. There is a need to have a protected amine compound of giant molecule which is effective for suppressing acid diffusion and imposes few or no limits on the acid generator and base polymer's adhesive group.

CITATION LIST

Patent Document 1: JP-A 2001-194776
Patent Document 2: JP-A 2002-226470
Patent Document 3: JP-A 2002-363148
Patent Document 4: JP 3790649
Patent Document 5: JP-A 2004-191764
Patent Document 6: WO 2013/137157
Patent Document 7: JP-A 2008-107513

DISCLOSURE OF INVENTION

An object of the invention is to provide chemically amplified positive and negative resist compositions which surpass prior art resist compositions in acid diffusion control and are improved in edge roughness (LWR); and a pattern forming process using the same.

In search for the currently desired resist material having a high resolution, the inventors have found that a chemically amplified positive or negative resist composition comprising a cholanoate having an acid labile group-protected amino group as amine quencher has the advantages of controlled acid diffusion and minimal edge roughness.

Accordingly, the chemically amplified positive or negative resist composition of the invention forms a pattern with minimal edge roughness. Owing to this and other advantages, the composition is readily applicable in the industry and very useful as the VLSI-forming resist material and mask pattern-forming material.

In one aspect, the invention provides a chemically amplified resist composition comprising a base polymer, an acid generator, and a basic compound having the general formula (1)-1 and/or (1)-2.

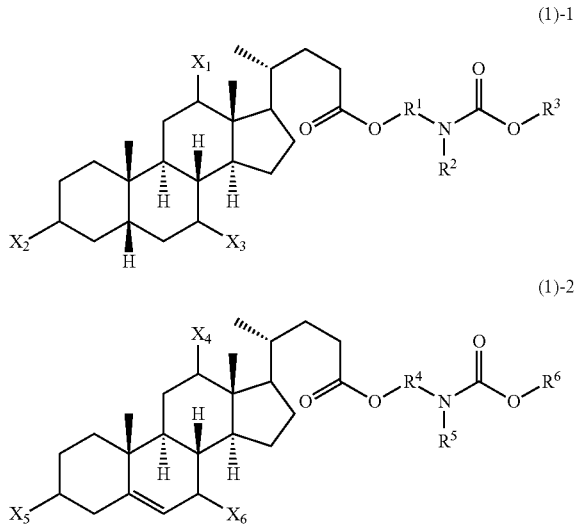

Herein $R^1$ and $R^4$ each are a single bond, a straight, branched or cyclic $C_1$-$C_{20}$ alkylene, $C_6$-$C_{10}$ arylene, $C_2$-$C_{20}$ alkenylene, or $C_2$-$C_{20}$ alkynylene group, $R^2$ and $R^5$ each are hydrogen or a straight, branched or cyclic $C_1$-$C_{12}$ alkyl group, or $R^2$ may bond with $R^1$ to form a ring, and $R^5$ may bond with $R^4$ to form a ring, $R^3$ and $R^6$ each are an acid labile group, $X_1$ to $X_6$ each are hydrogen, hydroxyl, alkoxy, acyloxy or carbonyl group.

The resist composition may further comprise an organic solvent, the composition being a chemically amplified positive resist composition. The positive resist composition may further comprise a dissolution inhibitor.

The resist composition may further comprise an organic solvent, the composition being a chemically amplified negative resist composition. The negative resist composition may further comprise a crosslinker.

In either embodiment, the resist composition may further comprise a surfactant.

In another aspect, the invention provides a process for forming a pattern comprising the steps of applying the resist composition defined above onto a substrate, baking to form a resist film, exposing the resist film to high-energy radiation, and developing the exposed film with a developer.

Typically, the high-energy radiation is ArF excimer laser radiation of wavelength 193 nm, KrF excimer laser radiation of wavelength 248 nm, EB or EUV of wavelength 3 to 15 nm.

The chemically amplified positive or negative resist compositions are used not only in the lithography for semiconductor circuit formation, but also in the formation of mask circuit patterns, micro-machines, and thin-film magnetic head circuits.

Advantageous Effects of Invention

The resist compositions have many advantages including a fully high contrast of alkaline dissolution rate before and after exposure, a high resolution, a good pattern profile after exposure, and minimal roughness. There are provided positive or negative resist compositions, especially chemically amplified positive or negative resist compositions which are very useful as the fine pattern-forming resist material for the fabrication of VLSI and photomasks, and the pattern-forming resist material in the KrF excimer laser, ArF excimer laser, EB and EUV lithography.

DESCRIPTION OF EMBODIMENTS

As used herein, the singular forms "a," "an" and "the" include plural referents unless the context clearly dictates otherwise. "Optional" or "optionally" means that the subsequently described event or circumstances may or may not occur, and that description includes instances where the event or circumstance occurs and instances where it does not. The notation ($C_n$-$C_m$) means a group containing from n to m carbon atoms per group.

The abbreviations and acronyms have the following meaning.
  Mw: weight average molecular weight
  Mn: number average molecular weight
  Mw/Mn: molecular weight distribution or dispersity
  GPC: gel permeation chromatography
  PEB: post-exposure bake
  PAG: photoacid generator
  EB: electron beam
  EUV: extreme ultraviolet
  LWR: line width roughness
  CDU: critical dimension uniformity Briefly stated, the invention provides a chemically amplified resist composition comprising a base polymer, an acid generator, and a basic compound. The basic compound used herein is a cholanoate having an acid labile group-protected amino group, represented by the general formula (1)-1 or (1)-2.

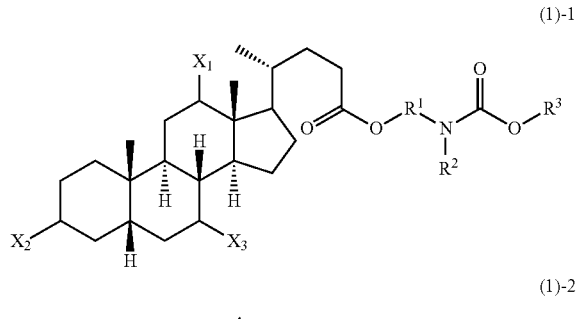

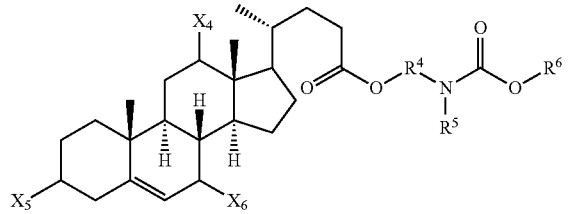

Herein $R^1$ and $R^4$ each are a single bond, a straight, branched or cyclic $C_1$-$C_{20}$ alkylene, $C_6$-$C_{10}$ arylene, $C_2$-$C_{20}$ alkenylene, or $C_2$-$C_{20}$ alkynylene group, $R^2$ and $R^5$ each are hydrogen or a straight, branched or cyclic $C_1$-$C_{12}$ alkyl group, or $R^2$ may bond with $R^1$ to form a ring, and $R^5$ may bond with $R^4$ to form a ring, $R^3$ and $R^6$ each are an acid labile group, $X_1$ to $X_6$ each are hydrogen, hydroxyl, alkoxy, acyloxy or carbonyl group.

Examples of the cholanoate having an acid labile group-protected amino group, represented by formula (1)-1 or (1)-2 are shown below, but not limited thereto.

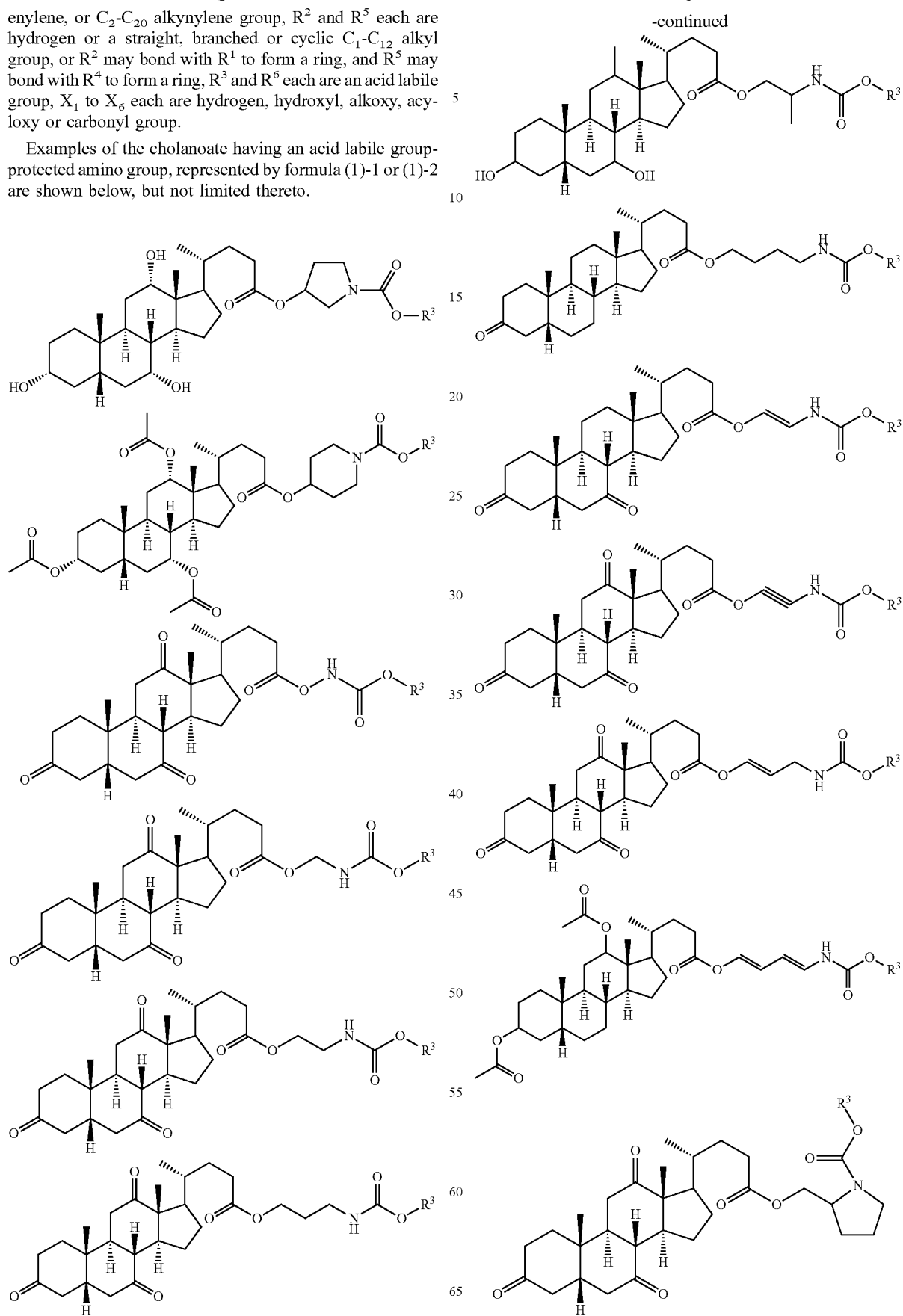

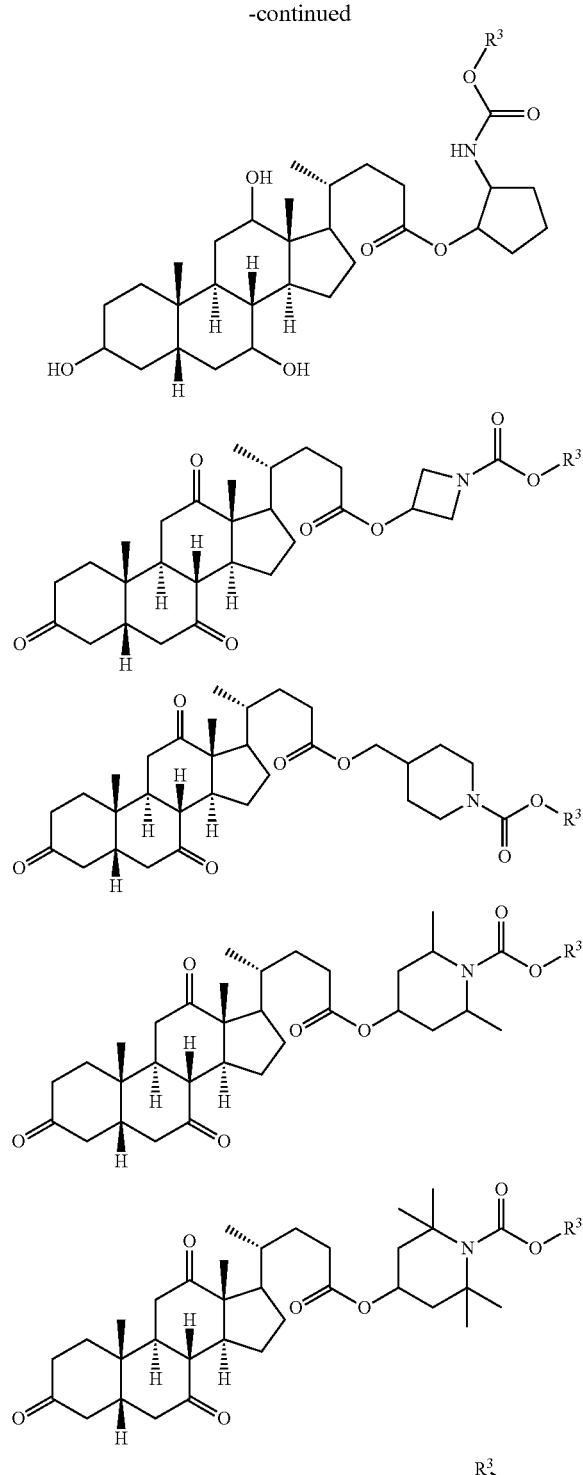
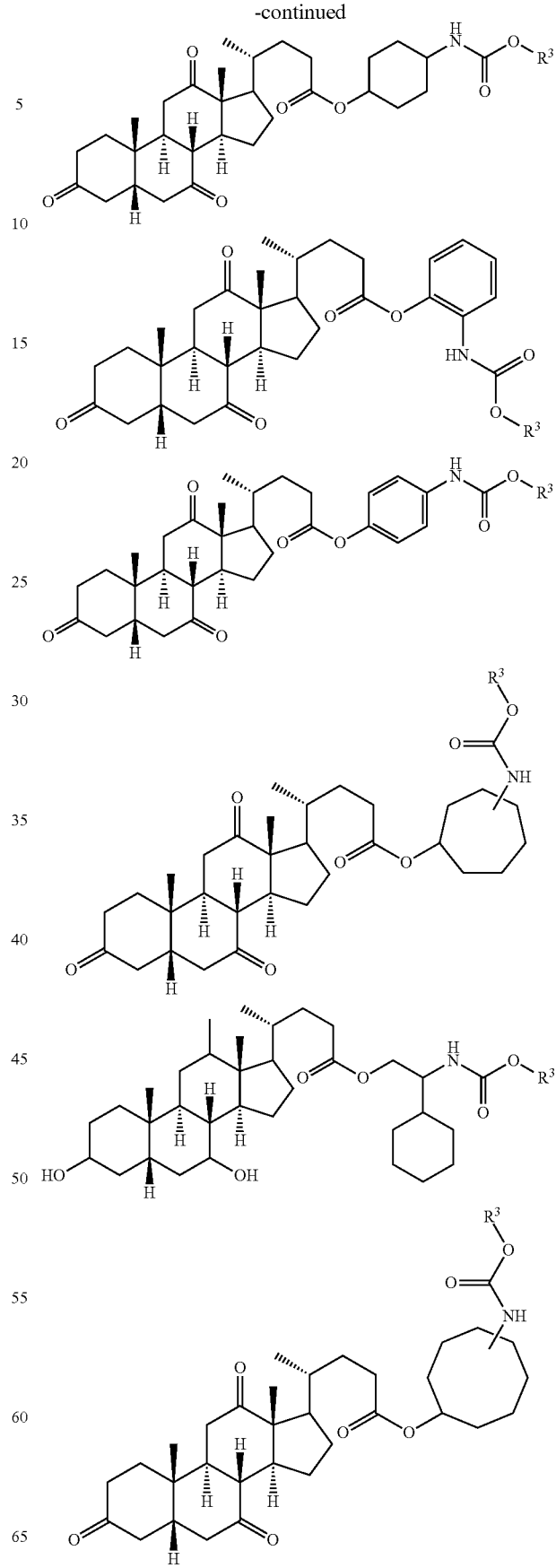

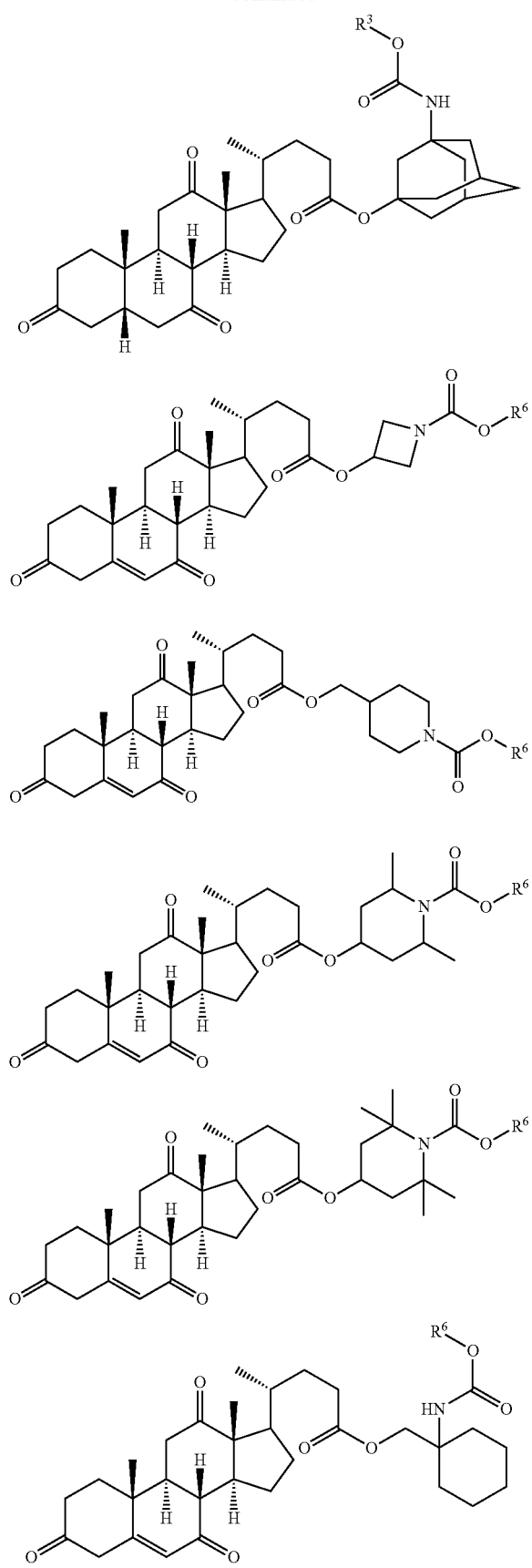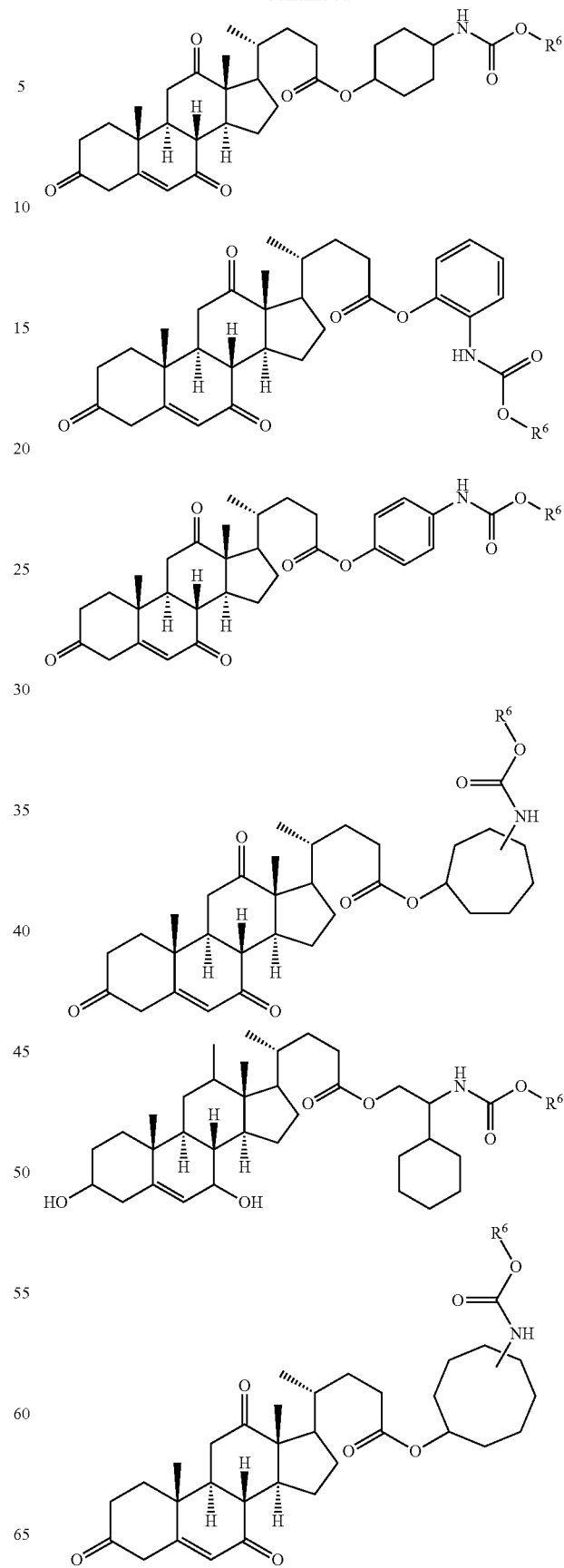

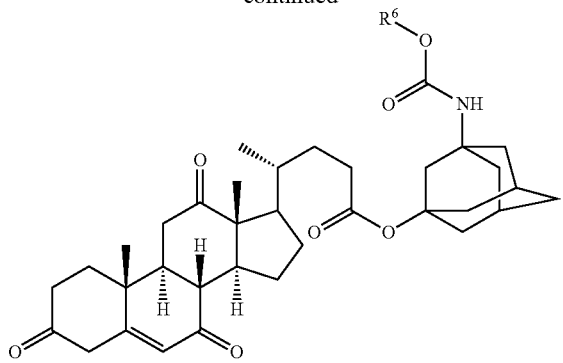

The resist composition comprising the cholanoate having an acid labile group-protected amino group may be either positive or negative, but should be a chemically amplified resist composition comprising an acid generator independent of whether it is positive or negative. When the cholanoate having an acid labile group-protected amino group collides with sulfonic acid, imidic acid or methide acid, the protective group is deprotected from the amino group so that the amino group increases basicity and hence, a neutralizing ability with acid. The cholanoate having an acid labile group-protected amino group has a steroid structure with a high molecular weight, which is effective for suppressing acid diffusion. As a result of suppressed acid diffusion, edge roughness is minimized.

The chemically amplified resist composition of the invention comprises the basic compound, i.e., cholanoate having an acid labile group-protected amino group represented by formula (1)-1 and/or (1)-2, a base polymer, and an acid generator, both to be described below. From the standpoints of sensitivity and acid diffusion control, the basic compound of formula (1)-1 and/or (1)-2 is preferably present in the composition in an amount of 0.001 to 30 parts by weight, more preferably 0.01 to 20 parts by weight per 100 parts by weight of the base polymer.

In the embodiment wherein chemically amplified resist compositions are positive, the base polymer comprises recurring units having an acid labile group. In the embodiment wherein chemically amplified resist compositions are negative, the base polymer comprises recurring units having a carboxyl or hydroxyl group which is not substituted with an acid labile group. Suitable recurring units which may or may not be substituted with an acid labile group include recurring units of (meth)acrylate, styrenecarboxylic acid and vinylnaphthalenecarboxylic acid which may or may not be substituted with an acid labile group, as represented by unit (a1) in the general formula (2), and recurring units of hydroxystyrene which may or may not be substituted with an acid labile group, as represented by unit (a2) in the general formula (2).

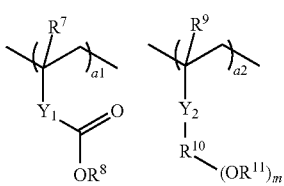

(2)

Herein, $R^7$ and $R^8$ each are hydrogen or methyl. $R^8$ and $R^{11}$ each are hydrogen or an acid labile group. $Y_1$ is a single bond, phenylene, naphthylene, or $-C(=O)-O-R^{12}-$. $R^{12}$ is a straight, branched or cyclic $C_1$-$C_{10}$ alkylene group which may have an ether moiety, ester moiety, lactone ring or hydroxyl moiety, or a phenylene or naphthylene group. $Y_2$ is a single bond, or a phenylene or naphthylene group which may have a nitro moiety, cyano moiety or halogen atom, or $-C(=O)-O-R^{13}-$, $-C(=O)-NH-R^{13}-$, $-O-R^{13}-$, or $-S-R^{13}-$. $R^{13}$ is a straight, branched or cyclic $C_1$-$C_{10}$ alkylene group which may have an ether moiety, ester moiety, lactone ring or hydroxyl moiety, or a phenylene or naphthylene group which may have a straight, branched or cyclic $C_1$-$C_6$ alkyl, alkoxy, acyl, acyloxy, $C_2$-$C_6$ alkenyl, alkoxycarbonyl, $C_6$-$C_{10}$ aryl, nitro, cyano or halogen atom. $R^{10}$ is a single bond, a di- to pentavalent, straight, branched or cyclic $C_1$-$C_{16}$ aliphatic hydrocarbon group, or phenylene group, which may have an ether or ester moiety. The subscripts a1 and a2 are numbers in the range: $0<a1\leq 1.0$, $0\leq a2\leq 1.0$, $0<a1+a2\leq 1.0$, and m is an integer of 1 to 4.

Monomers Ma1 and Ma2 from which recurring units (a1) and (a2) are derived have the following formulae, respectively.

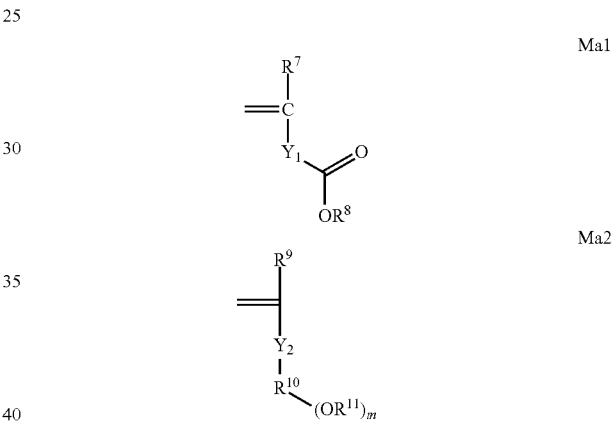

Herein $R^7$ to $R^{11}$, $Y_1$, $Y_2$ and m are as defined above.

Examples of the monomer Ma1 wherein $Y_1$ is a variant are illustrated below. $R^7$ and $R^8$ are as defined above.

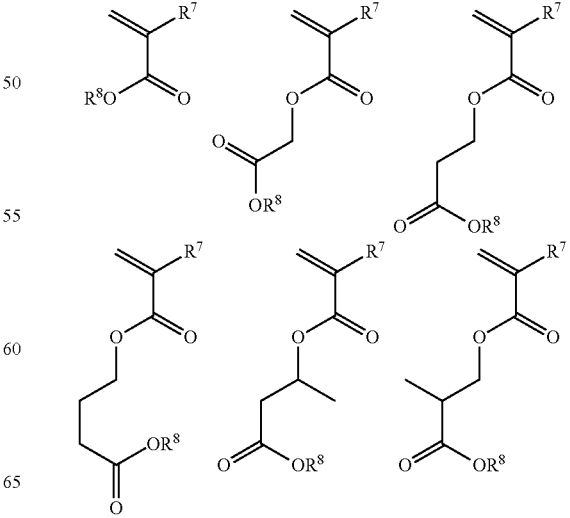

-continued
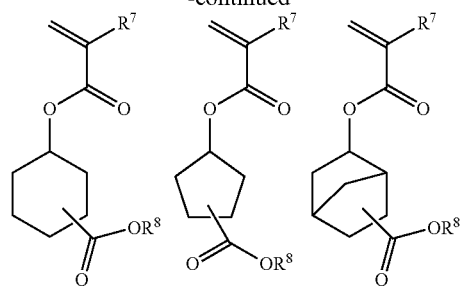
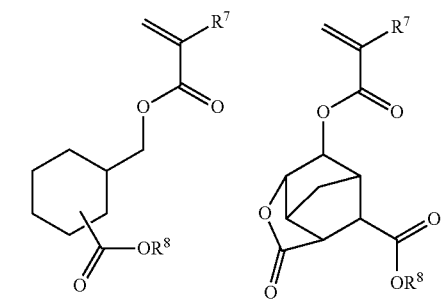
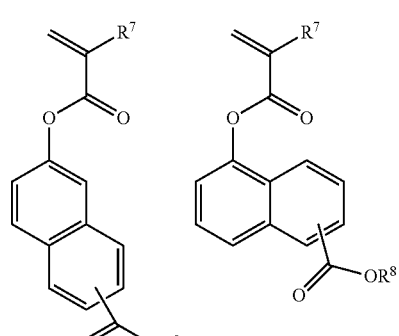
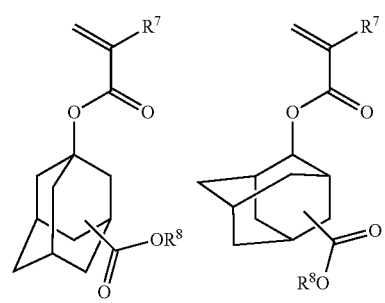
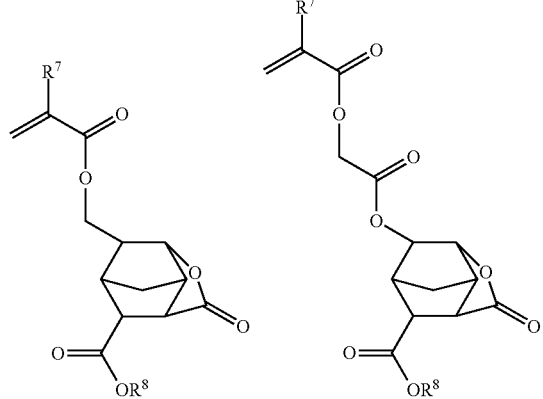
-continued
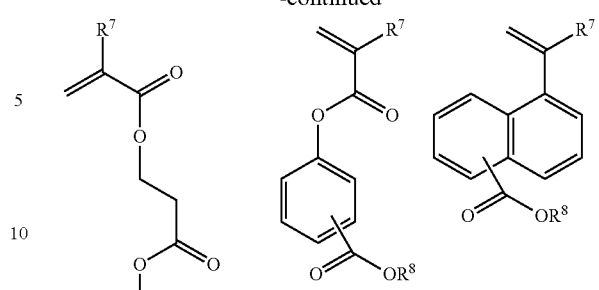
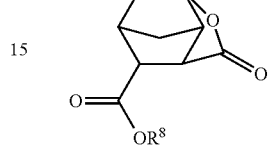
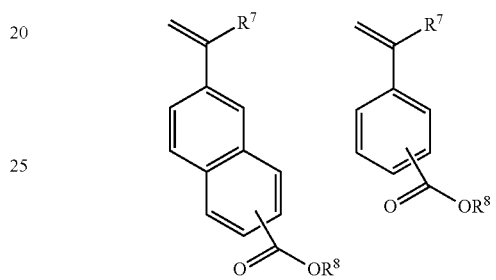
Examples of the monomer Ma2 are illustrated below. $R^9$ and $R^{11}$ are as defined above.
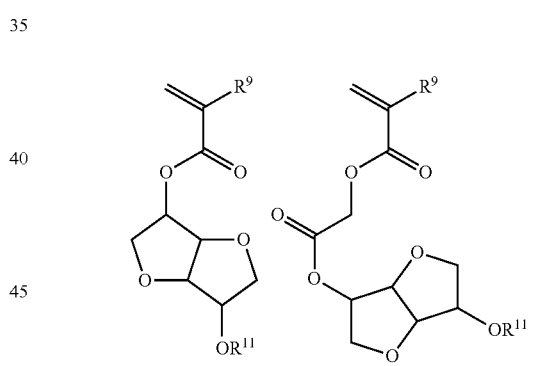
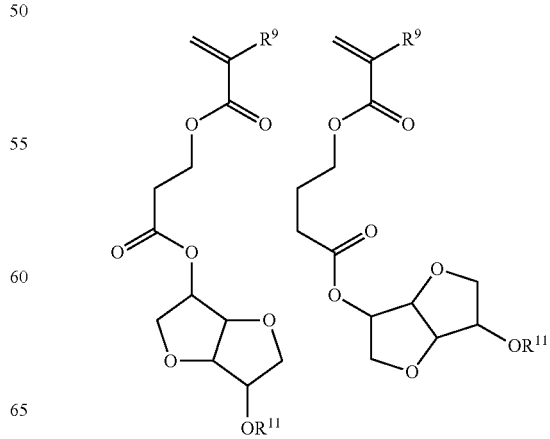

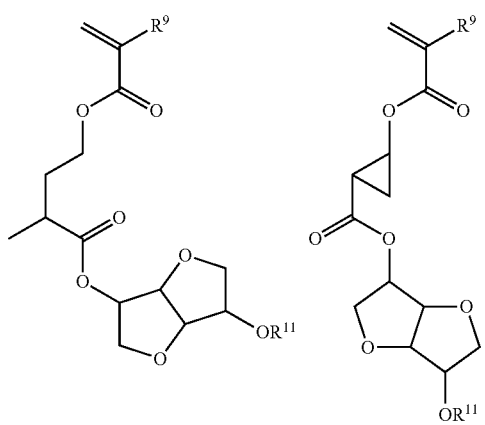
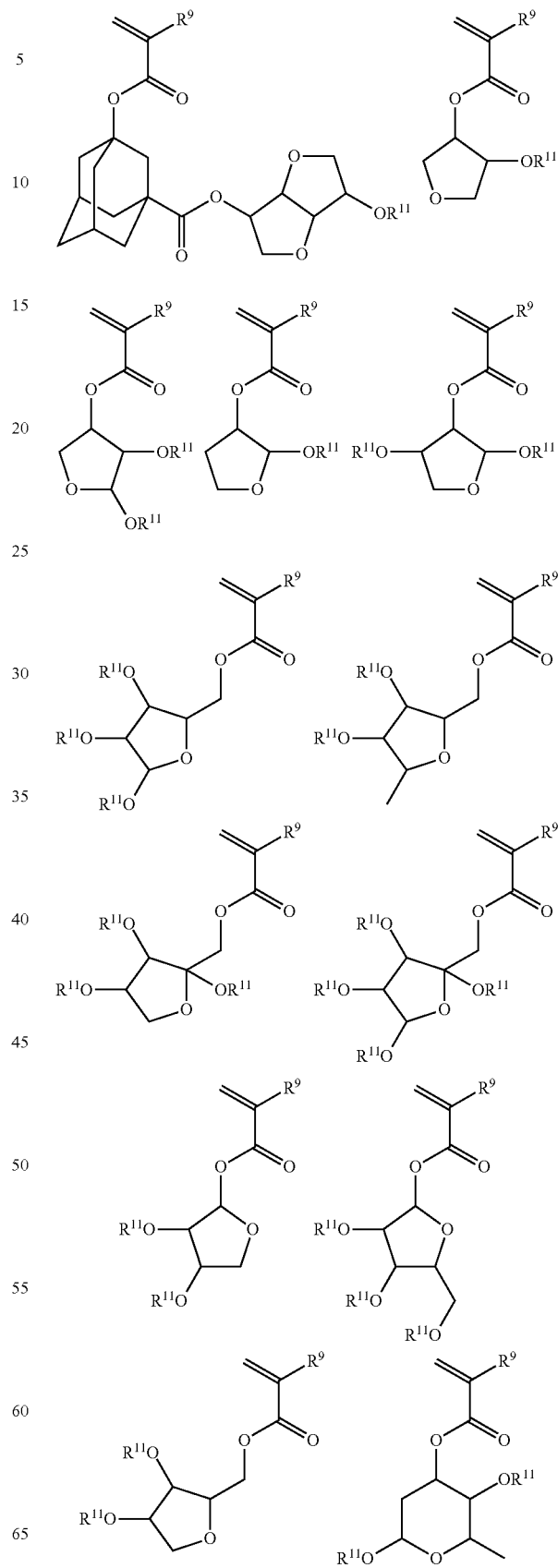

-continued
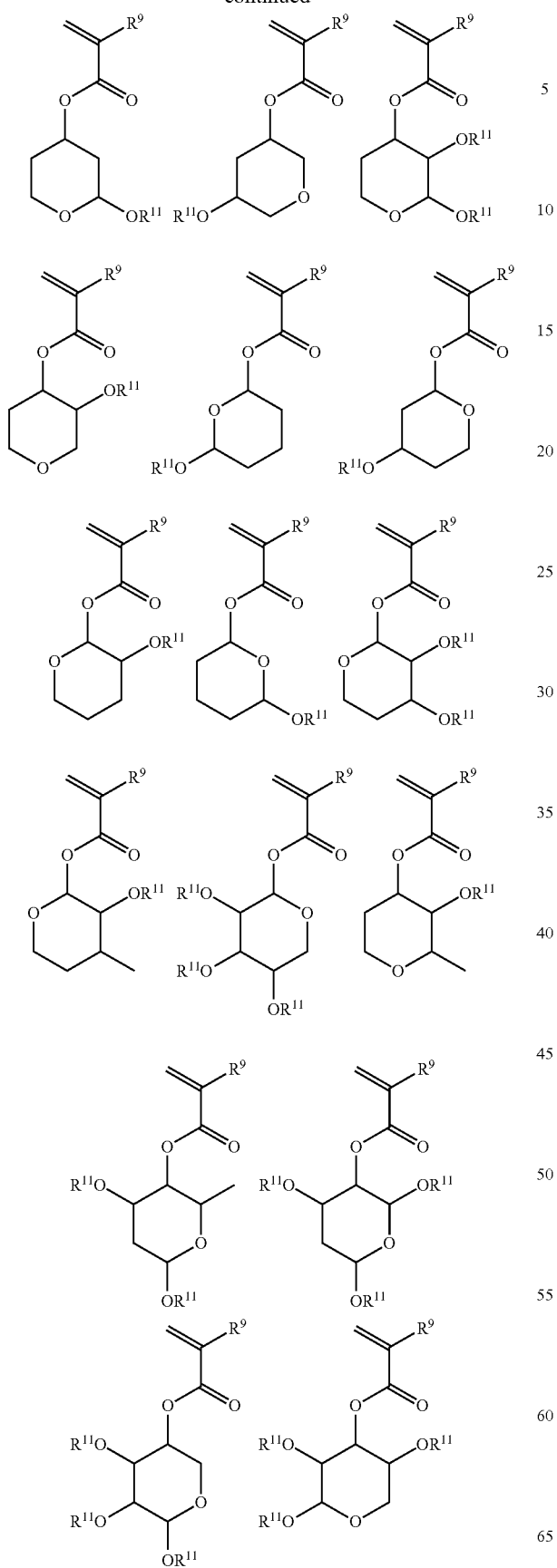
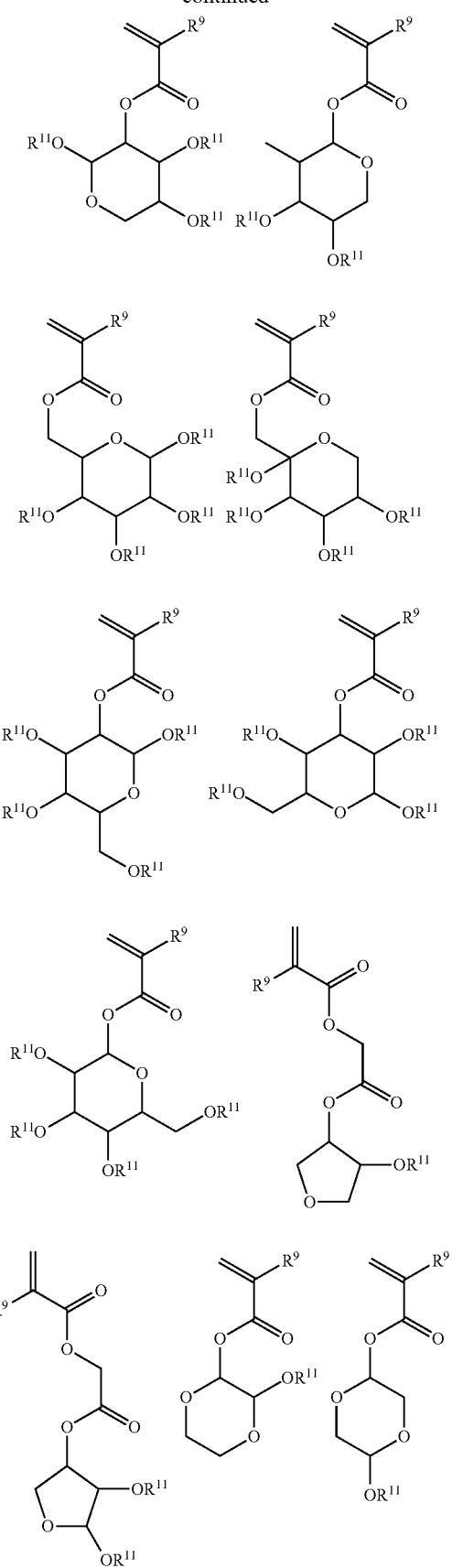

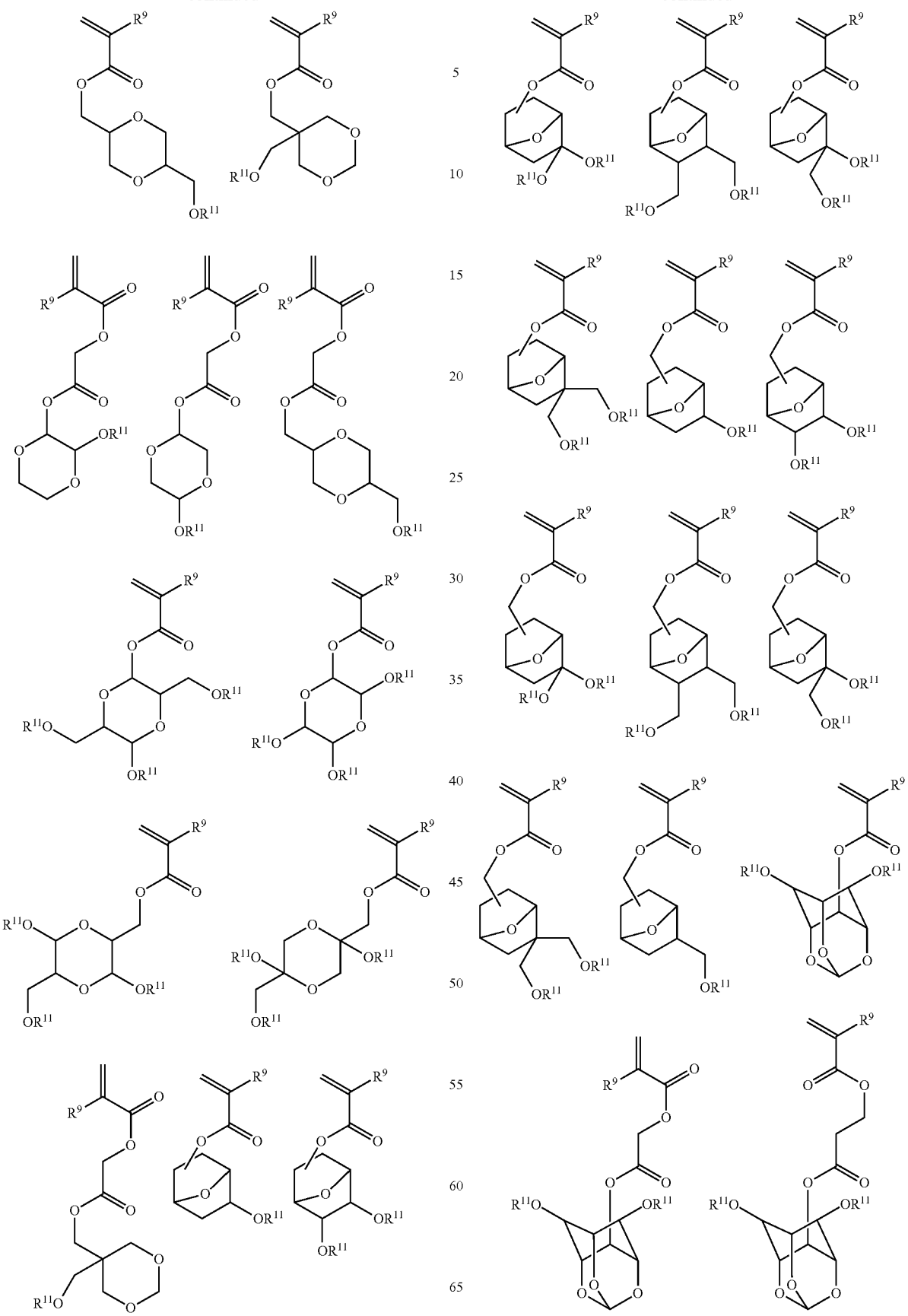

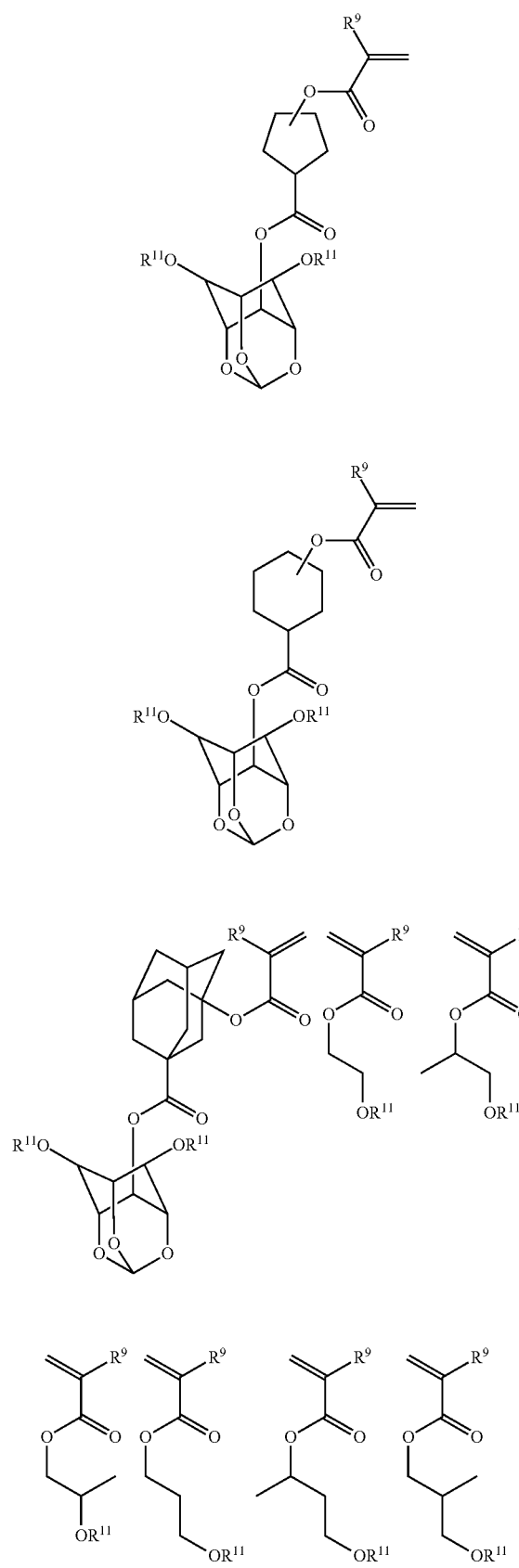
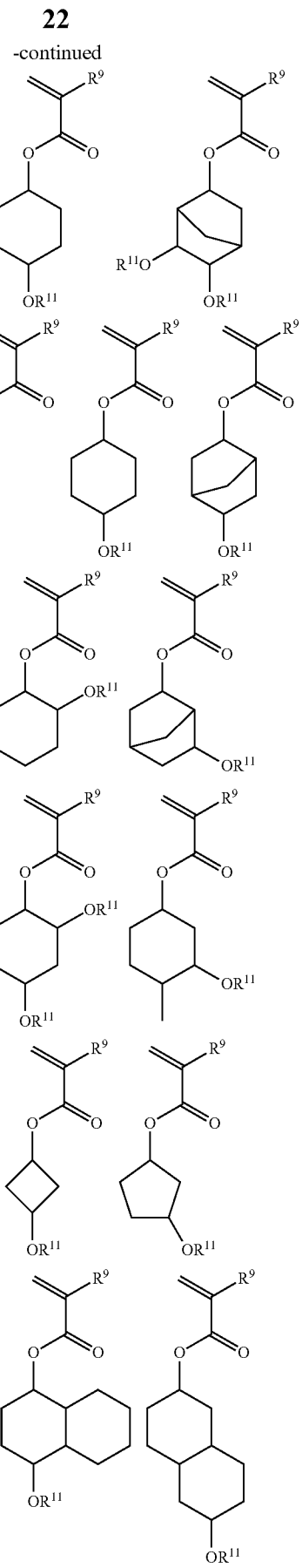

-continued
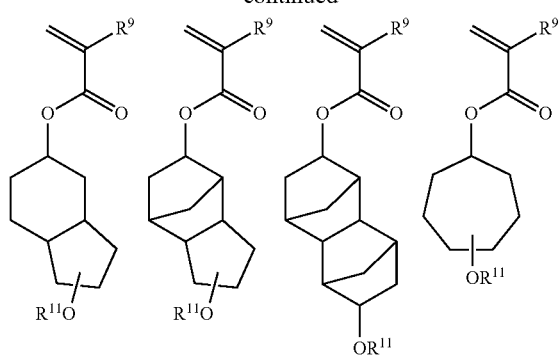
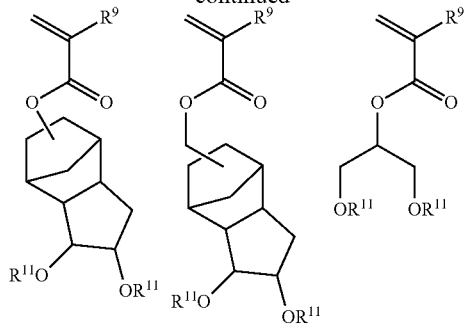
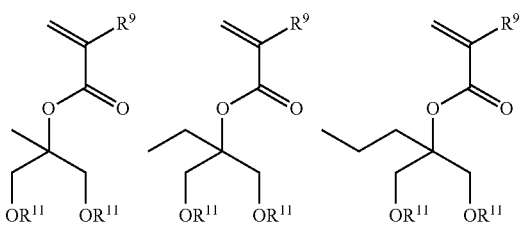
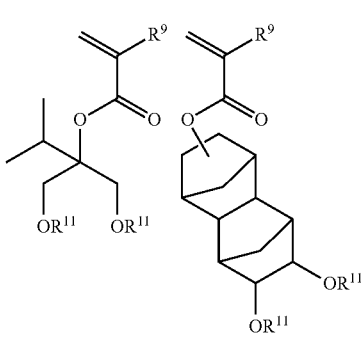
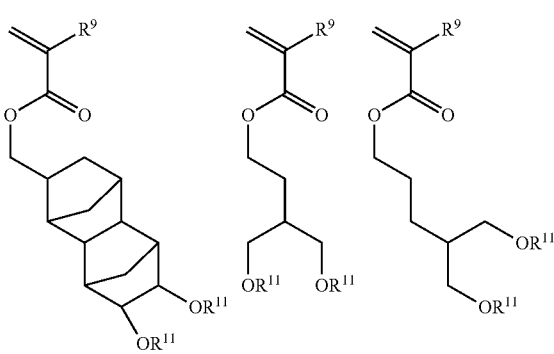
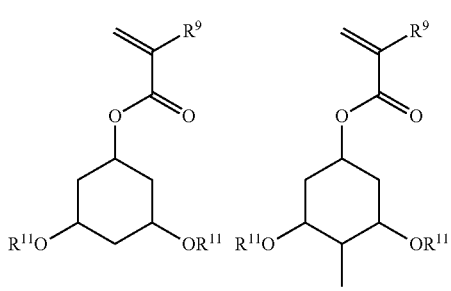

-continued
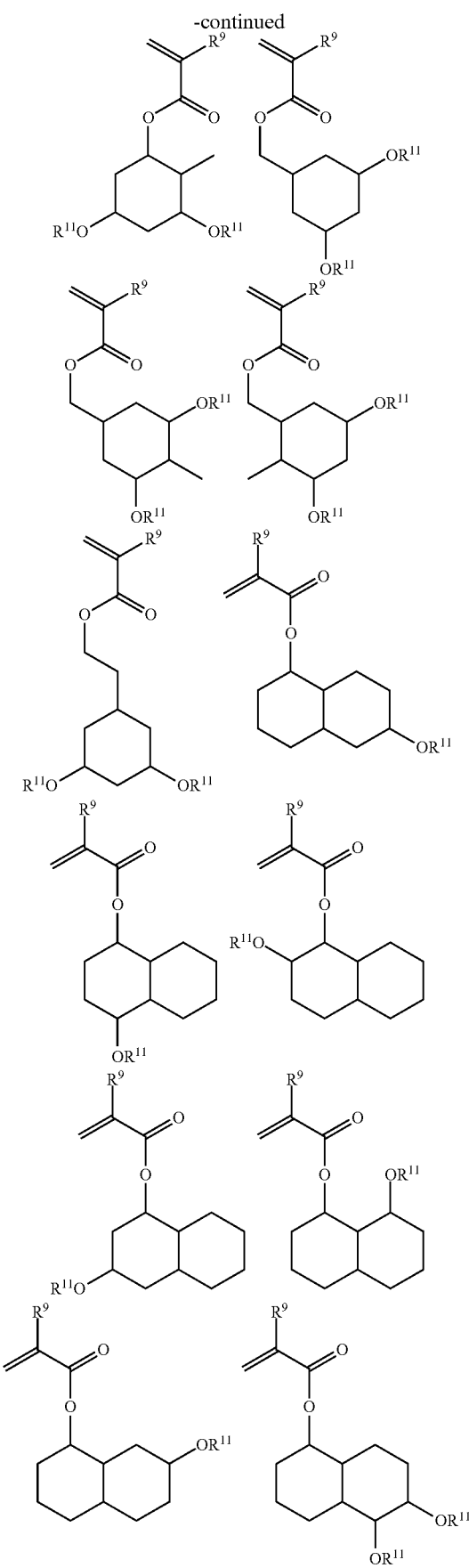
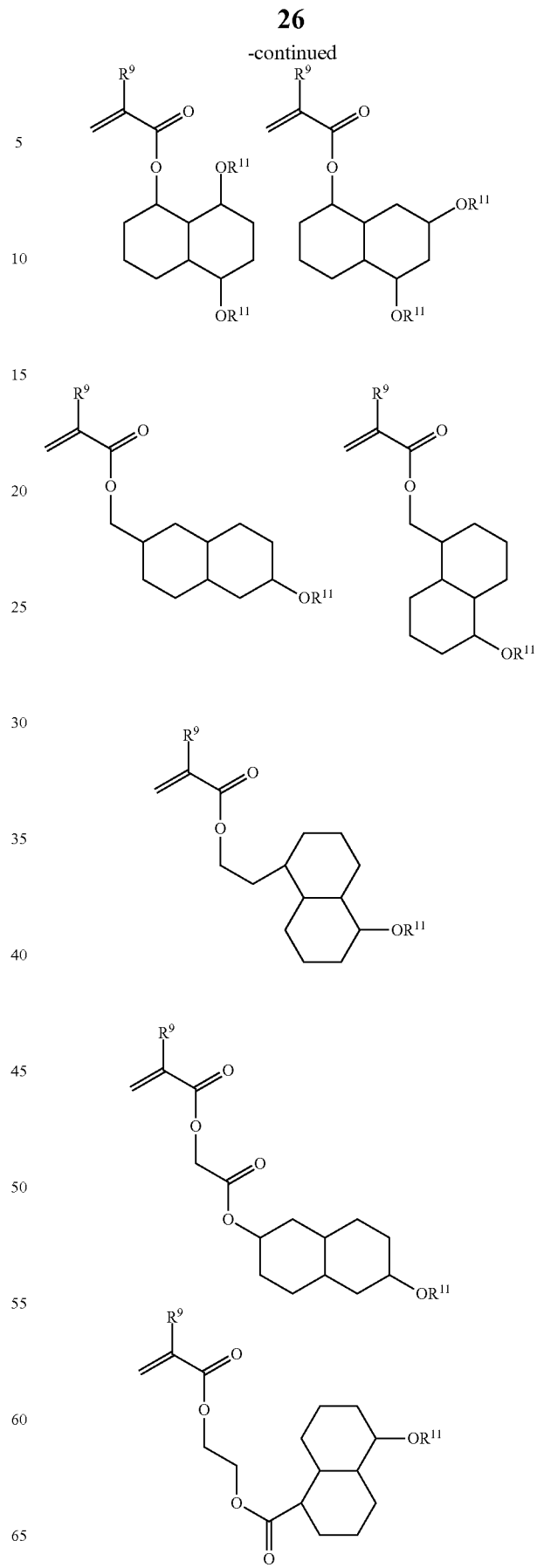

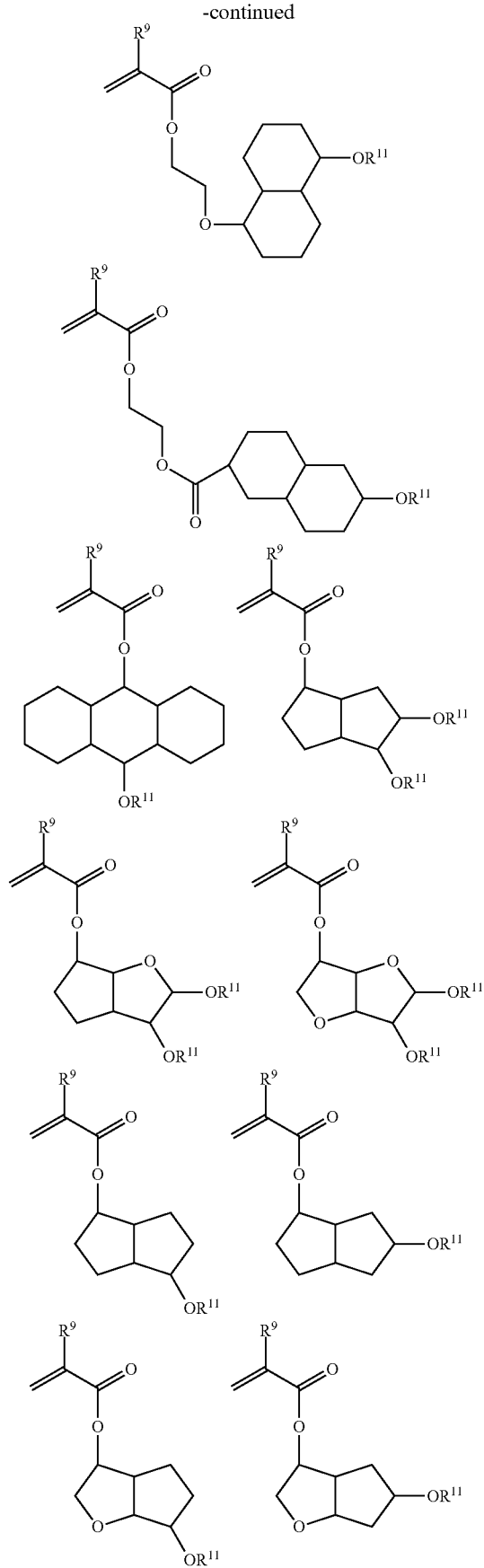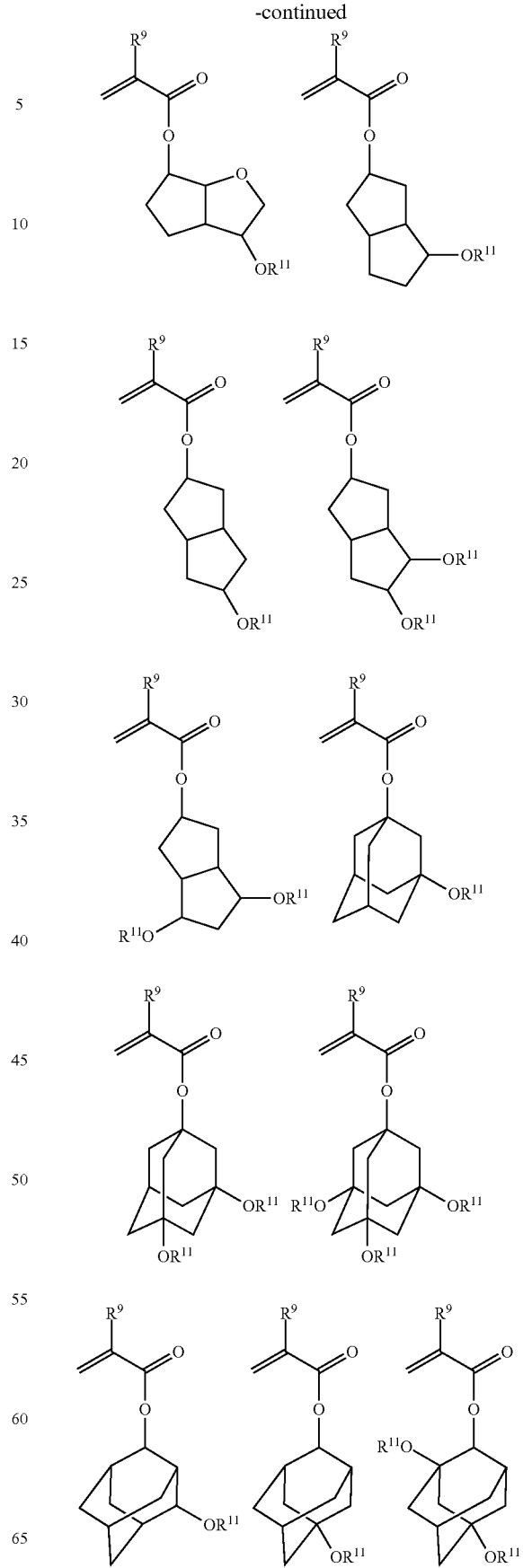

29
-continued
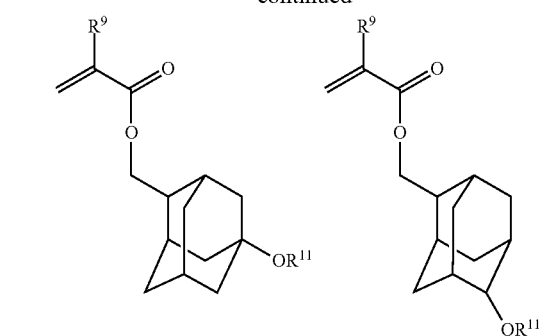
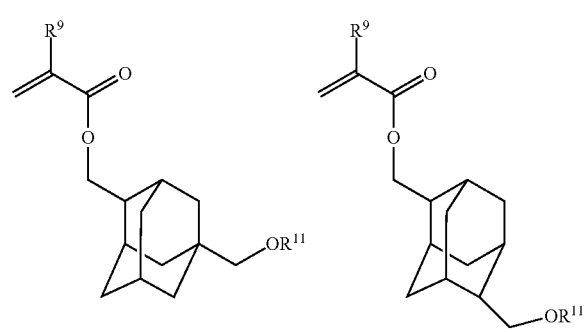
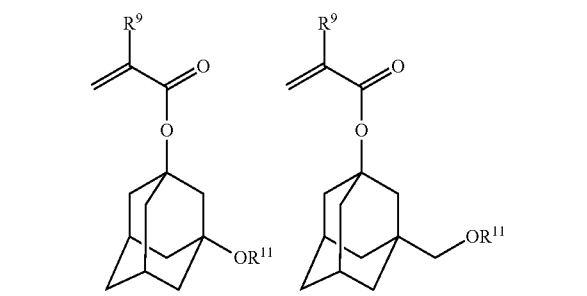
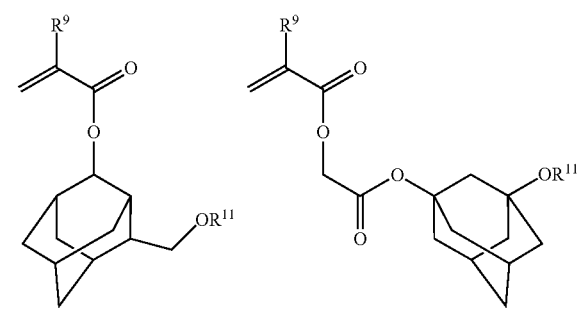
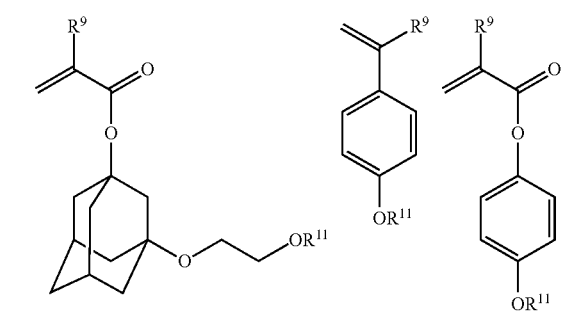
30
-continued
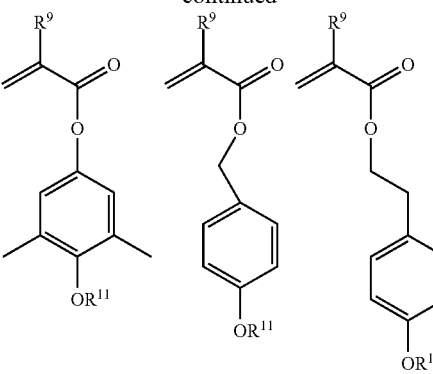
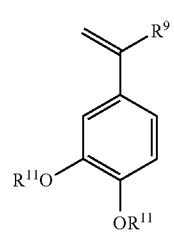
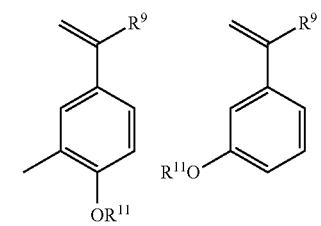
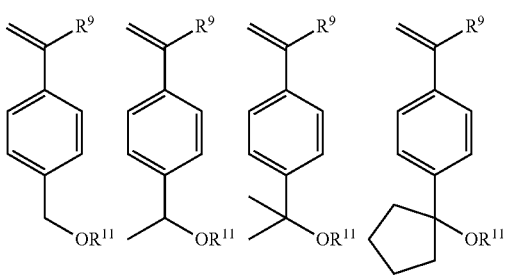
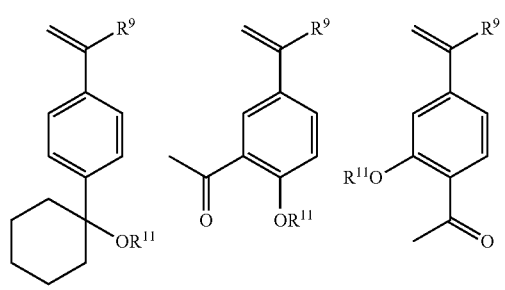

31
-continued
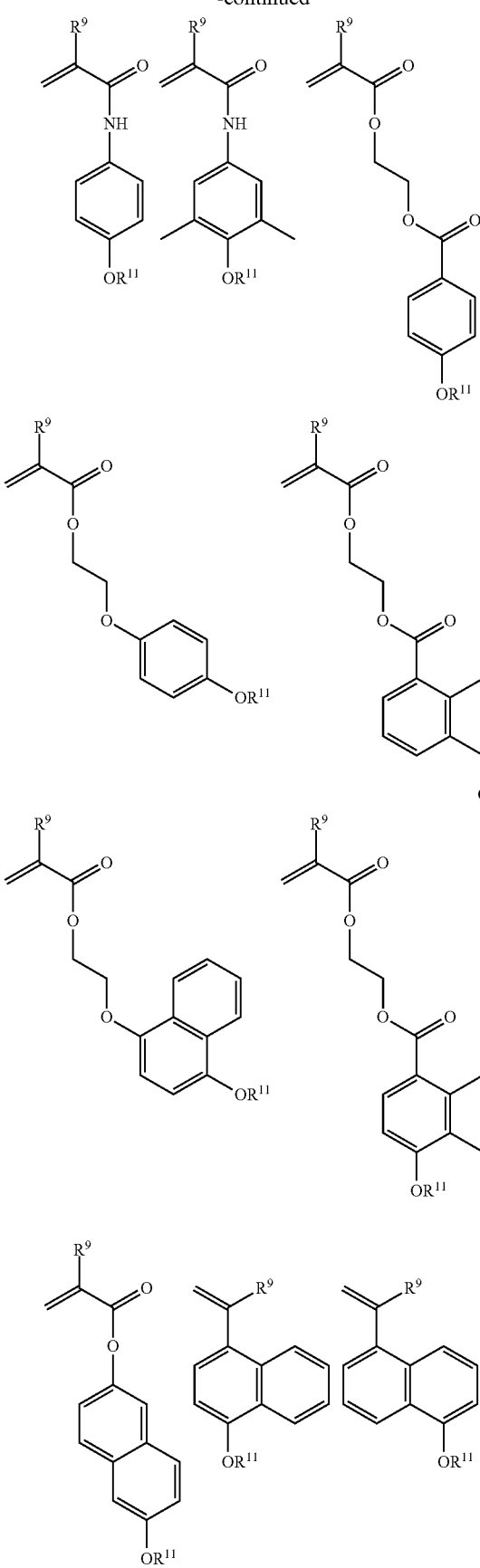
32
-continued
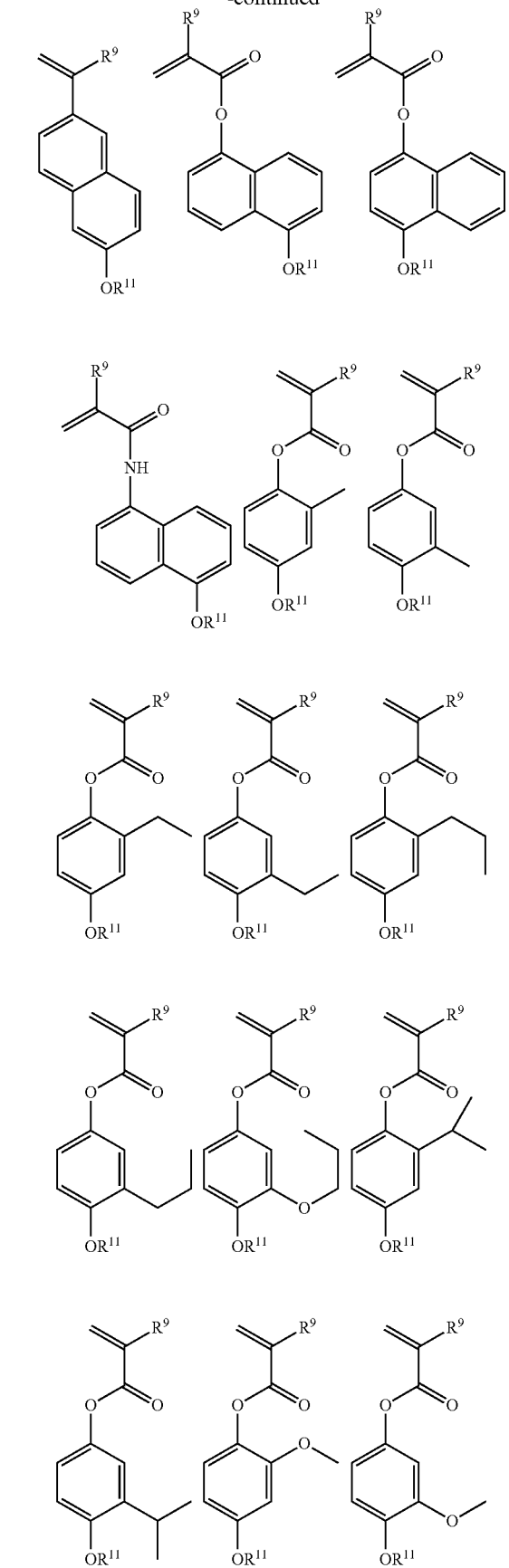

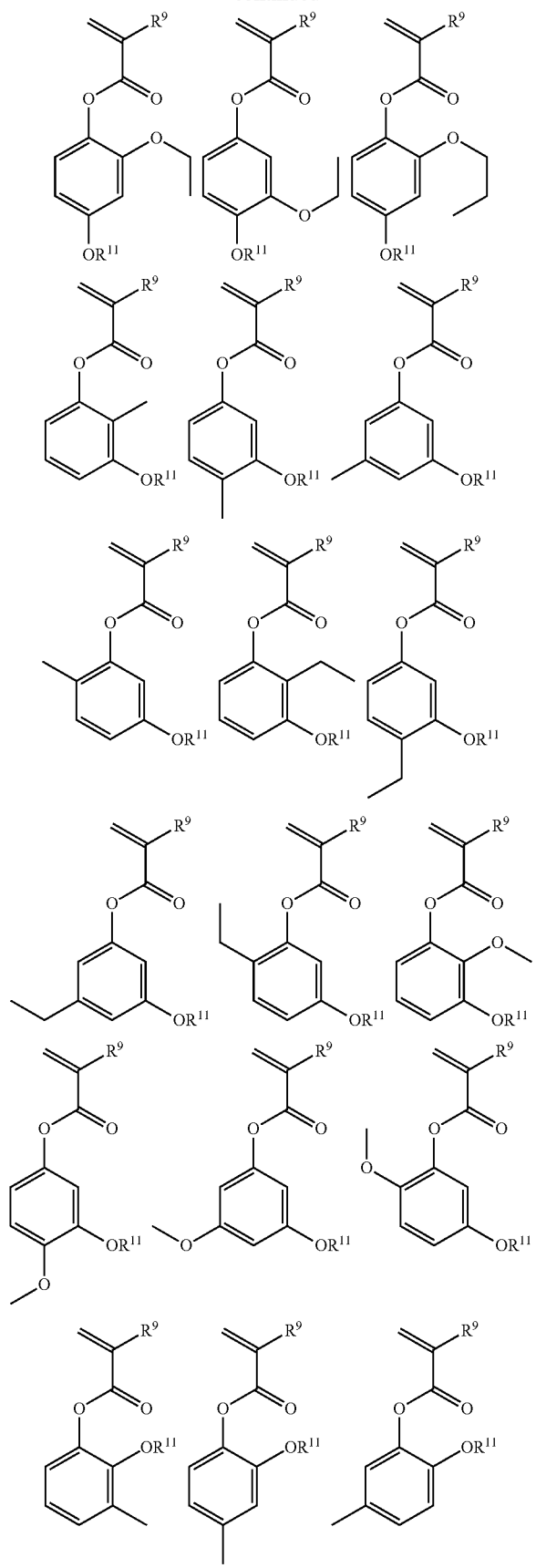
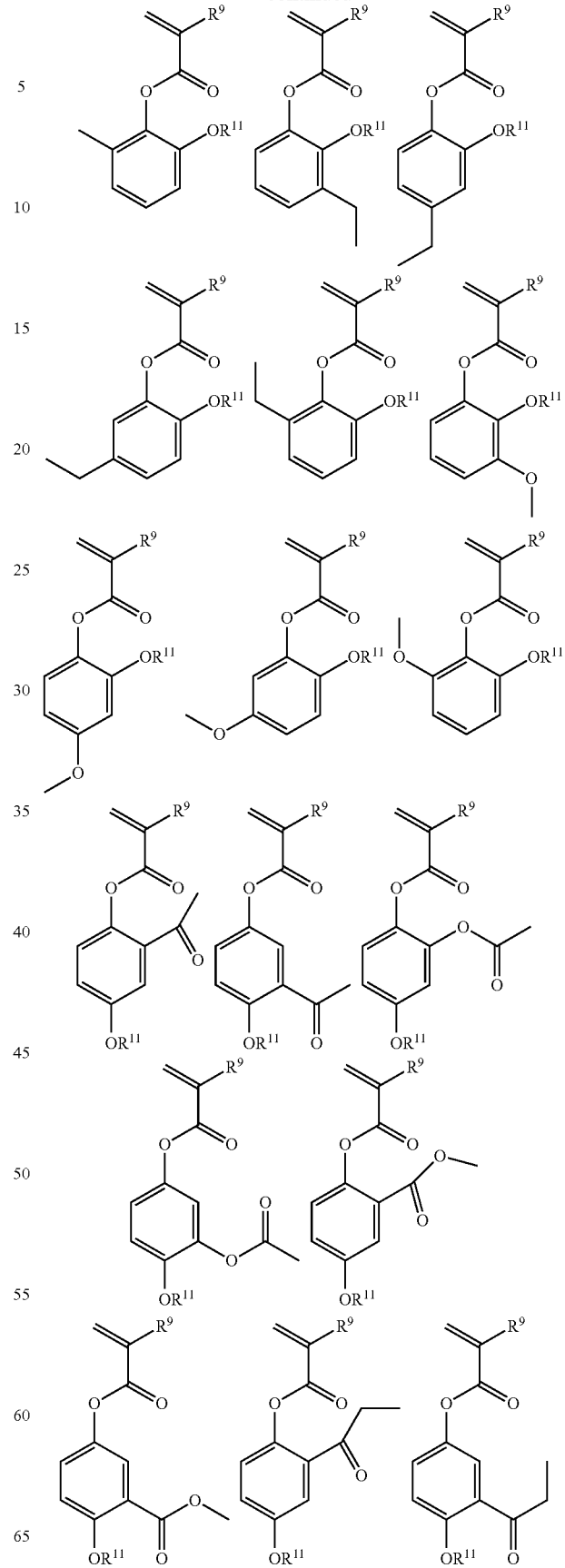

35
-continued
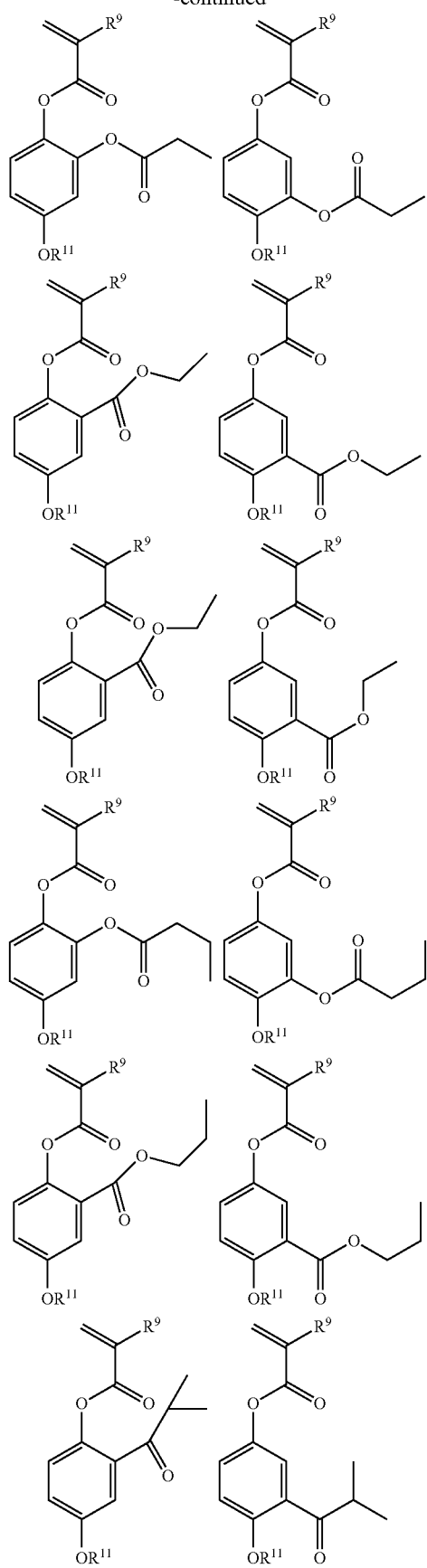
36
-continued
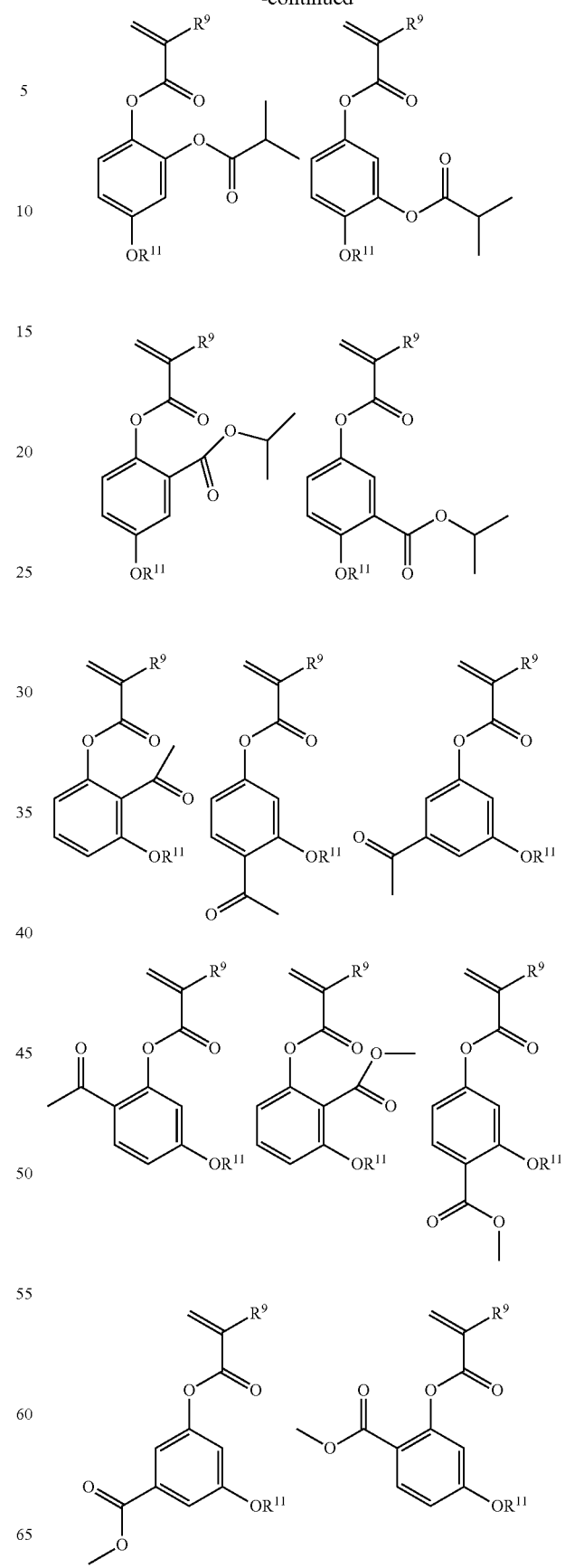

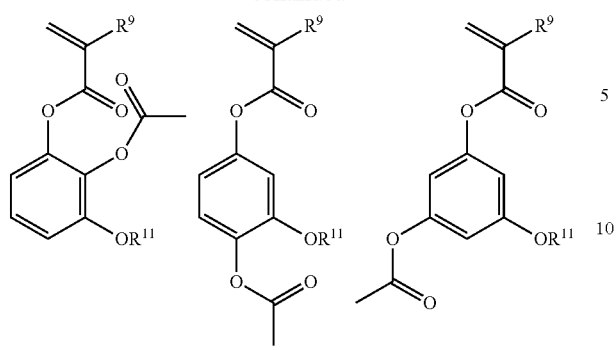
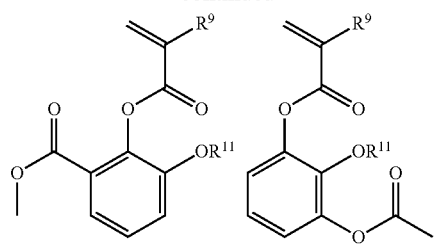
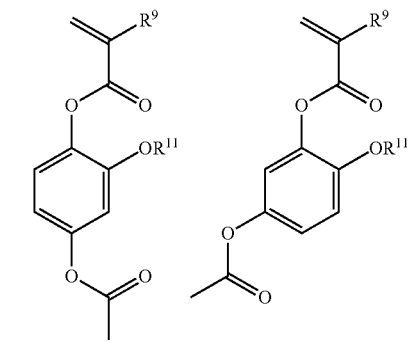
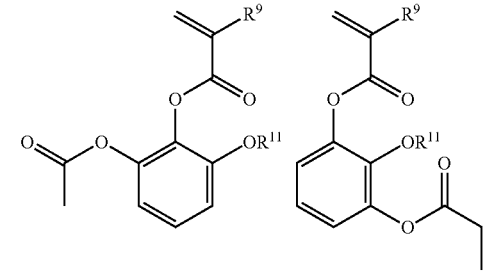
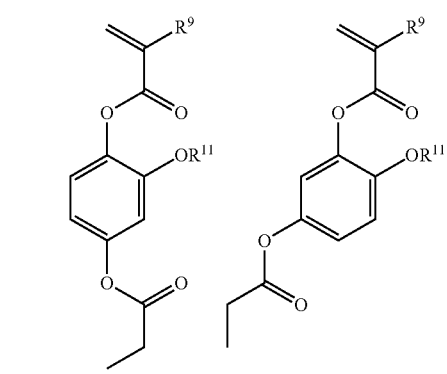
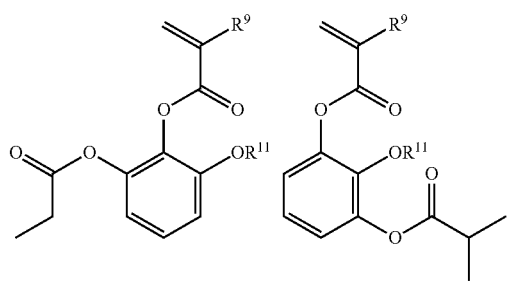

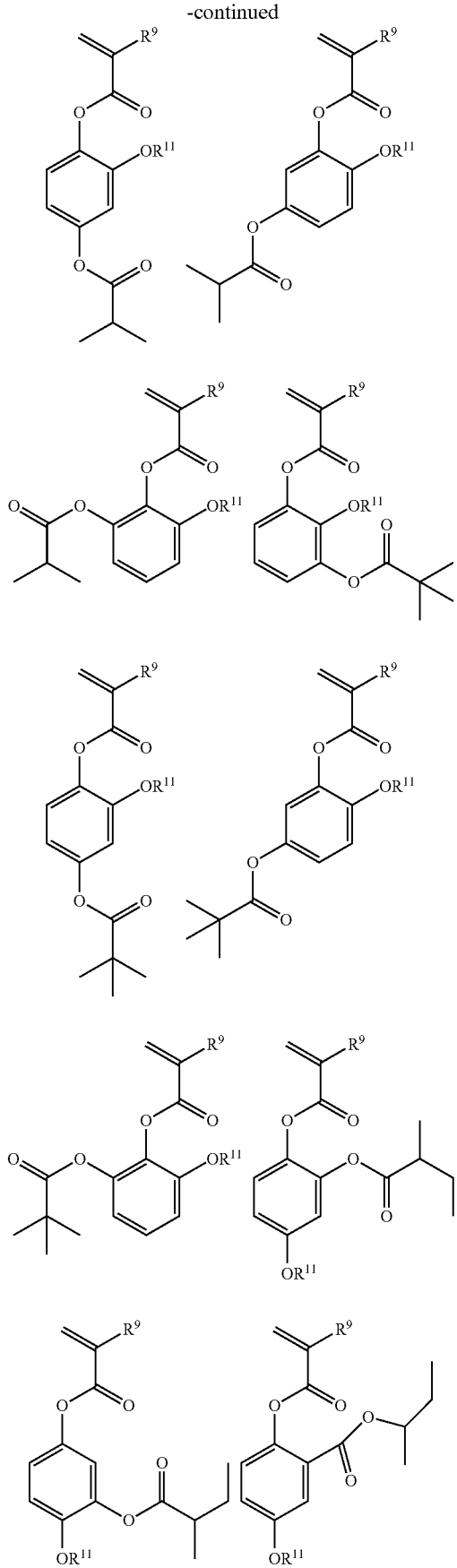
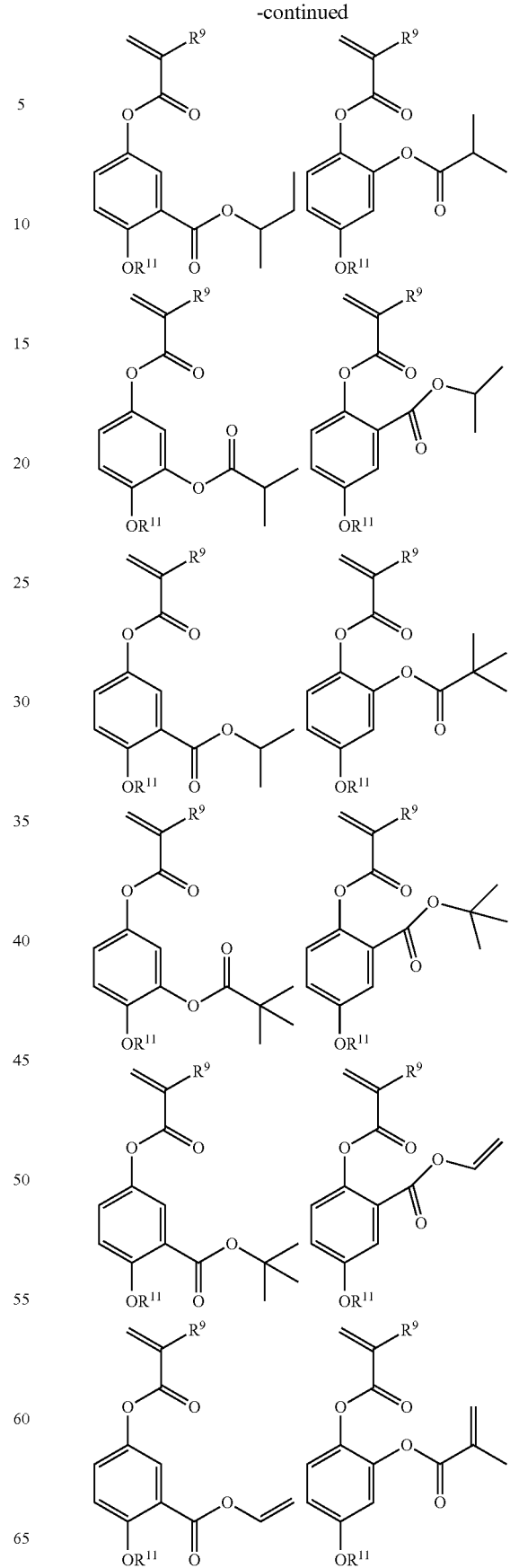

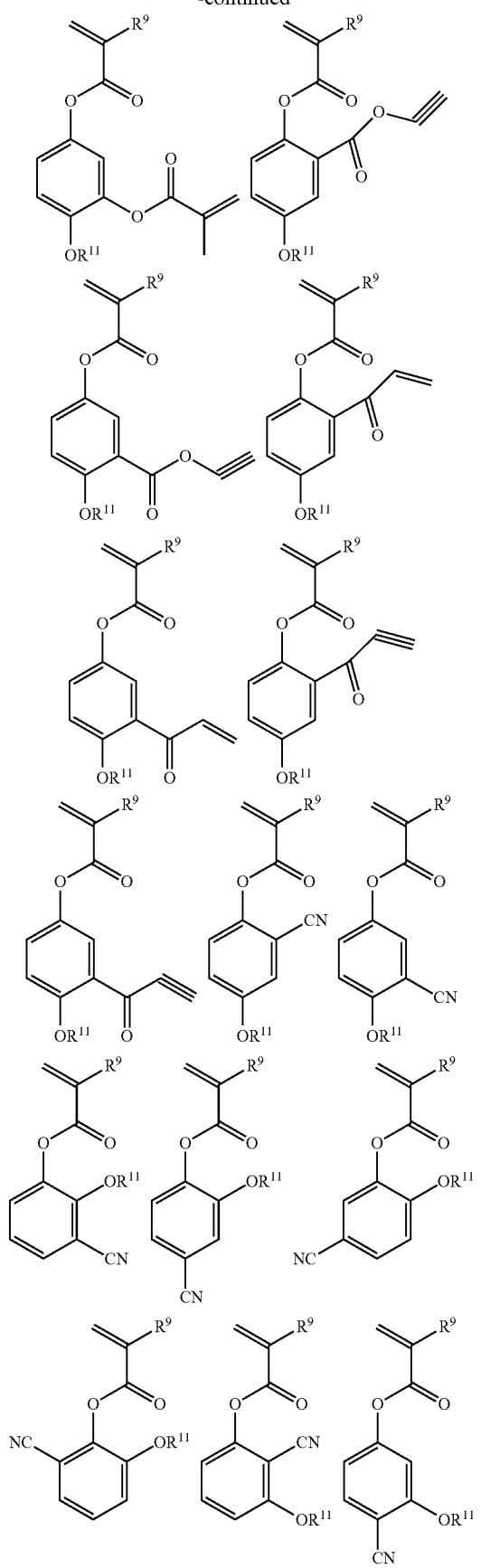
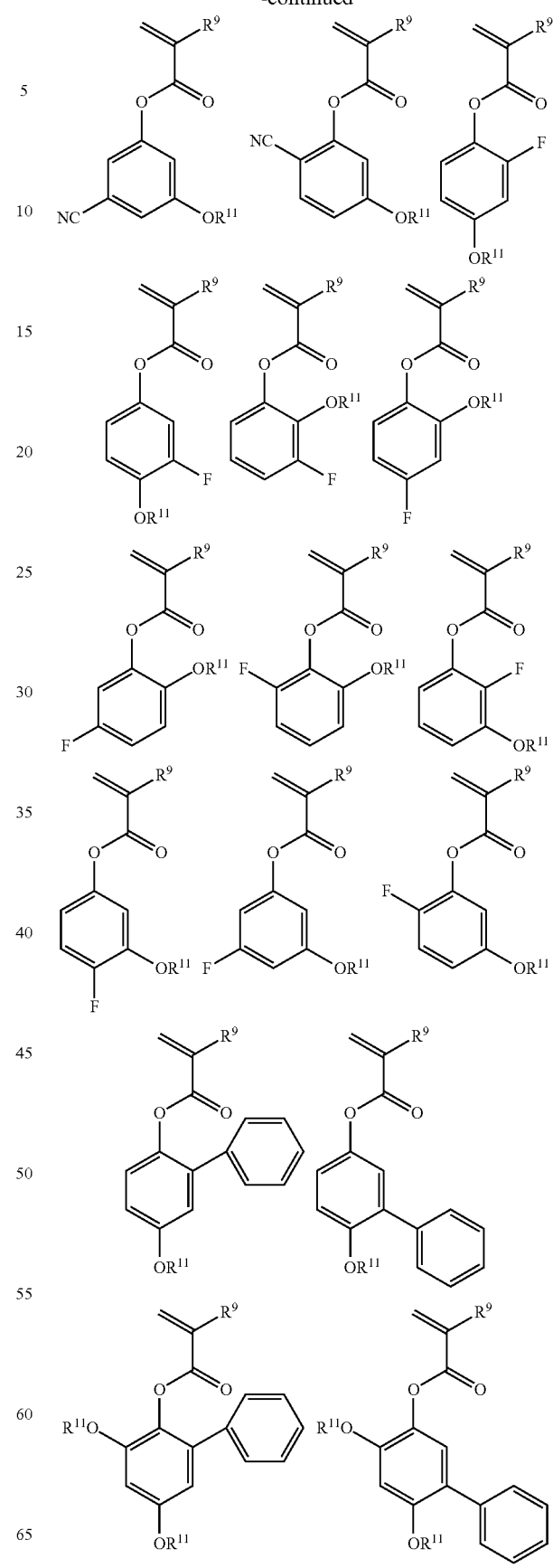

-continued
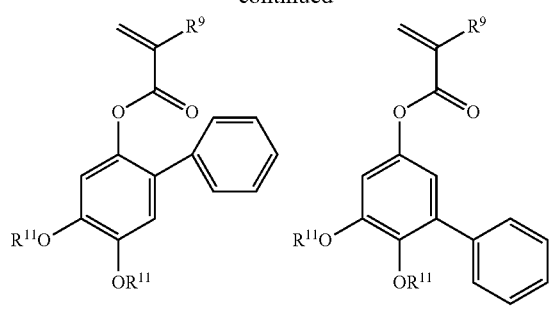
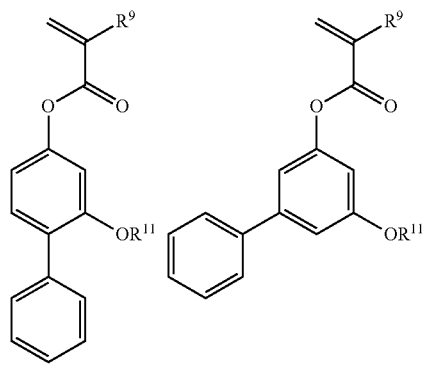
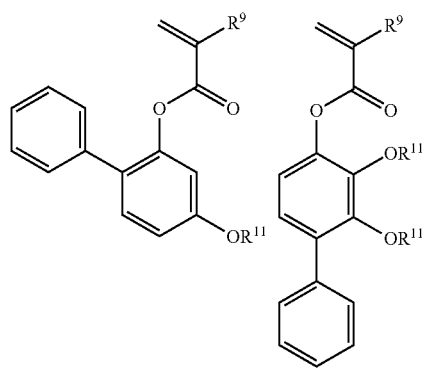
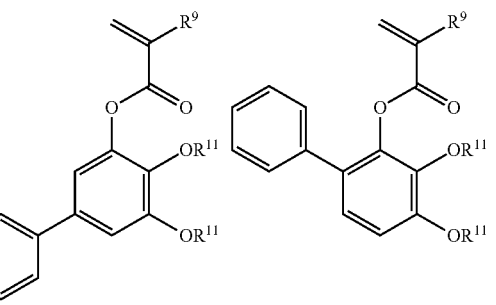
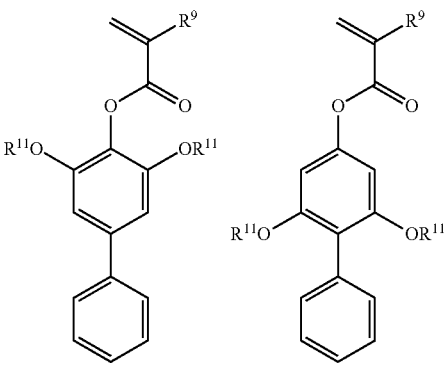
-continued
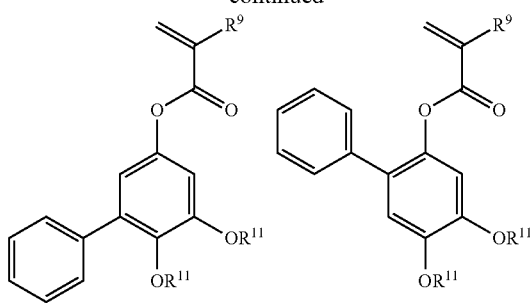
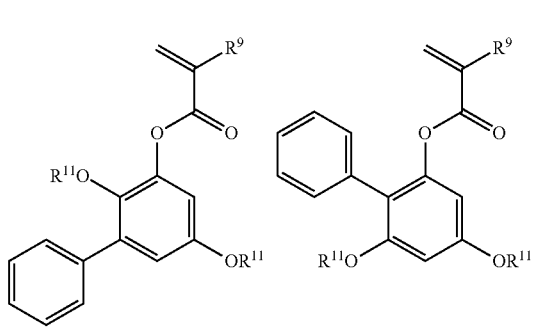
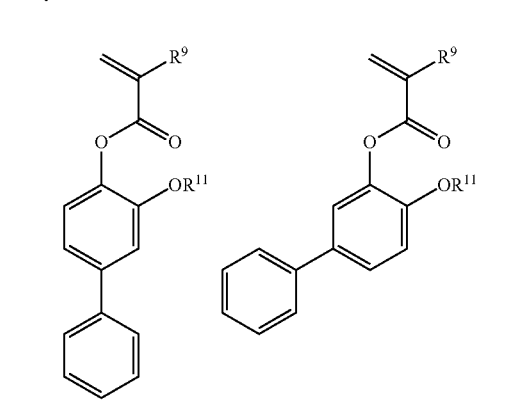
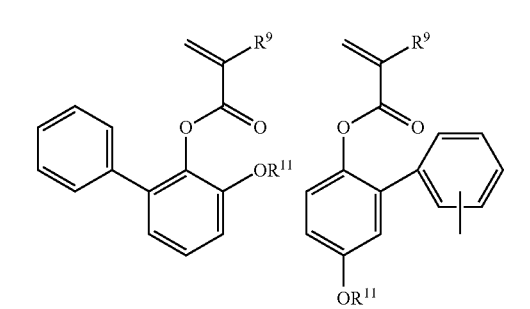
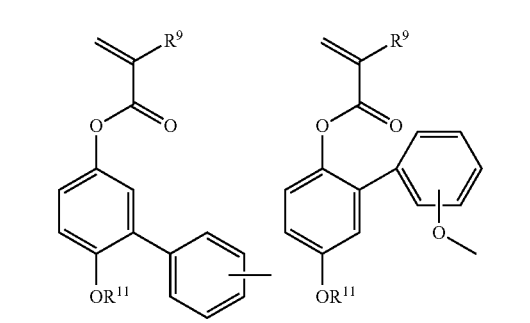

-continued
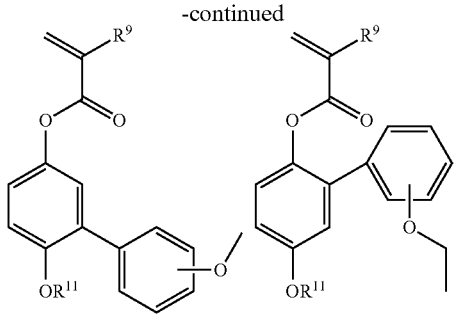
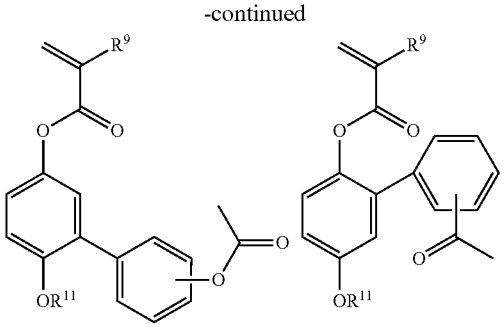
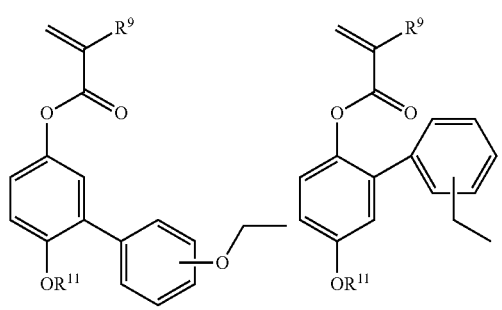
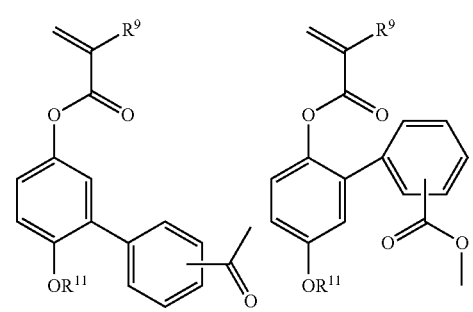
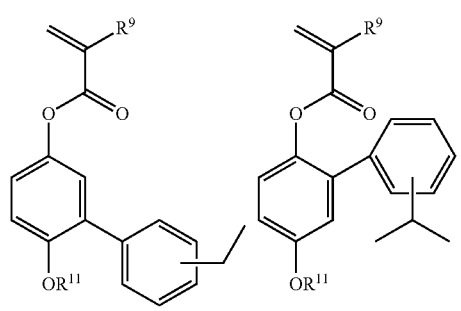
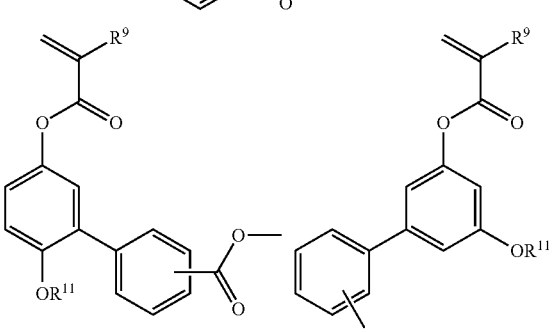
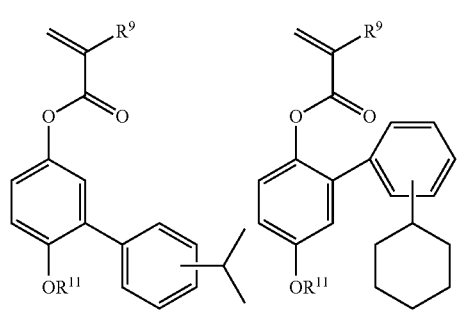
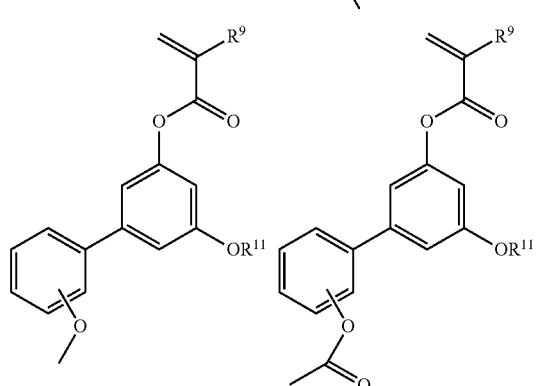
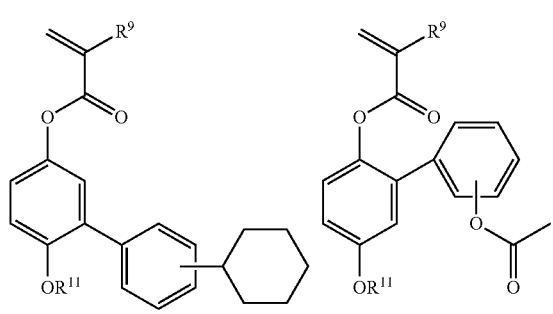
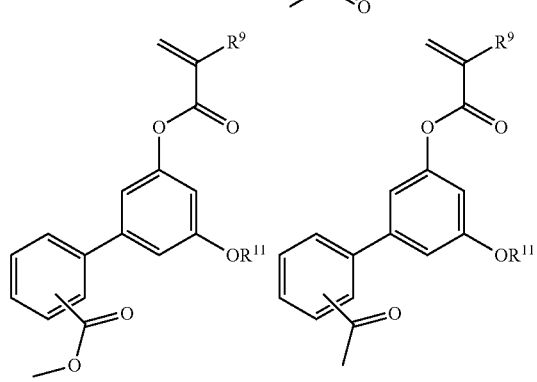

-continued

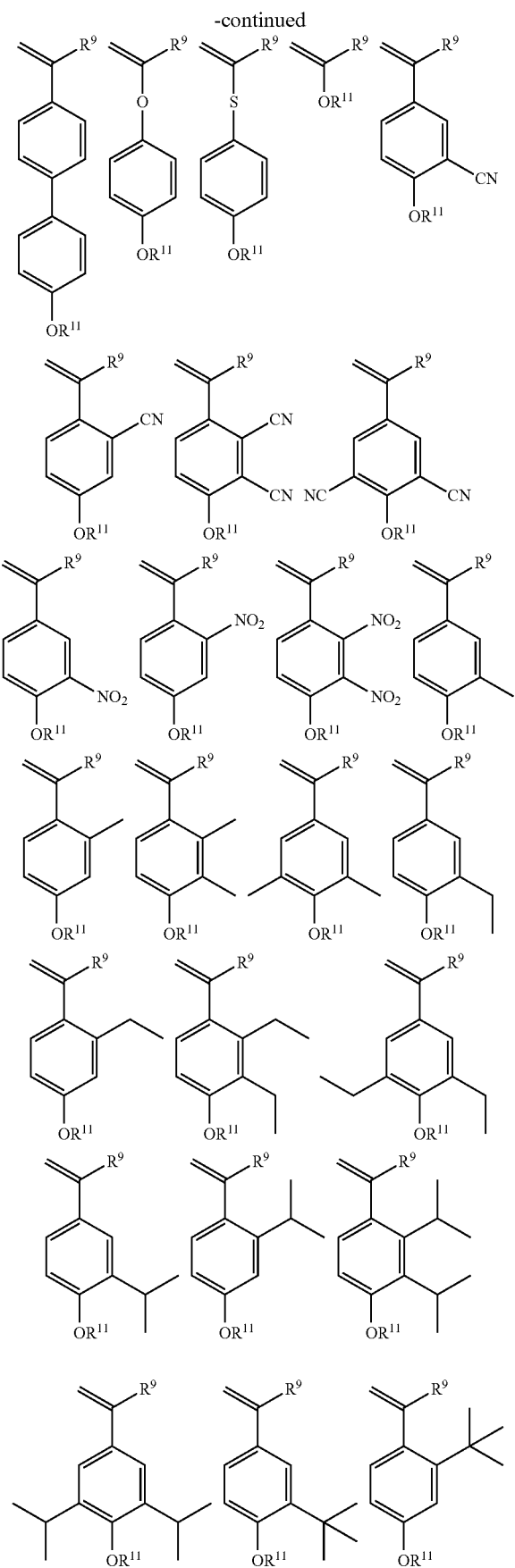

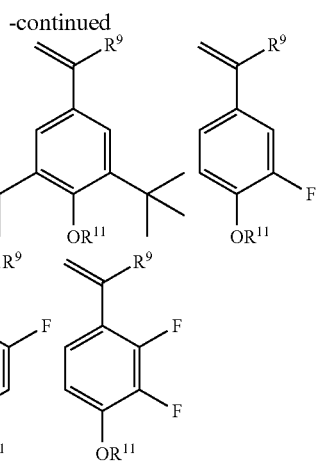

The acid labile group $R^3$ in formula (1)-1, acid labile group $R^6$ in formula (1)-2, acid labile group $R^8$ substituting on the carboxyl group in formula (2), and acid labile groups $R^{11}$ substituting on the hydroxyl group in formula (2) may be selected from a variety of such groups while they may be the same or different. Suitable acid labile groups include groups of the formula (AL-10), acetal groups of the formula (AL-11), tertiary alkyl groups of the formula (AL-12), and $C_4$-$C_{20}$ oxoalkyl groups, but are not limited thereto.

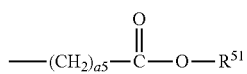
(AL-10)

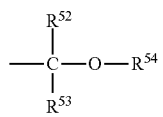
(AL-11)

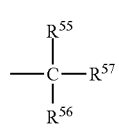
(AL-12)

In formulae (AL-10) and (AL-11), $R^{51}$ and $R^{54}$ each are a monovalent hydrocarbon group, typically straight, branched or cyclic alkyl group, of 1 to 40 carbon atoms, more specifically 1 to 20 carbon atoms, which may contain a heteroatom such as oxygen, sulfur, nitrogen or fluorine. $R^{52}$ and $R^{53}$ each are hydrogen or a monovalent hydrocarbon group, typically straight, branched or cyclic alkyl group, of 1 to 20 carbon atoms which may contain a heteroatom such as oxygen, sulfur, nitrogen or fluorine. The subscript "a5" is an integer of 0 to 10, and especially 1 to 5. Alternatively, a pair of $R^{52}$ and $R^{53}$, $R^{52}$ and $R^{54}$, or $R^{53}$ and $R^{54}$ may bond together to form a ring, specifically aliphatic ring, with the carbon atom or the carbon and oxygen atoms to which they are attached, the ring having 3 to 20 carbon atoms, especially 4 to 16 carbon atoms.

In formula (AL-12), $R^{55}$, $R^{56}$ and $R^{57}$ each are a monovalent hydrocarbon group, typically straight, branched or cyclic alkyl group, of 1 to 20 carbon atoms which may contain a heteroatom such as oxygen, sulfur, nitrogen or fluorine. Alternatively, a pair of $R^{55}$ and $R^{56}$, $R^{55}$ and $R^{57}$, or $R^{56}$ and $R^{57}$ may bond together to form a ring, specifically aliphatic ring, with the carbon atom to which they are attached, the ring having 3 to 20 carbon atoms, especially 4 to 16 carbon atoms.

Illustrative examples of the acid labile group of formula (AL-10) include tert-butoxycarbonyl, tert-butoxycarbonylmethyl, tert-amyloxycarbonyl, tert-amyloxycarbonylmethyl, 1-ethoxyethoxycarbonylmethyl, 2-tetrahydropyranyloxycarbonylmethyl and 2-tetrahydrofuranyloxycarbonylmethyl as well as substituent groups of the following formulae (AL-10)-1 to (AL-10)-10.

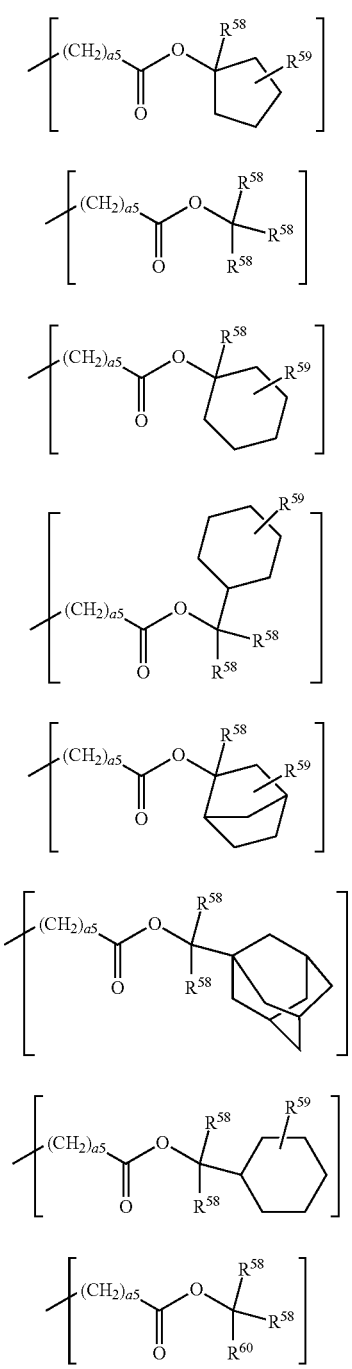
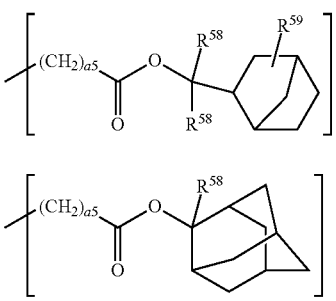

In formulae (AL-10)-1 to (AL-10)-10, $R^{58}$ is each independently a straight, branched or cyclic $C_1$-$C_8$ alkyl group, $C_6$-$C_{20}$ aryl group or $C_7$-$C_{20}$ aralkyl group; $R^{59}$ is hydrogen or a straight, branched or cyclic $C_1$-$C_{20}$ alkyl group; $R^{63}$ is a $C_6$-$C_{20}$ aryl group or $C_7$-$C_{20}$ aralkyl group; and a5 is an integer of 0 to 10, especially 1 to 5.

Illustrative examples of the acetal group of formula (AL-11) include those of the following formulae (AL-11)-1 to (AL-11)-112.

$$\text{—CH}_2\text{—O—CH}_3 \quad \text{(AL-11)-1}$$

$$\text{—CH}_2\text{—O—CH}_2\text{—CH}_3 \quad \text{(AL-11)-2}$$

$$\text{—CH}_2\text{—O—(CH}_2)_2\text{—CH}_3 \quad \text{(AL-11)-3}$$

$$\text{—CH}_2\text{—O—(CH}_2)_3\text{—CH}_3 \quad \text{(AL-11)-4}$$

$$\text{—CH}_2\text{—O—CH(CH}_3)\text{—CH}_3 \quad \text{(AL-11)-5}$$

$$\text{—CH}_2\text{—O—C(CH}_3)_2\text{—CH}_3 \quad \text{(AL-11)-6}$$

$$\text{—CH(CH}_3)\text{—O—CH}_3 \quad \text{(AL-11)-7}$$

$$\text{—CH(CH}_2\text{CH}_3)\text{—O—CH}_3 \quad \text{(AL-11)-8}$$

$$\text{—CH((CH}_2)_2\text{CH}_3)\text{—O—CH}_3 \quad \text{(AL-11)-9}$$

$$\text{—CH(CH}_3)\text{—O—CH}_2\text{—CH}_3 \quad \text{(AL-11)-10}$$

$$\text{—CH(CH}_2\text{CH}_3)\text{—O—CH}_2\text{—CH}_3 \quad \text{(AL-11)-11}$$

(AL-11)-12 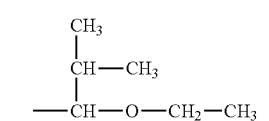
(AL-11)-13 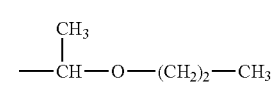
(AL-11)-14 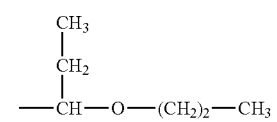
(AL-11)-15 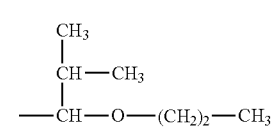
(AL-11)-16 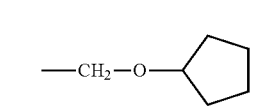
(AL-11)-17 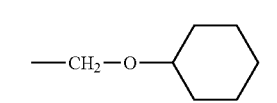
(AL-11)-18 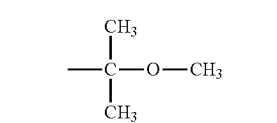
(AL-11)-19 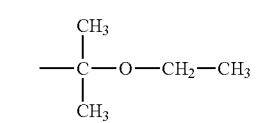
(AL-11)-20 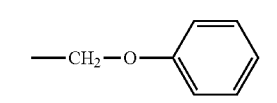
(AL-11)-21 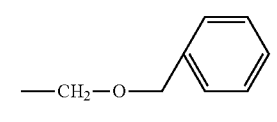
(AL-11)-22 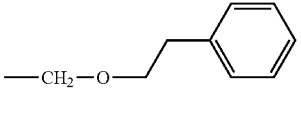
(AL-11)-23 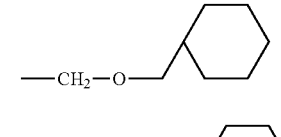
(AL-11)-24 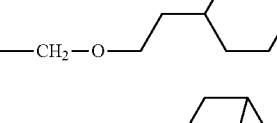
(AL-11)-25 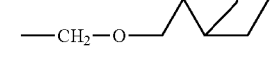
(AL-11)-26 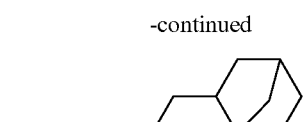
(AL-11)-27 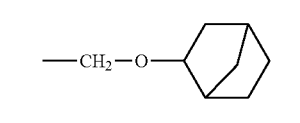
(AL-11)-28 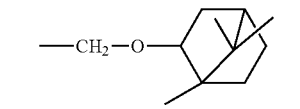
(AL-11)-29 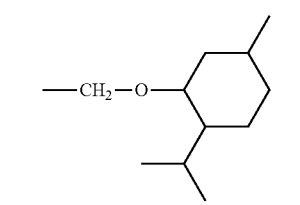
(AL-11)-30 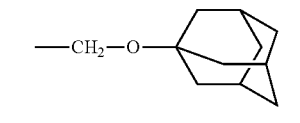
(AL-11)-31 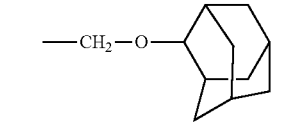
(AL-11)-32 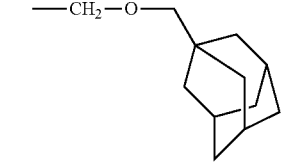
(AL-11)-33 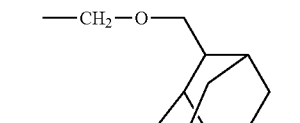
(AL-11)-34 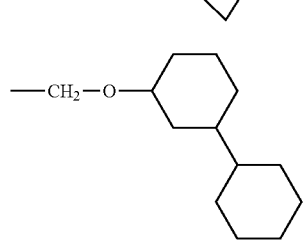
(AL-11)-35 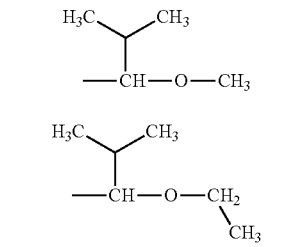
(AL-11)-36 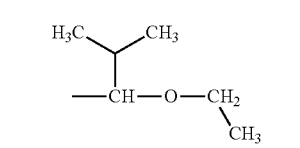

(AL-11)-37 through (AL-11)-57

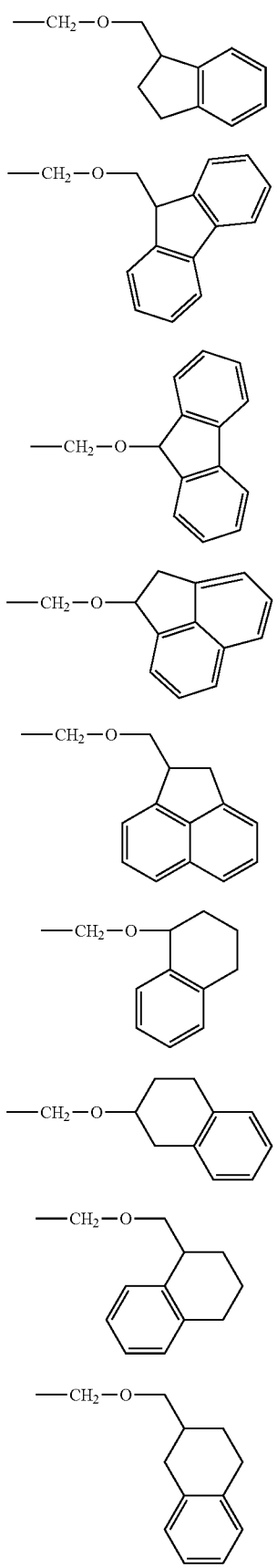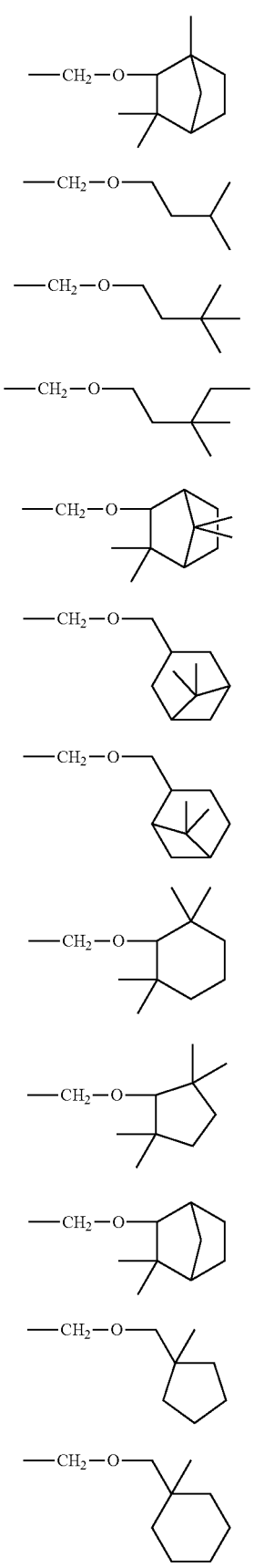

(AL-11)-79 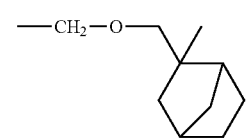
(AL-11)-80 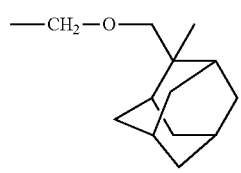
(AL-11)-81 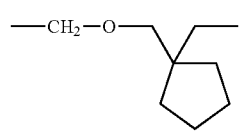
(AL-11)-82 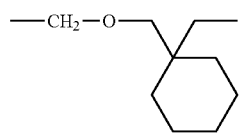
(AL-11)-83 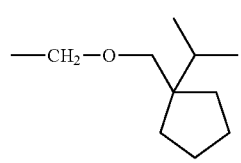
(AL-11)-84 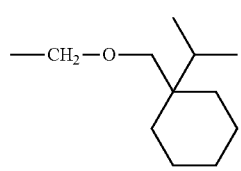
(AL-11)-85 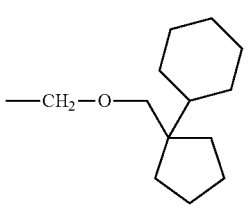
(AL-11)-86 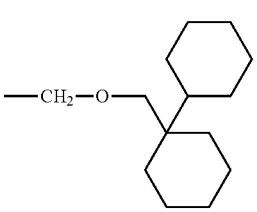
(AL-11)-87 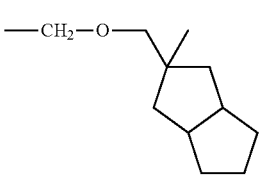
(AL-11)-88 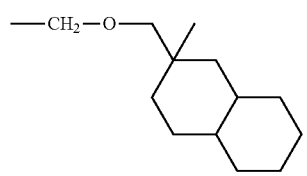
(AL-11)-89 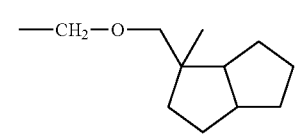
(AL-11)-90 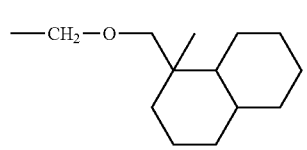
(AL-11)-91 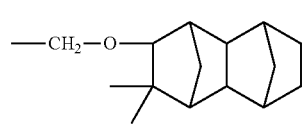
(AL-11)-92 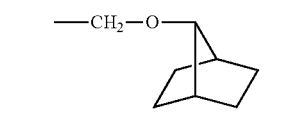
(AL-11)-93 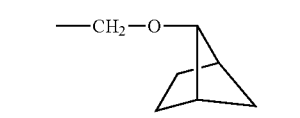
(AL-11)-94 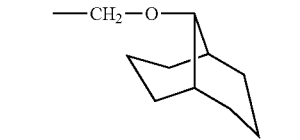
(AL-11)-95 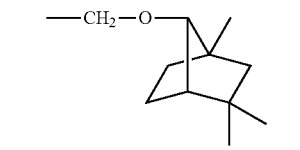
(AL-11)-96 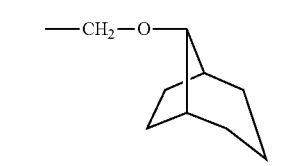
(AL-11)-97 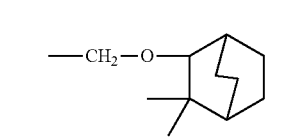
(AL-11)-98 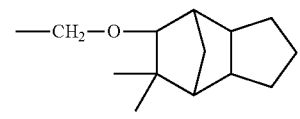

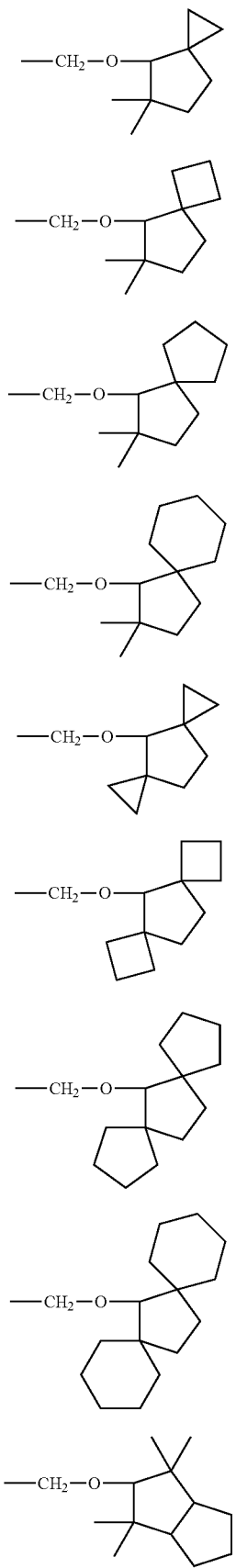

(AL-11)-99
(AL-11)-100
(AL-11)-101
(AL-11)-102
(AL-11)-103
(AL-11)-104
(AL-11)-105
(AL-11)-106
(AL-11)-107

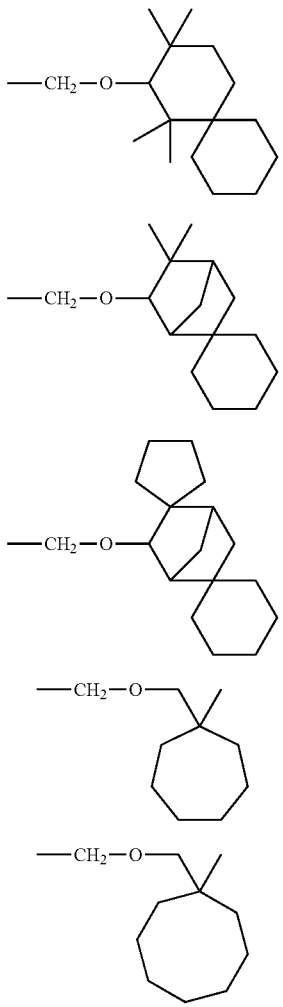

(AL-11)-108
(AL-11)-109
(AL-11)-110
(AL-11)-111
(AL-11)-112

Other examples of acid labile groups include those of the following formula (AL-11a) or (AL-11b) while the polymer may be crosslinked within the molecule or between molecules with these acid labile groups.

$$\begin{array}{c}(AL\text{-}11a)\\ -\underset{R^{62}}{\overset{R^{61}}{\underset{|}{C}}}\!\!\left(\!O\!-\!R^{63}\!\right)_{\!b5}\!O\!-\!A\!\left[\!O\!-\!\left(\!R^{63}\!-\!O\!\right)_{\!d5}\!\underset{R^{62}}{\overset{R^{61}}{\underset{|}{C}}}\!-\!\right]_{\!c5}\end{array}$$

$$\begin{array}{c}(AL\text{-}11b)\\ -\underset{R^{62}}{\overset{R^{61}}{\underset{|}{C}}}\!-\!O\!-\!R^{63}\!-\!B\!-\!A\!\left[\!B\!-\!\left(\!R^{63}\!-\!O\!\right)_{\!d5}\!\underset{R^{62}}{\overset{R^{61}}{\underset{|}{C}}}\!-\!\right]_{\!c5}\end{array}$$

Herein $R^{61}$ and $R^{62}$ each are hydrogen or a straight, branched or cyclic $C_1$-$C_8$ alkyl group, or $R^{61}$ and $R^{62}$ may bond together to form a ring with the carbon atom to which they are attached, and $R^{61}$ and $R^{62}$ are straight or branched $C_1$-$C_8$ alkylene groups when they form a ring. $R^{63}$ is a straight, branched or cyclic $C_1$-$C_{10}$ alkylene group. Each of b5 and d5 is 0 or an integer of 1 to 10, preferably 0 or an integer of 1 to 5, and c5 is an integer of 1 to 7. "A" is a (c5+1)-valent aliphatic or alicyclic saturated hydrocarbon group, aromatic hydrocarbon group or heterocyclic group having 1 to 50 carbon atoms, which may be separated by a heteroatom such as oxygen, sulfur or nitrogen or in which some hydrogen atoms attached to carbon atoms may be substituted by hydroxyl, carboxyl, carbonyl radicals or fluorine atoms. "B" is —CO—O—, —NHCO—O— or —NHCONH—.

Preferably, "A" is selected from divalent to tetravalent, straight, branched or cyclic $C_1$-$C_{20}$ alkylene, alkanetriyl and alkanetetrayl groups, and $C_6$-$C_{30}$ arylene groups, which may be separated by a heteroatom such as oxygen, sulfur or nitrogen or in which some hydrogen atoms attached to carbon atoms may be substituted by hydroxyl, carboxyl, acyl radicals or halogen atoms. The subscript c5 is preferably an integer of 1 to 3.

The crosslinking acetal groups of formulae (AL-11a) and (AL-11b) are exemplified by the following formulae (AL-11)-113 through (AL-11)-120.

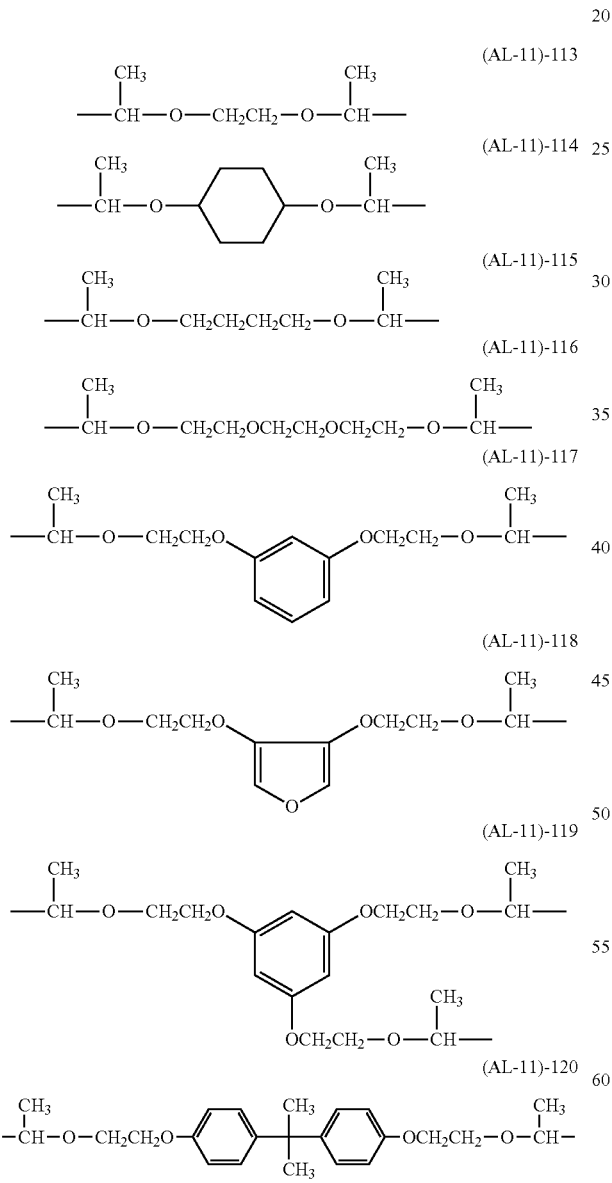

Illustrative examples of the tertiary alkyl group of formula (AL-12) include tert-butyl, triethylcarbyl, 1-ethylnorbornyl, 1-methylcyclohexyl, 1-ethylcyclopentyl, and tert-amyl groups as well as those of (AL-12)-1 to (AL-12)-16.

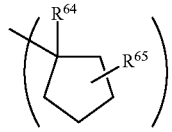
(AL-12)-1

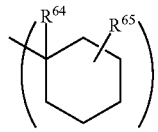
(AL-12)-2

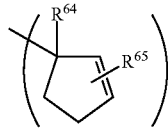
(AL-12)-3

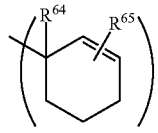
(AL-12)-4

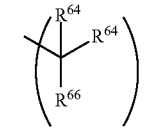
(AL-12)-5

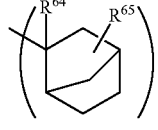
(AL-12)-6

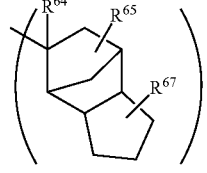
(AL-12)-7

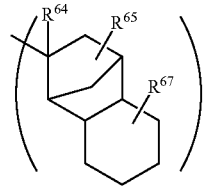
(AL-12)-8

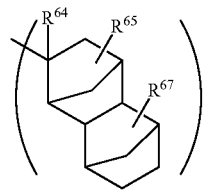
(AL-12)-9

-continued (AL-12)-10
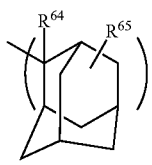

(AL-12)-11
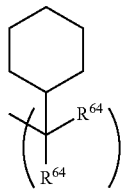

(AL-12)-12
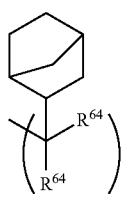

(AL-12)-13
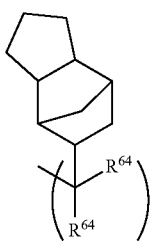

(AL-12)-14
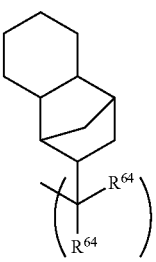

(AL-12)-15
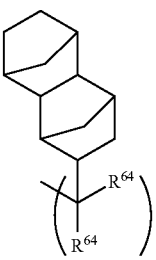

(AL-12)-16
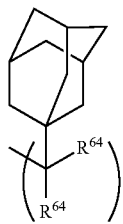

Herein $R^{64}$ is each independently a straight, branched or cyclic $C_1$-$C_8$ alkyl group, $C_6$-$C_{20}$ aryl group or $C_7$-$C_{20}$ aralkyl group, or two $R^{64}$ groups may bond together to form a ring. R65 and $R^{67}$ each are hydrogen, methyl or ethyl. $R^{66}$ is a $C_6$-$C_{20}$ aryl group or $C_7$-$C_{20}$ aralkyl group.

With acid labile groups containing $R^{68}$ representative of a di- or poly-valent alkylene or arylene group as shown by formula (AL-12)-17, the polymer may be crosslinked within the molecule or between molecules. In formula (AL-12)-17, $R^{64}$ is as defined above, $R^{68}$ is a single bond, a straight, branched or cyclic $C_1$-$C_{20}$ alkylene group or arylene group, which may contain a heteroatom such as oxygen, sulfur or nitrogen, and b6 is an integer of 0 to 3. It is noted that formula (AL-12)-17 is applicable to all the foregoing acid labile groups.

(AL-12)-17
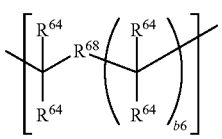

The groups represented by $R^{64}$, $R^{65}$, $R^{66}$ and $R^{67}$ may contain a heteroatom such as oxygen, nitrogen or sulfur. Such groups are exemplified by those of the following formulae (AL-13)-1 to (AL-13)-7.

(AL-13)-1
—(CH$_2$)$_4$OH (AL-13)-2
—(CH$_2$)$_2$O(CH$_2$)$_3$CH$_3$ (AL-13)-3
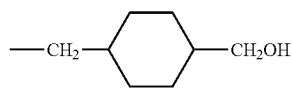

(AL-13)-4
—(CH$_2$)$_2$O(CH$_2$)$_2$OH (AL-13)-5
—(CH$_2$)$_6$OH (AL-13)-6
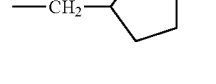

(AL-13)-7
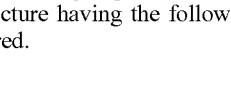

Of the acid labile groups of formula (AL-12), groups of exo-form structure having the following formula (AL-12)-19 are preferred.

(AL-12)-19
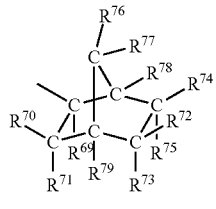

Herein $R^{69}$ is a straight, branched or cyclic $C_1$-$C_8$ alkyl group or optionally substituted $C_6$-$C_{20}$ aryl group. $R^{70}$ to $R^{75}$, $R^{78}$, and $R^{79}$ are each independently hydrogen or a monovalent $C_1$-$C_{15}$ hydrocarbon group, typically alkyl, which may contain a heteroatom, $R^{76}$ and $R^{77}$ are hydrogen; or a pair of $R^{70}$ and $R^{71}$, $R^{72}$ and $R^{74}$, $R^{72}$ and $R^{75}$, $R^{73}$ and $R^{75}$, $R^{73}$ and $R^{79}$, $R^{74}$ and $R^{78}$, $R^{76}$ and $R^{77}$, or $R^{77}$ and $R^{78}$ may bond together to form a ring, typically aliphatic ring, with the carbon atom to which they are attached, and in this case, the ring-forming participant is a divalent $C_1$-$C_{15}$ hydrocarbon group, typically alkylene, which may contain a heteroatom. Also, a pair of $R^{70}$ and $R^{79}$, $R^{76}$ and $R^{79}$, or $R^{72}$ and $R^{74}$ which are attached to vicinal carbon atoms may bond together directly to form a double bond. The formula also represents an enantiomer.

The ester form monomers from which recurring units having an exo-form structure represented by the formula (AL-12)-19 shown below are derived are described in U.S. Pat. No. 6,448,420 (JP-A 2000-327633).

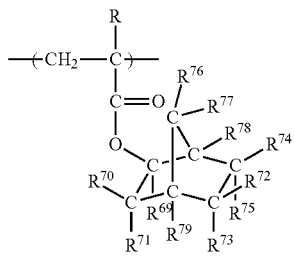

Herein R is hydrogen or methyl, $R^{69}$ to $R^{79}$ are as defined above. Illustrative non-limiting examples of suitable monomers are given below.

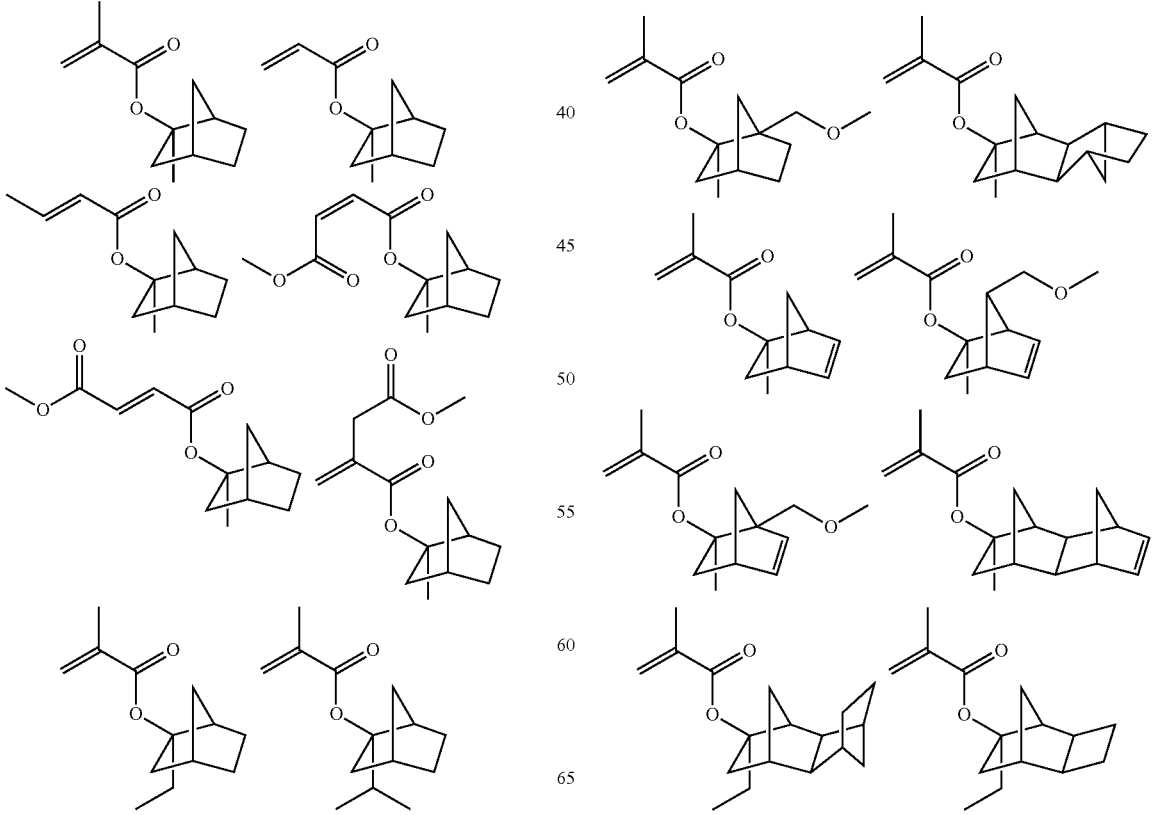
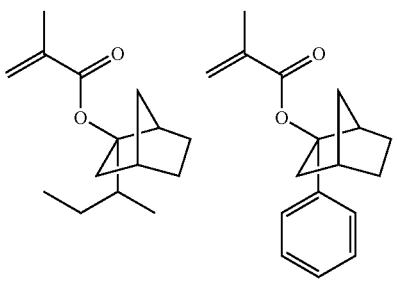
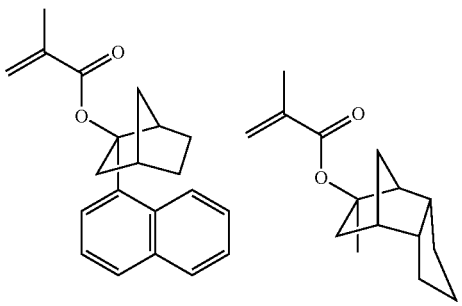
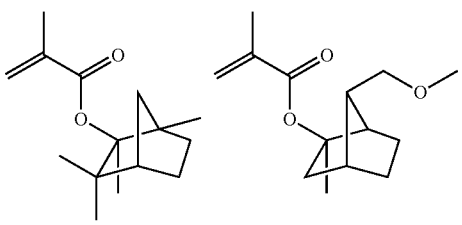
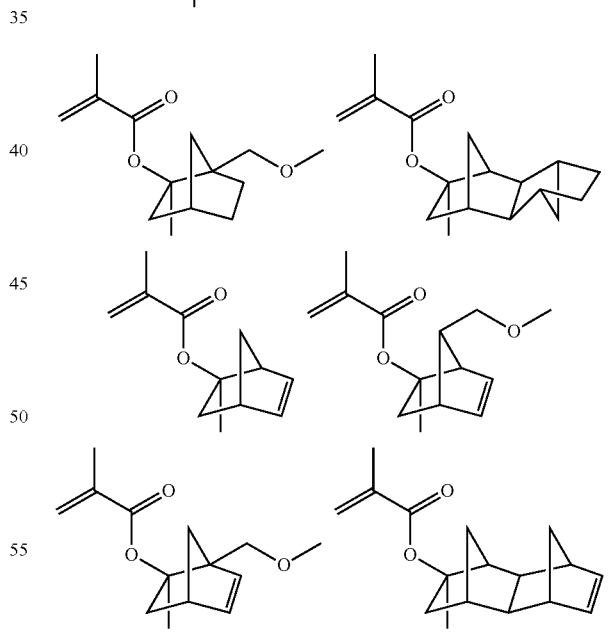

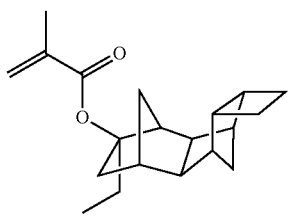

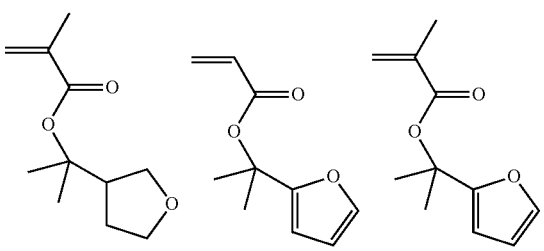

Also included in the acid labile groups of formula (AL-12) are acid labile groups having furandiyl, tetrahydrofurandiyl or oxanorbornanediyl as represented by the following formula (AL-12)-20.

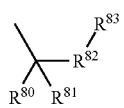 (AL-12)-20

Herein, $R^{80}$ and $R^{81}$ are each independently a monovalent hydrocarbon group, typically a straight, branched or cyclic $C_1$-$C_{10}$ alkyl group. $R^{80}$ and $R^{81}$, taken together, may form an aliphatic hydrocarbon ring of 3 to 20 carbon atoms with the carbon atom to which they are attached. $R^{82}$ is a divalent group selected from furandiyl, tetrahydrofurandiyl and oxanorbornanediyl. $R^{83}$ is hydrogen or a monovalent hydrocarbon group, typically a straight, branched or cyclic $C_1$-$C_{10}$ alkyl group, which may contain a heteroatom.

Recurring units substituted with an acid labile group having furandiyl, tetrahydrofurandiyl or oxanorbornanediyl as represented by the formula:

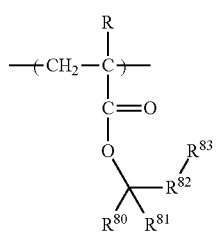

(wherein R, $R^{80}$ to $R^{83}$ are as defined above) are derived from monomers, examples of which are shown below. Note that Me is methyl and Ac is acetyl.

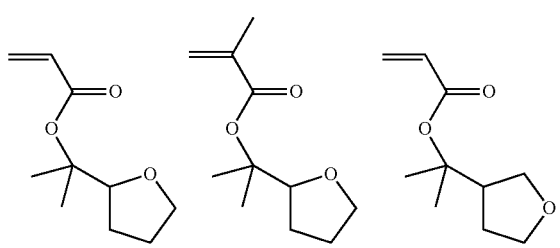

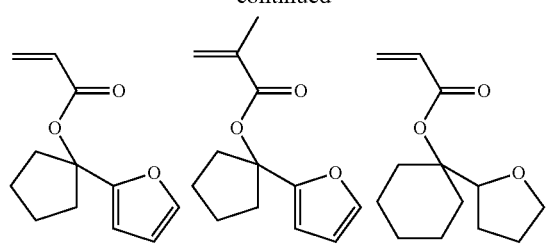
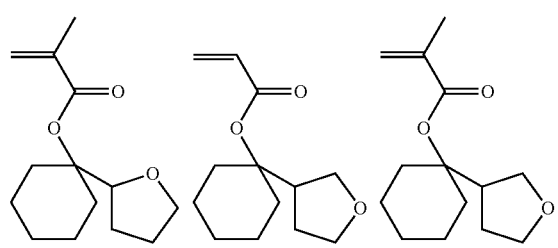
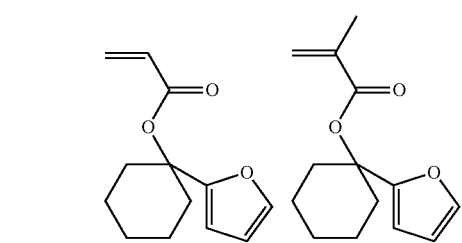
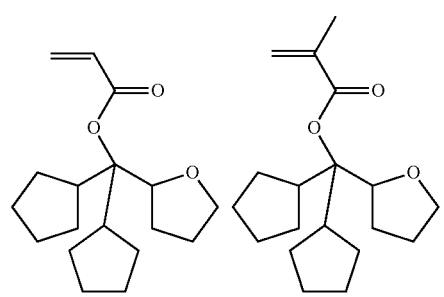
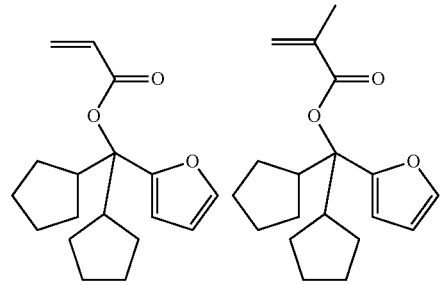
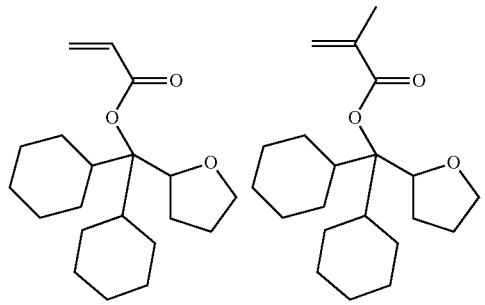
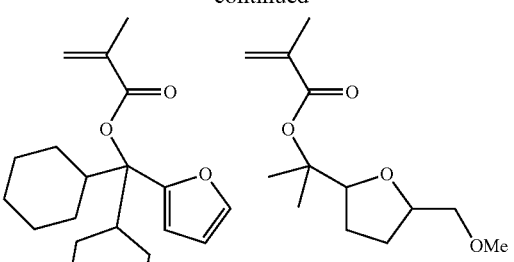
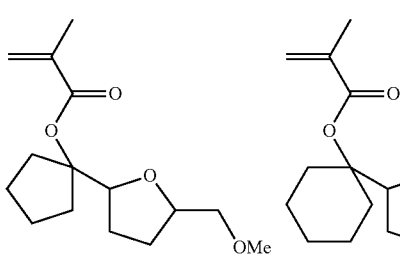
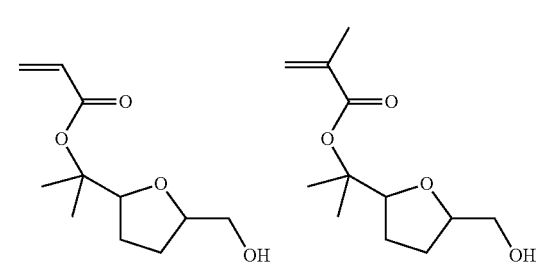
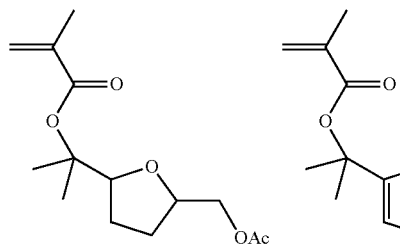
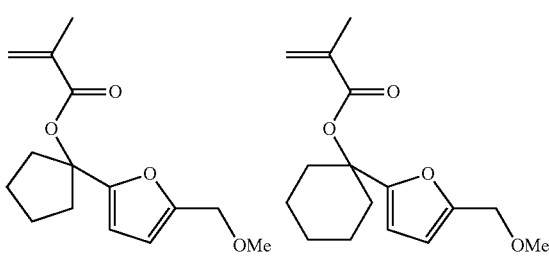
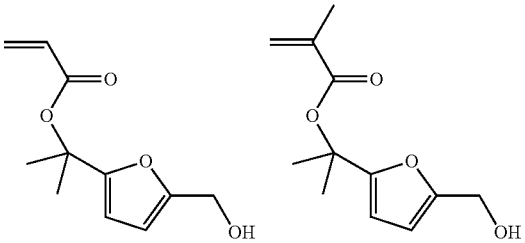

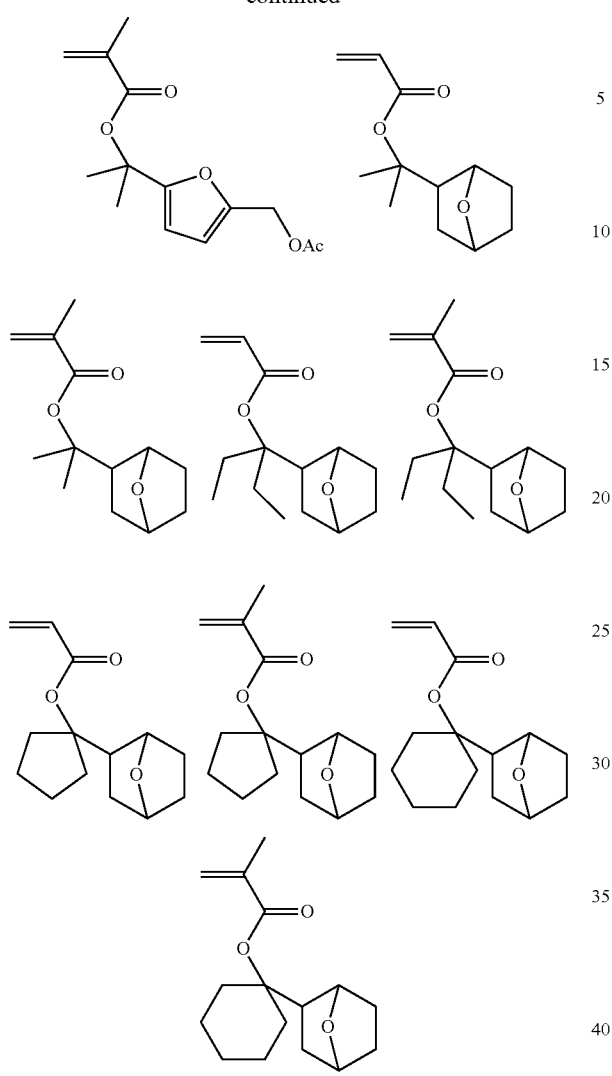
Of the acid labile groups of tertiary alkyl form having formula (A1-12), those acid labile groups having a branched alkyl directly attached to the ring offer high solubility in organic solvents. Such acid labile groups are exemplified below. In the following formula, the line segment protruding out of the bracket denotes a valence bond.
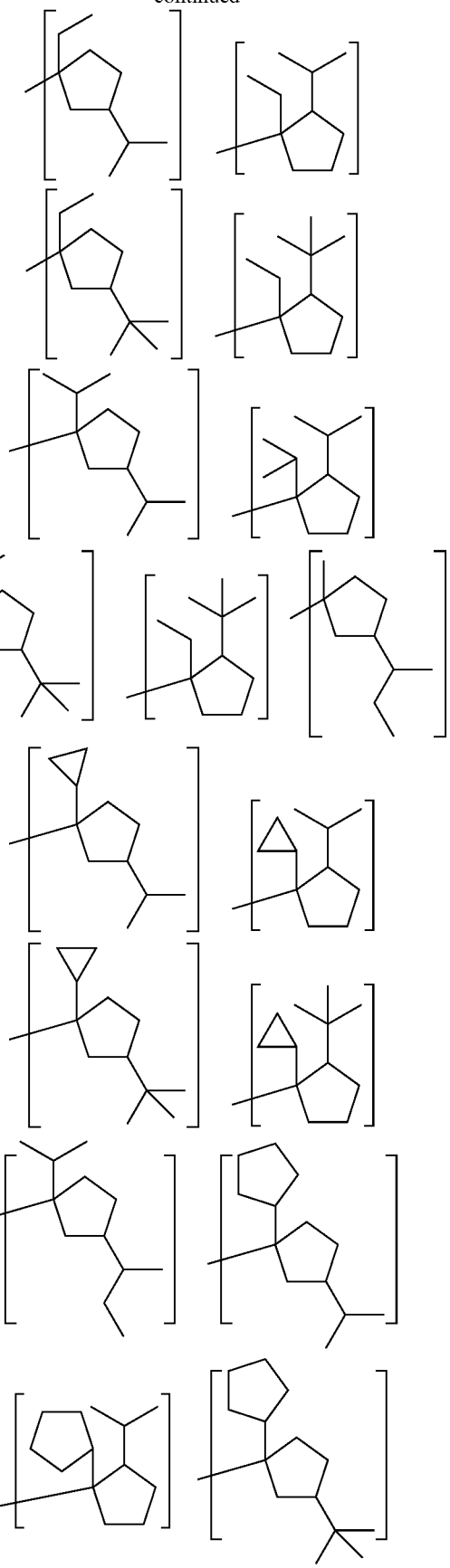

-continued

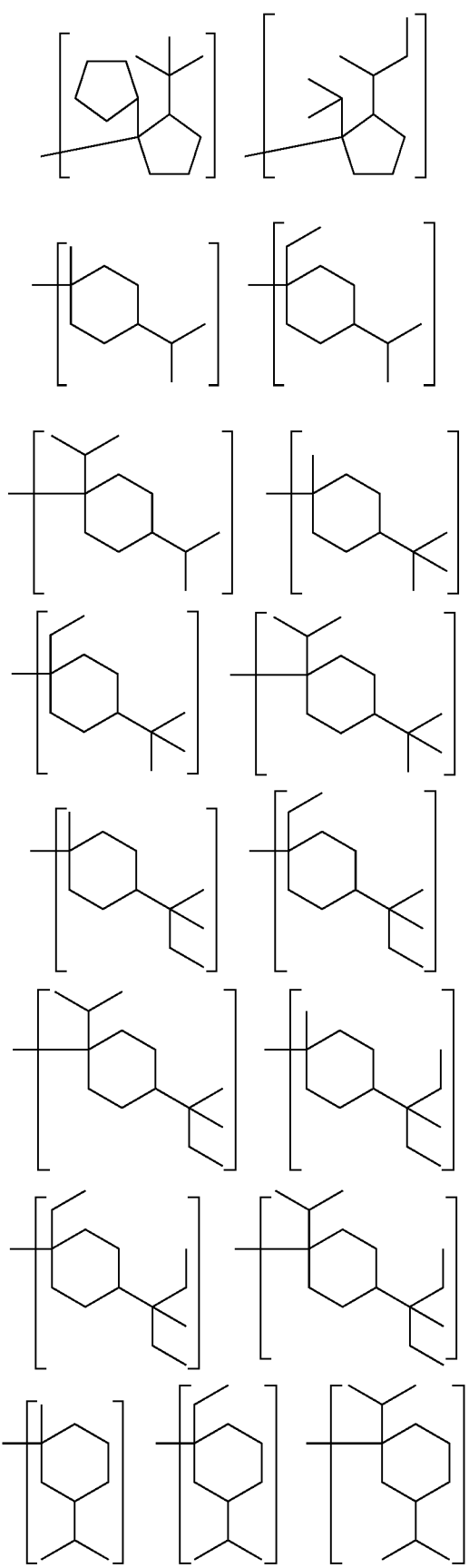

-continued

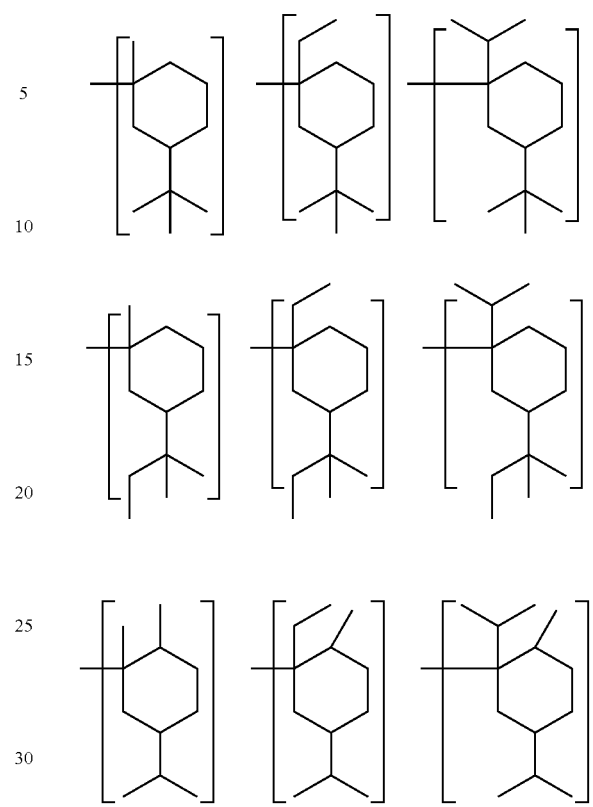

While the preferred polymer used as the base resin in the positive resist composition comprises essentially recurring units (a1) of (meth)acrylate, styrenecarboxylate or vinyl-naphthalenecarboxylate substituted with an acid labile group or units (a2) of hydroxystyrene substituted with an acid labile group, it may have further copolymerized therein recurring units (b) having a phenolic hydroxyl group as an adhesive group. Examples of the monomer from which recurring units (b) having a phenolic hydroxyl group are derived are given below.

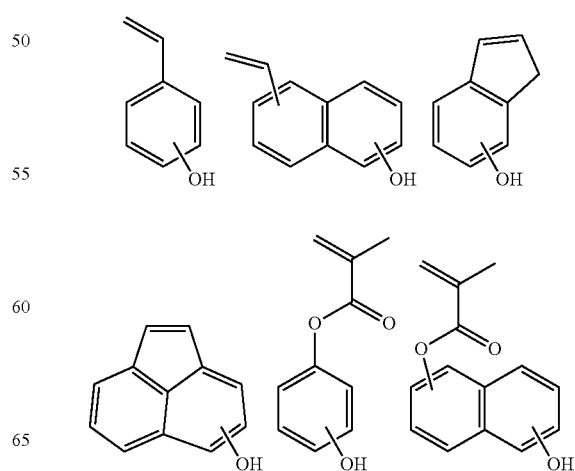

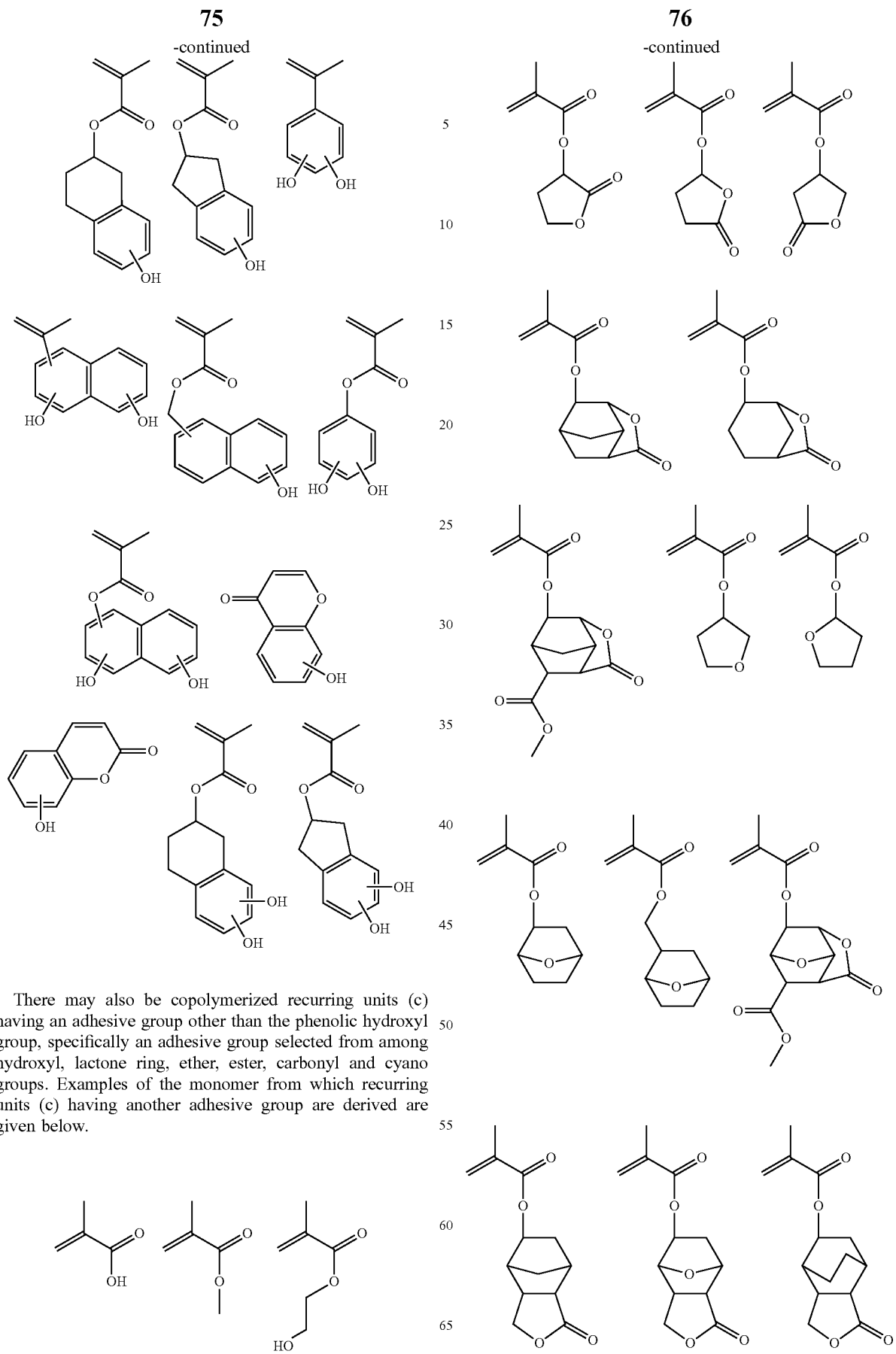
There may also be copolymerized recurring units (c) having an adhesive group other than the phenolic hydroxyl group, specifically an adhesive group selected from among hydroxyl, lactone ring, ether, ester, carbonyl and cyano groups. Examples of the monomer from which recurring units (c) having another adhesive group are derived are given below.

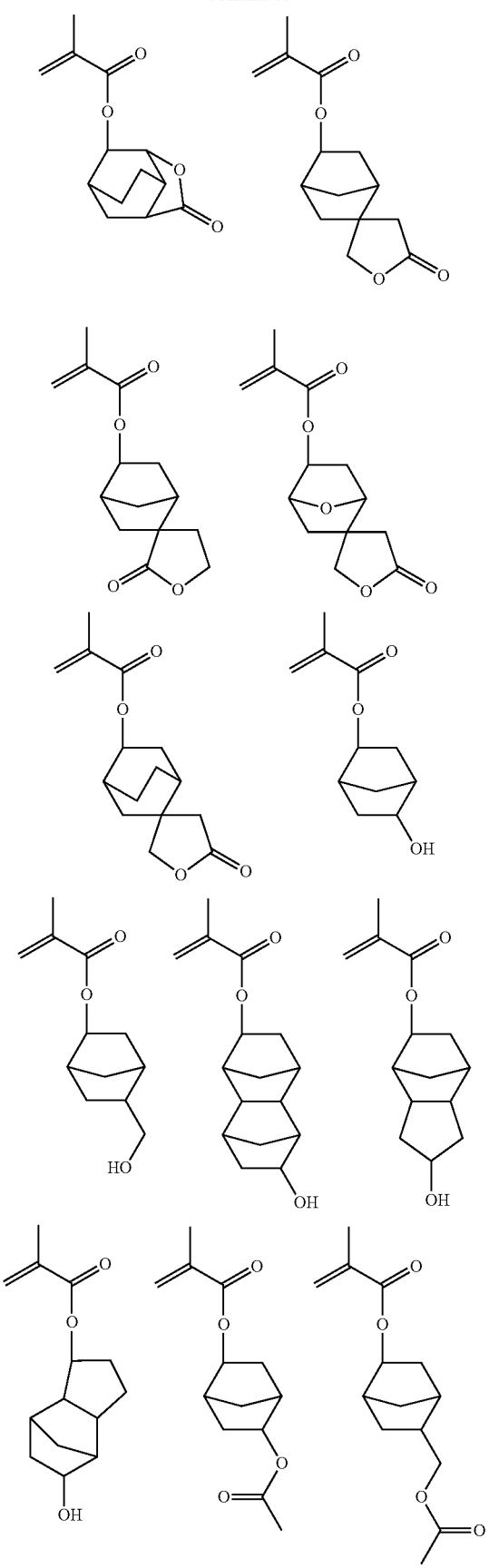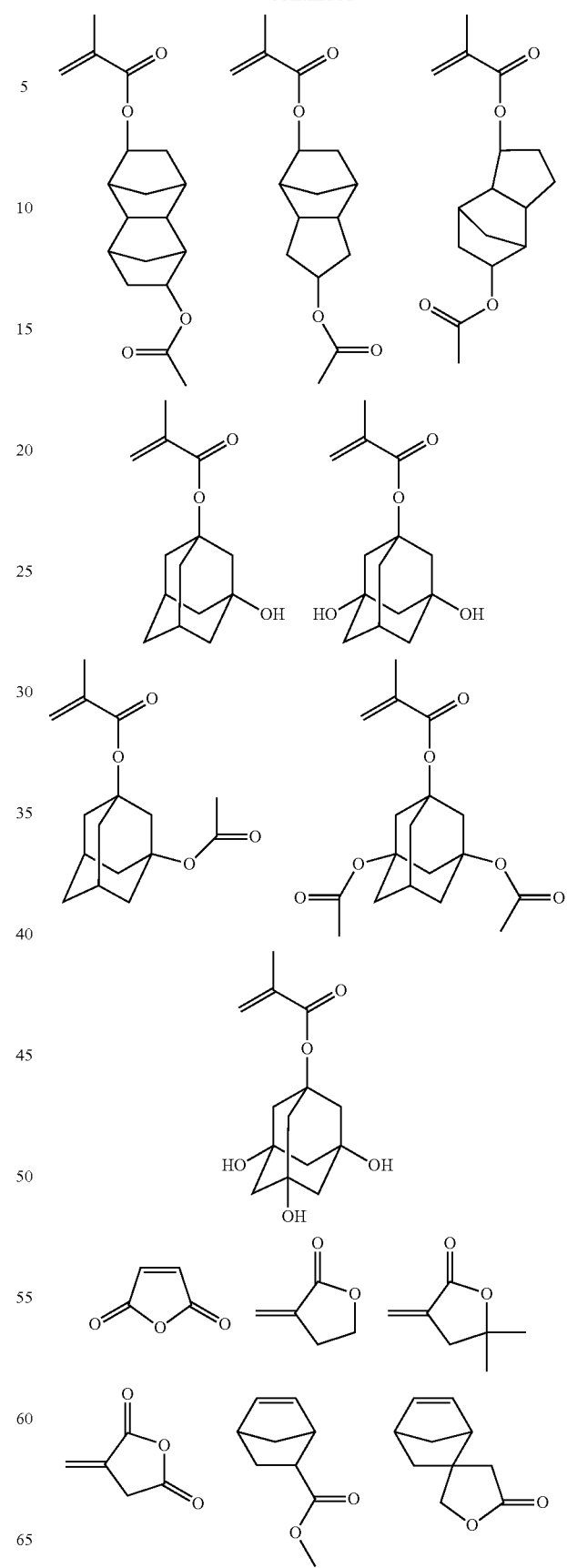

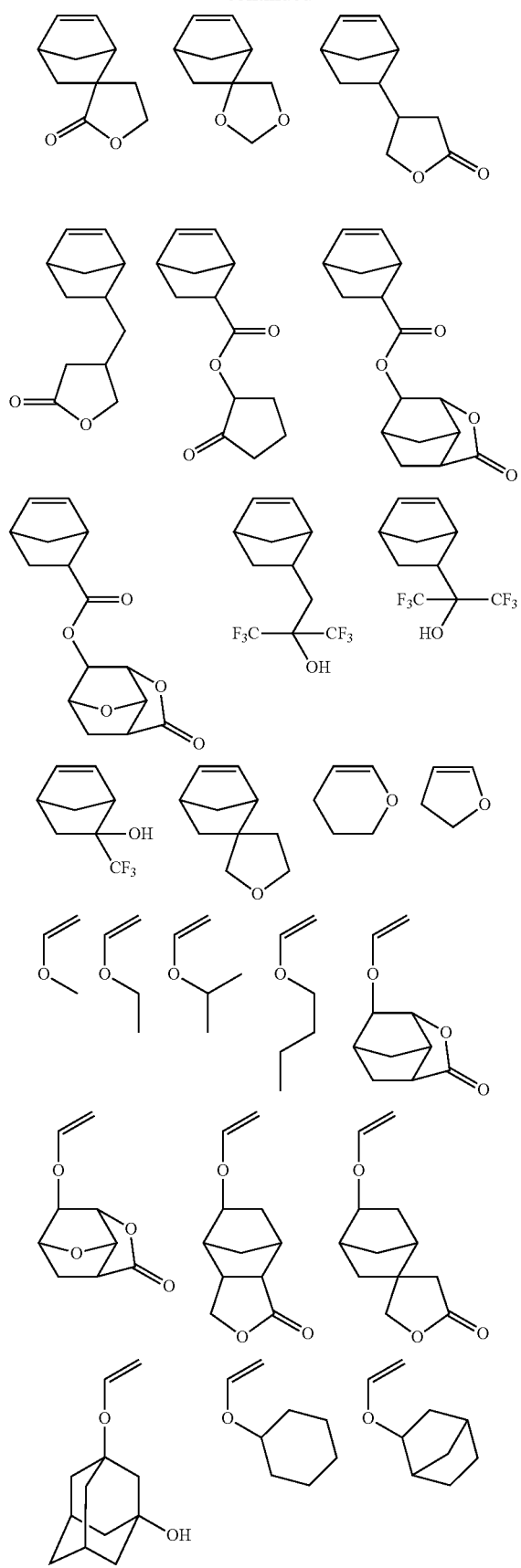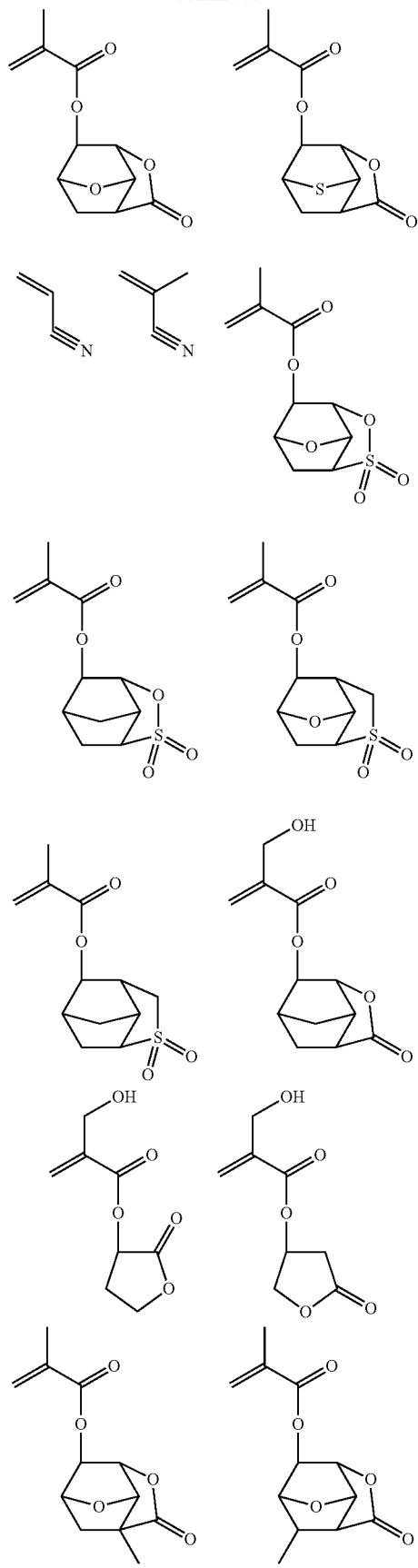

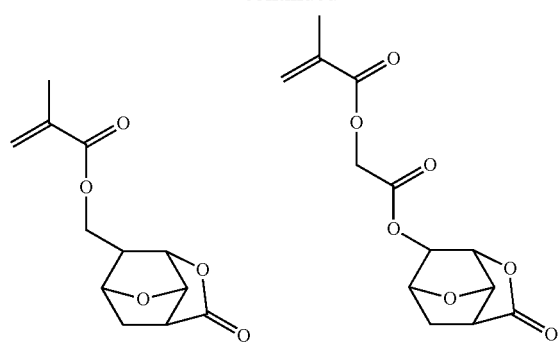
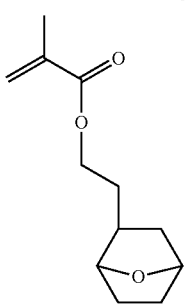
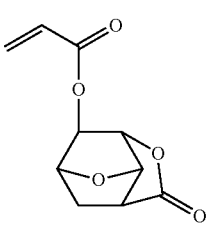
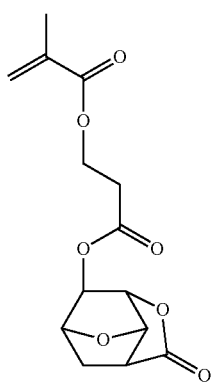
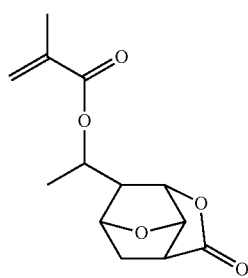
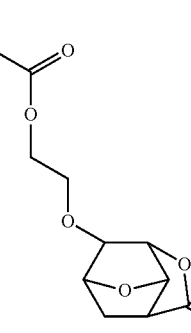
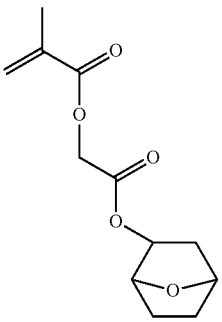
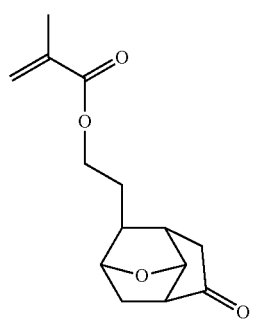
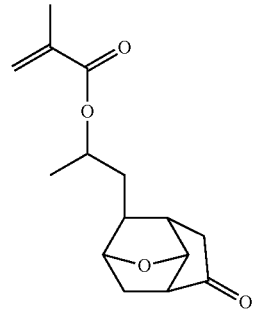
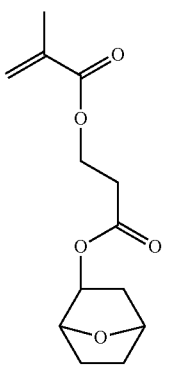
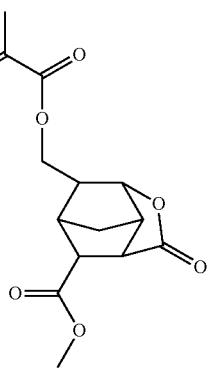
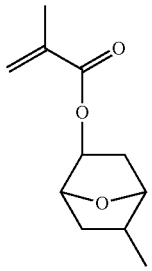
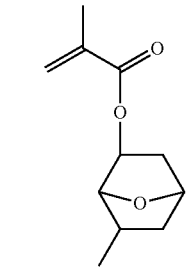
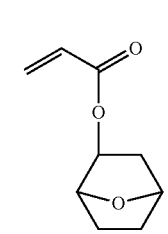
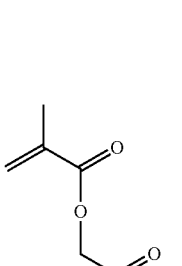
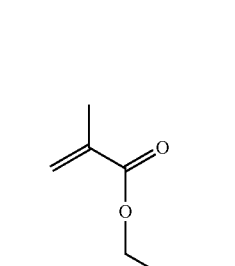
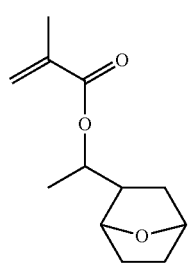
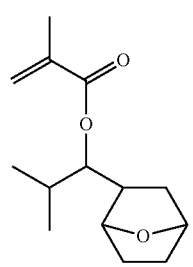
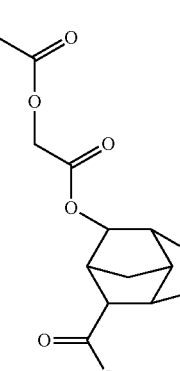
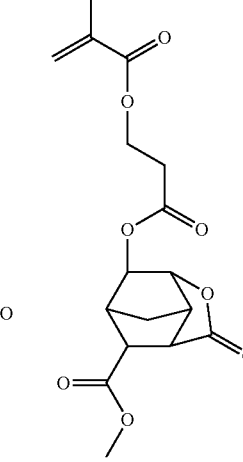

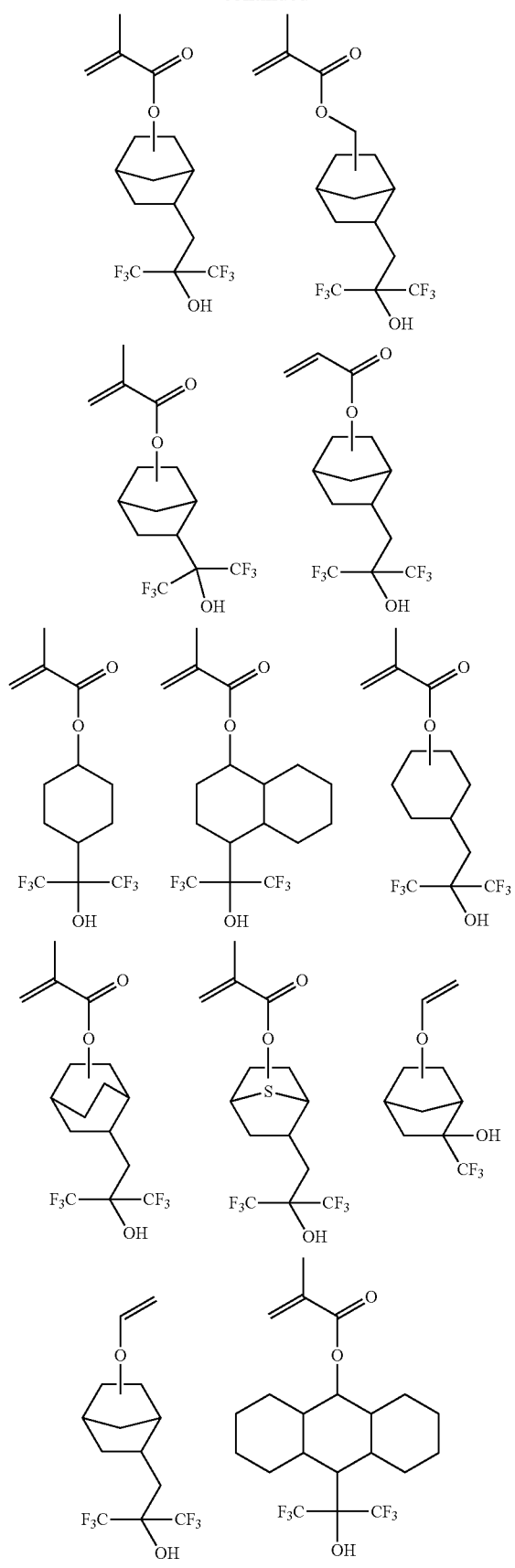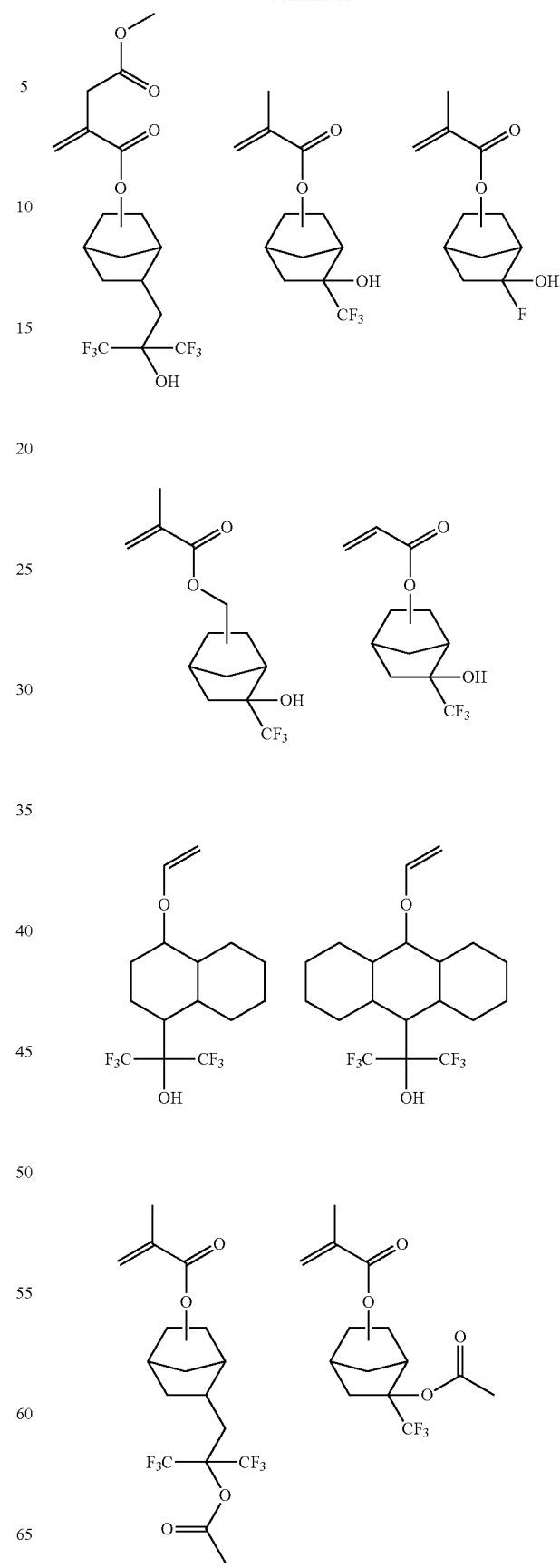

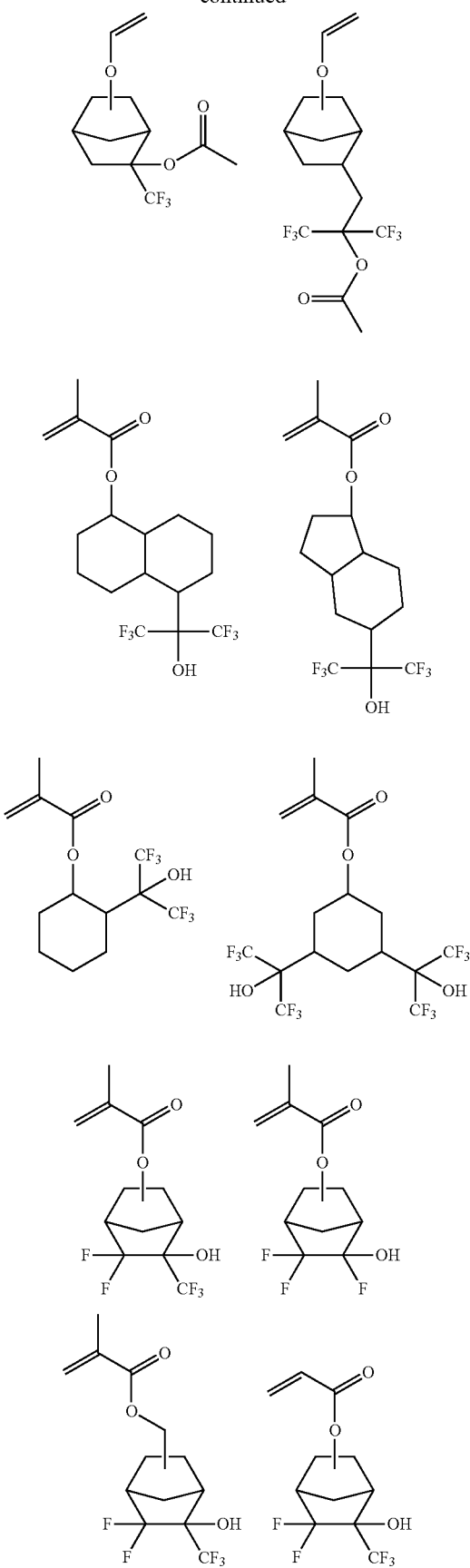
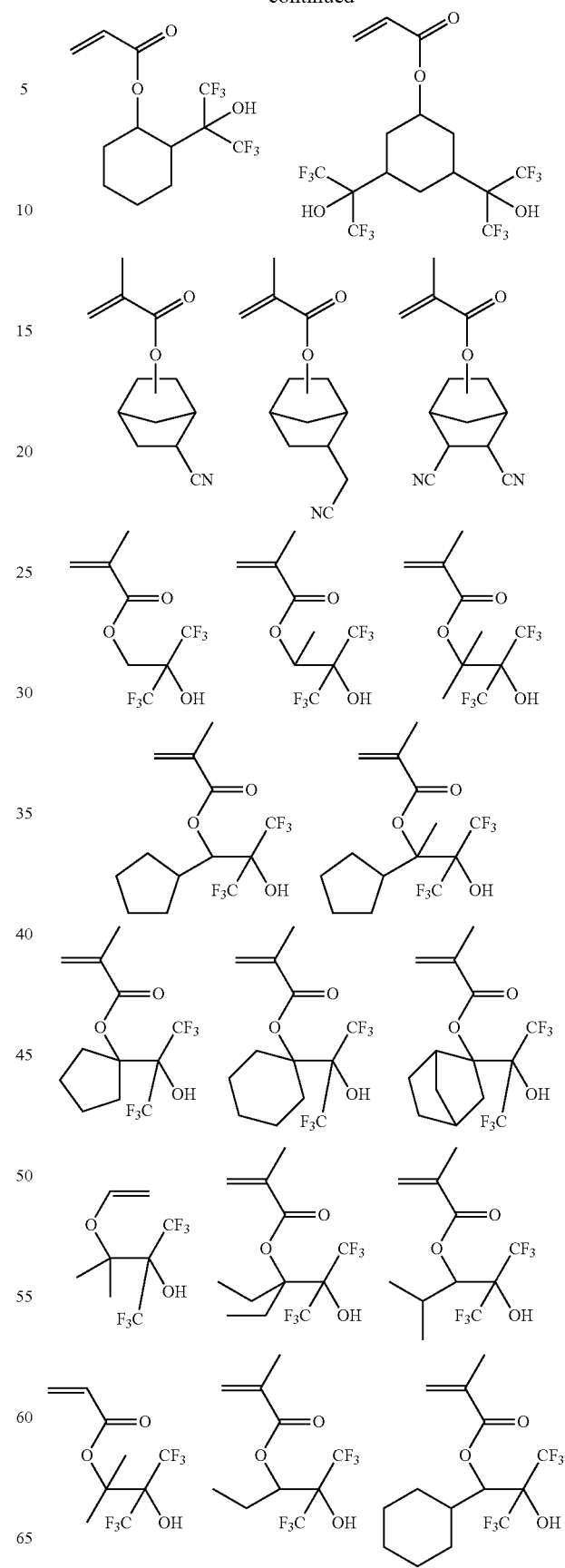

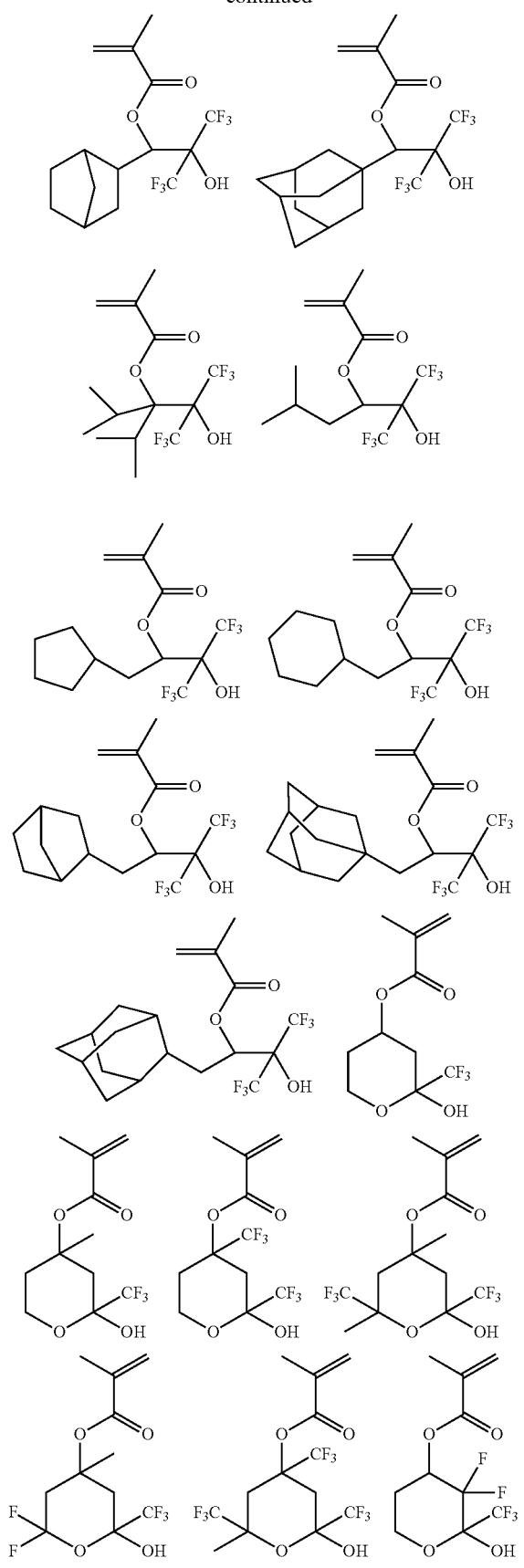
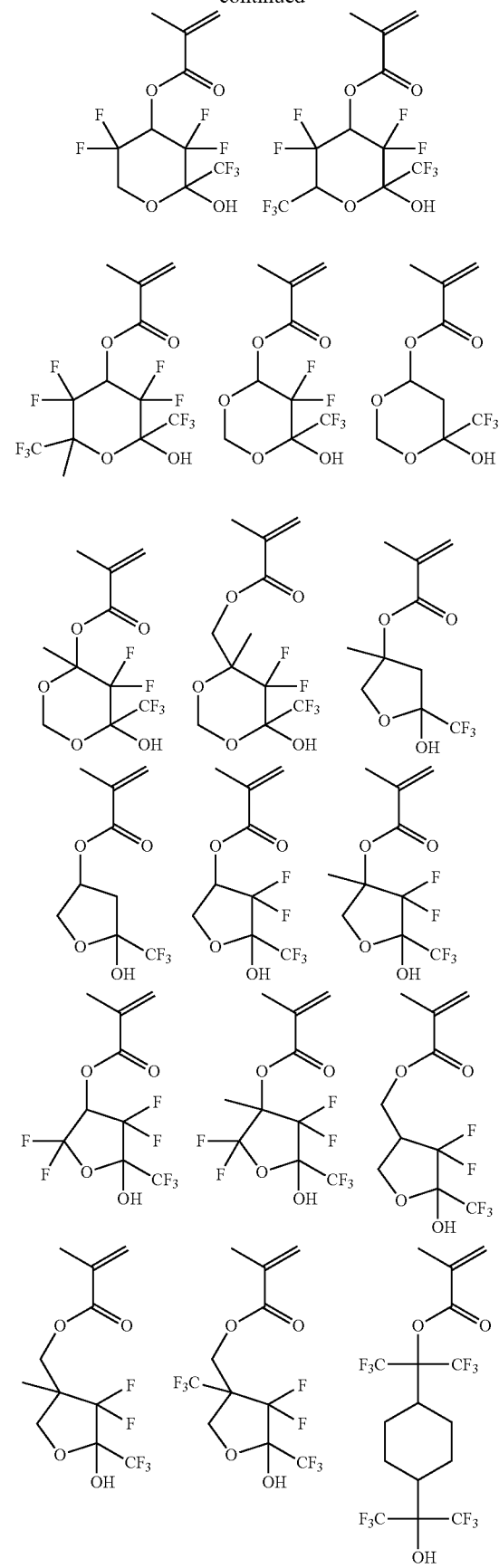

-continued
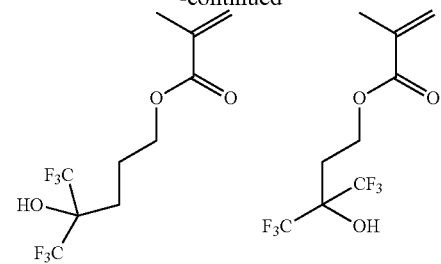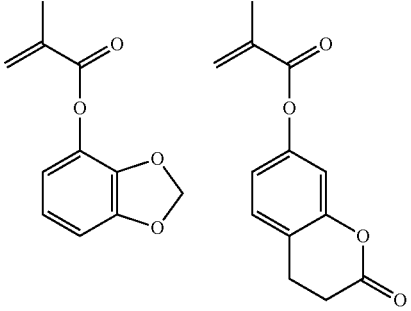
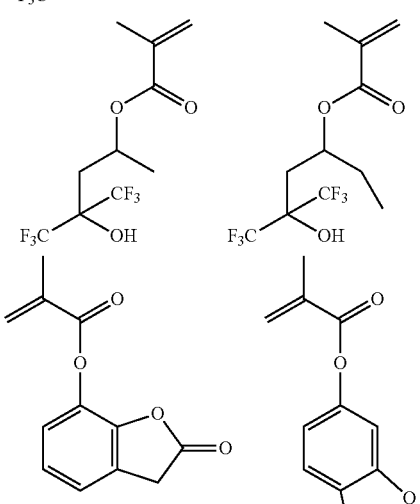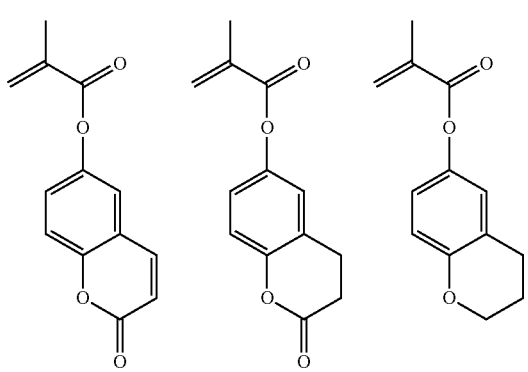
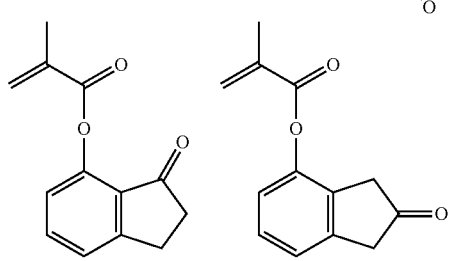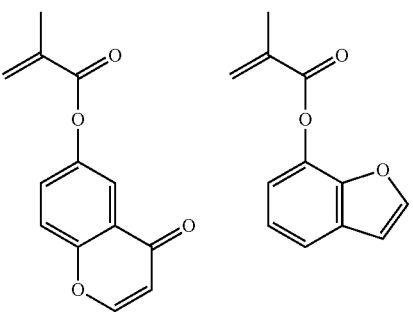
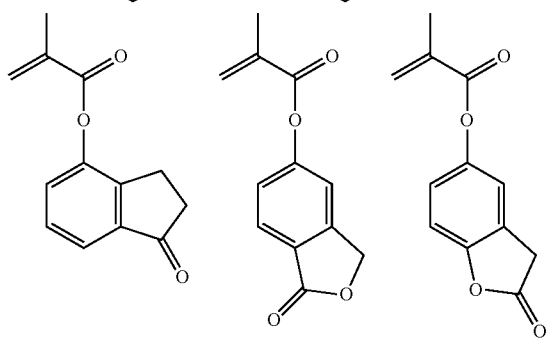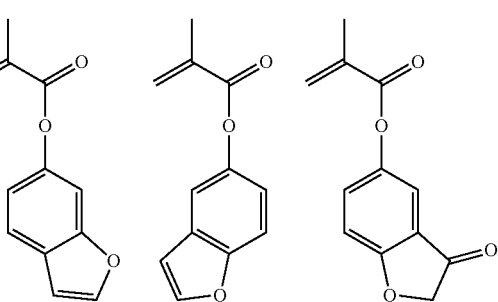
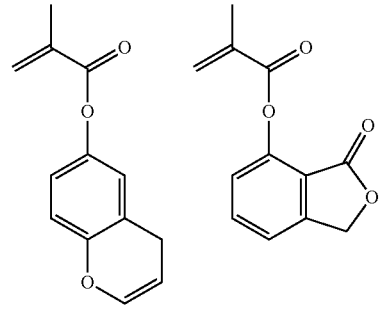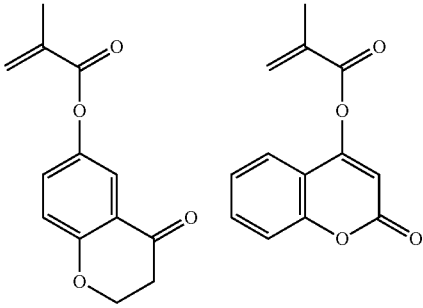

91
-continued
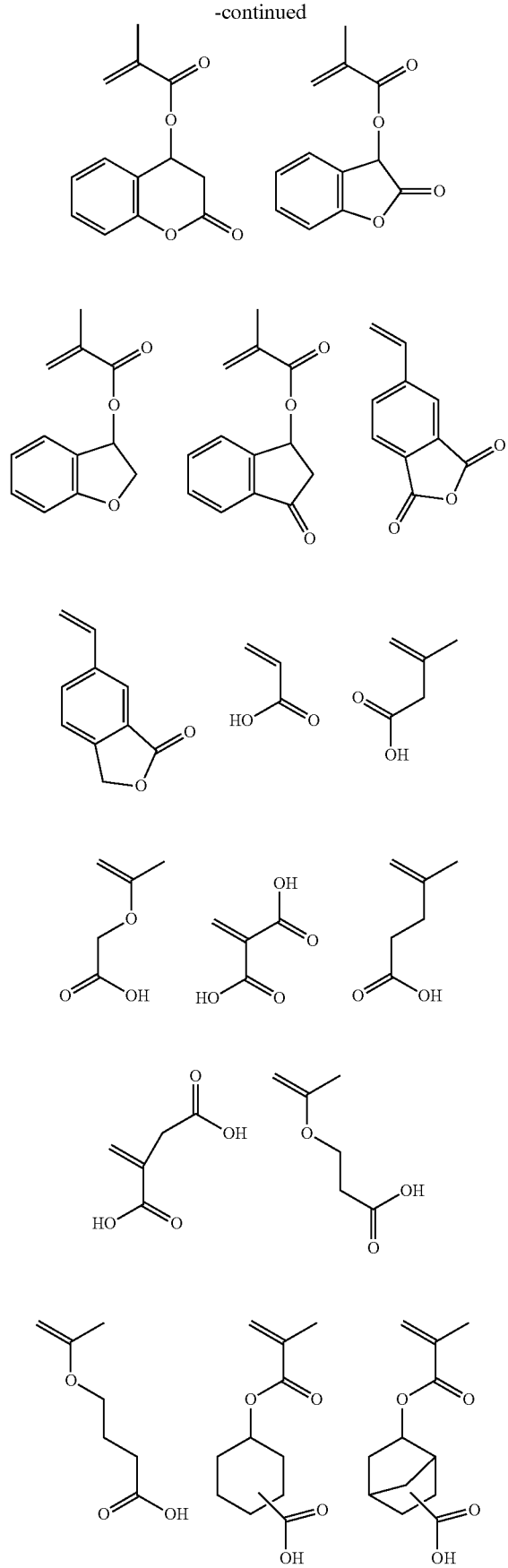
92
-continued
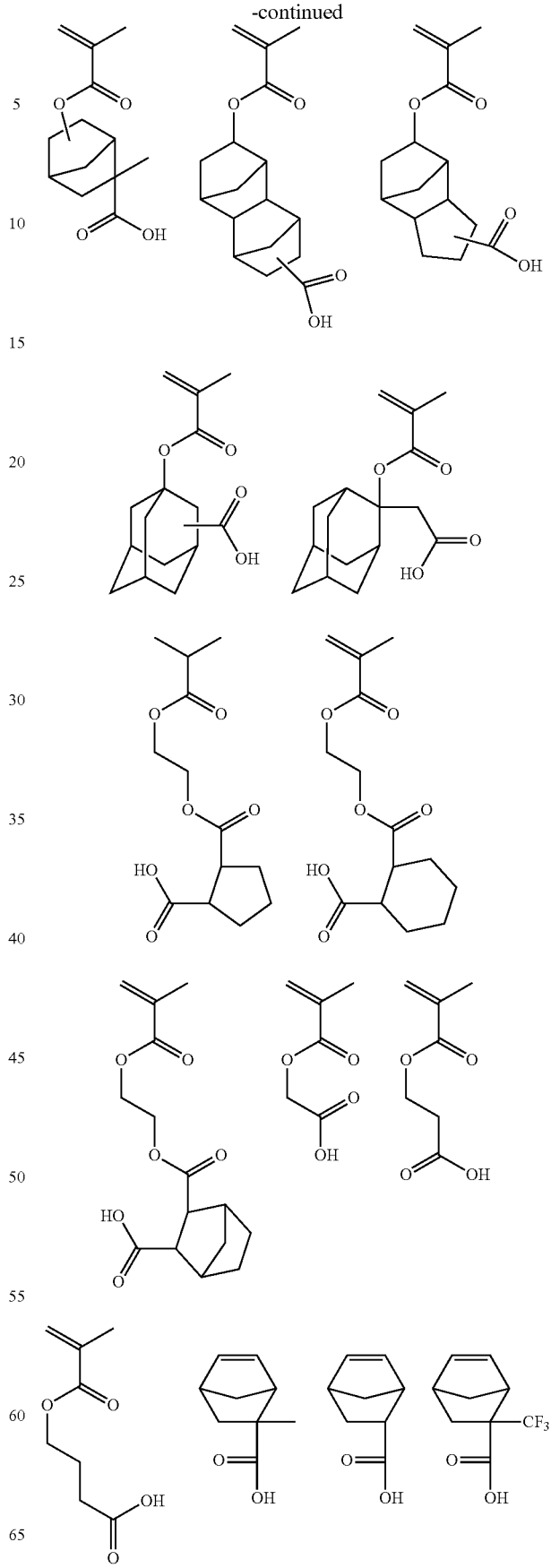

-continued

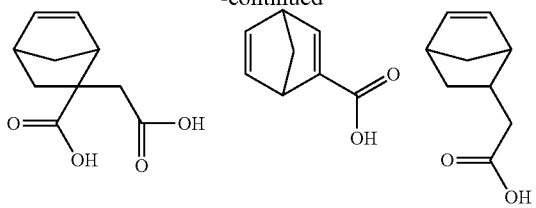

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

In the polymer, recurring units (d) of indene, benzofuran, benzothiophene, acenaphthylene, chromone, coumarin, norbornadiene, and derivatives thereof, may be copolymerized. Such monomers are exemplified below.

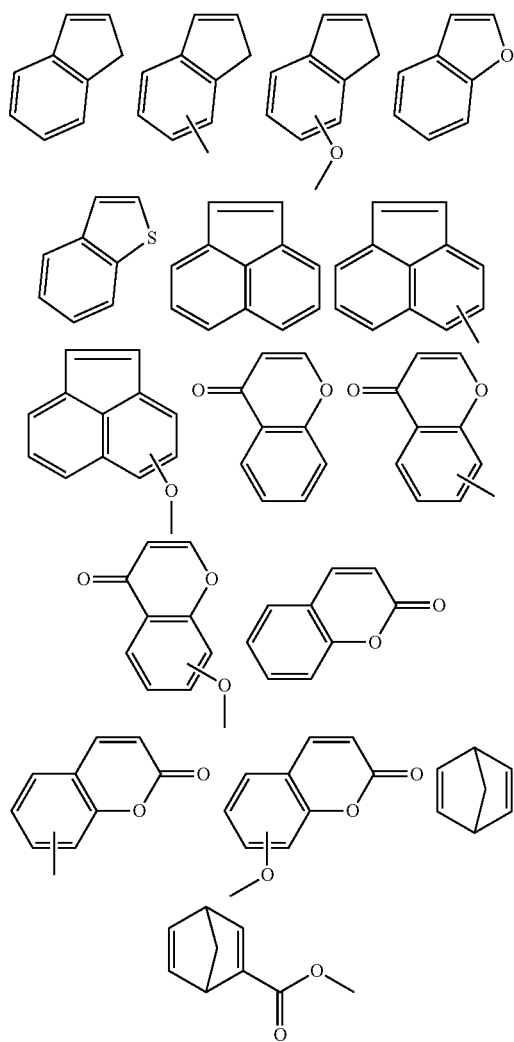

Besides the recurring units described above, further recurring units (e) can be copolymerized, examples of which include styrene, vinylnaphthalene, vinylanthracene, vinylpyrene, methyleneindane, vinylpyridine, and vinylcarbazole.

In a further embodiment, an acid generator (f) in the form of an onium salt having polymerizable olefin may be copolymerized with the foregoing monomers. JP-A 2005-084365 discloses sulfonium salts having polymerizable olefin capable of generating a sulfonic acid and similar iodonium salts. JP-A 2006-178317 discloses a sulfonium salt having sulfonic acid directly attached to the main chain.

In this embodiment, the polymer may have further copolymerized therein recurring units having a sulfonium salt (f1) to (f3) represented by the general formula (3).

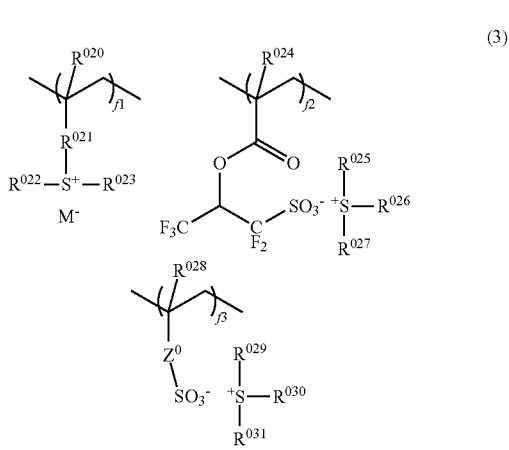

(3)

Herein $R^{020}$, $R^{024}$ and $R^{028}$ each are hydrogen or methyl. $R^{021}$ is phenylene, —O—$R^0$—, or —C(=O)—$Y^0$—$R^0$— wherein $Y^0$ is oxygen or NH and $R^0$ is a straight, branched or cyclic $C_1$-$C_6$ alkylene group, alkenylene group or phenylene group, which may contain a carbonyl (—CO—), ester (—COO—), ether (—O—) or hydroxyl moiety. $R^{022}$, $R^{023}$, $R^{025}$, $R^{026}$, $R^{027}$, $R^{029}$, $R^{030}$, and $R^{031}$ are each independently a straight, branched or cyclic $C_1$-$C_{12}$ alkyl group which may contain a carbonyl, ester or ether moiety, or a $C_6$-$C_{12}$ aryl group, $C_7$-$C_{20}$ aralkyl group, or thiophenyl group. $Z^0$ is a single bond, methylene, ethylene, phenylene, fluorinated phenylene, —O—$R^{032}$—, or —C(=O)—$Z^1$—$R^{032}$— wherein $Z^1$ is oxygen or NH and $R^{032}$ is a straight, branched or cyclic $C_1$-$C_6$ alkylene, alkenylene or phenylene group which may contain a carbonyl, ester, ether or hydroxyl moiety. M is a non-nucleophilic counter ion, and f1, f2 and f3 are in the range: $0 \leq f1 \leq 0.5$, $0 \leq f2 \leq 0.5$, $0 \leq f3 \leq 0.5$, and $0 \leq f1+f2+f3 \leq 0.5$.

Examples of the non-nucleophilic counter ion M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Also included are sulfonates having fluorine substituted at α-position as represented by the general formula (K-1) and sulfonates having fluorine substituted at α- and β-positions as represented by the general formula (K-2).

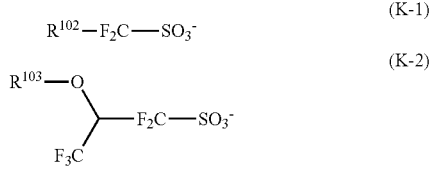

(K-1)

(K-2)

In formula (K-1), $R^{102}$ is hydrogen, or a straight, branched or cyclic $C_1$-$C_{20}$ alkyl group, $C_2$-$C_{20}$ alkenyl group, or $C_6$-$C_{20}$ aryl group, which may have an ether, ester, carbonyl moiety, lactone ring, or fluorine atom. In formula (K-2), $R^{103}$ is hydrogen, or a straight, branched or cyclic $C_1$-$C_{30}$ alkyl or acyl group, $C_2$-$C_{20}$ alkenyl group, or $C_6$-$C_{20}$ aryl or aryloxy group, which may have an ether, ester, carbonyl moiety or lactone ring.

Onium salts such as sulfonium salts, iodonium salts and ammonium salts of sulfonic acids which are not fluorinated at α-position as described in US 2008153030 (JP-A 2008-158339) and similar onium salts of carboxylic acid may also be used as the quencher. While an α-fluorinated sulfonic acid, imidic acid, and methidic acid are necessary to deprotect the acid labile group of carboxylic acid ester, an α-non-fluorinated sulfonic acid and a carboxylic acid are released by salt exchange with an α-non-fluorinated onium salt. An α-non-fluorinated sulfonic acid and a carboxylic acid function as a quencher because they do not induce deprotection reaction. In particular, since sulfonium salts and iodonium salts of an α-non-fluorinated sulfonic acid and a carboxylic acid are photodegradable, those portions receiving a high light intensity are reduced in quenching capability and increased in the concentration of a α-fluorinated sulfonic acid, imidic acid, or methidic acid. As a result, the exposed portions are improved in contrast. When a negative tone pattern is formed using an organic solvent, the improvement in the contrast of exposed portions leads to an improvement in the rectangularity of negative pattern. Onium salts including sulfonium salts, iodonium salts and ammonium salts of an α-non-fluorinated sulfonic acid and a carboxylic acid are highly effective in controlling the diffusion of an α-fluorinated sulfonic acid, imidic acid and methidic acid. This is because the onium salt resulting from salt exchange is less mobile due to a higher molecular weight. In the event that a hole pattern is formed by negative tone development, since acid is generated in many regions, it is very important to control the diffusion of acid from the exposed area to the unexposed area. The addition of onium salts including sulfonium salts, iodonium salts and ammonium salts of an α-non-fluorinated sulfonic acid and a carboxylic acid as well as the basic compound defined herein is very important from the aspect of acid diffusion control.

The attachment of an acid generator to the polymer main chain is effective in restraining acid diffusion, thereby preventing a reduction of resolution due to blur by acid diffusion. Also roughness (LER or LWR) is improved since the acid generator is uniformly distributed.

The base polymer for formulating the positive resist composition comprises recurring units (a1) and/or (a2) having an acid labile group as essential components and additional recurring units (b), (c), (d), (e), (f1), (f2) and/or (f3) as optional components. A copolymerization proportion of units (a1), (a2), (b), (c), (d), (e), (f1), (f2) and (f3) is: $0 \le a1<1.0$, $0 \le a2<1.0$, $0<a1+a2<1.0$, $0 \le b<1.0$, $0 \le c<1.0$, $0<b+c<1.0$, $0 \le d \le 0.8$, $0 \le e \le 0.8$, $0 \le f1 \le 0.5$, $0<f2 \le 0.5$, $0 \le f3 \le 0.5$, and $0 \le f1+f2+f3 \le 0.5$;

preferably $0 \le a1 \le 0.9$, $0 \le a2 \le 0.9$, $0.1 \le a1+a2 \le 0.9$, $0 \le b \le 0.9$, $0 \le c \le 0.9$, $0.1 \le b+c \le 0.9$, $0 \le d \le 0.7$, $0 \le e \le 0.7$, $0 \le f1 \le 0.4$, $0 \le f2 \le 0.4$, $0 \le f3 \le 0.4$, and $0 \le f1+f2+f3 \le 0.4$; and more preferably $0 \le a1 \le 0.8$, $0 \le a2 \le 0.8$, $0.2 \le a1+a2 \le 0.8$, $0 \le b \le 0.8$, $0 \le c \le 0.8$, $0.2 \le b+c \le 0.8$, $0 \le d \le 0.6$, $0 \le e \le 0.6$, $0 \le f1 \le 0.3$, $0 \le f2 \le 0.3$, $0 \le f3 \le 0.3$, and $0 \le f1+f2+f3 \le 0.3$. Note a1+a2+b+c+d+e+f1+f2+f3=1.0.

For the base polymer for formulating the negative resist composition, an acid labile group is not necessarily essential. The base polymer comprises recurring units (b), (c), (d), (e), (f1), (f2) and (f3) in a copolymerization proportion: $0<b \le 1.0$, $0 \le c<1.0$, $0 \le d \le 0.8$, $0 \le e \le 0.8$, $0 \le f1 \le 0.5$, $0 \le f2 \le 0.5$, $0 \le f3 \le 0.5$, and $0 \le f1+f2+f3 \le 0.5$;

preferably $0.2 \le b \le 1.0$, $0 \le c \le 0.8$, $0 \le d \le 0.7$, $0 \le e \le 0.7$, $0 \le f1 \le 0.4$, $0 \le f2 \le 0.4$, $0 \le f3 \le 0.4$, and $0 \le f1+f2+f3 \le 0.4$; and more preferably $0.3 \le b \le 1.0$, $0 \le c \le 0.75$, $0 \le d \le 0.6$, $0 \le e \le 0.6$, $0 \le f1 \le 0.3$, $0 \le f2 \le 0.3$, $0 \le f3 \le 0.3$, and $0 \le f1+f2+f3 \le 0.3$. Note b+c+d+e+f1+f2+f3=1.0.

These polymers may be synthesized by any desired methods, for example, by dissolving one or more monomers selected from the monomers to form the recurring units (a1), (a2), (b), (c), (d), (e), (f1), (f2) and (f3) in an organic solvent, adding a radical polymerization initiator thereto, and effecting heat polymerization. Examples of the organic solvent which can be used for polymerization include toluene, benzene, tetrahydrofuran, diethyl ether and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis as mentioned above, for thereby converting the polymer product to polyhydroxystyrene or hydroxypolyvinylnaphthalene. For alkaline hydrolysis, a base such as aqueous ammonia or triethylamine may be used. The reaction temperature is −20° C. to 100° C., preferably 0° C. to 60° C., and the reaction time is 0.2 to 100 hours, preferably 0.5 to 20 hours.

The polymer used in the resist composition should preferably have a weight average molecular weight (Mw) in the range of 1,000 to 500,000, and more preferably 2,000 to 30,000, as measured by GPC versus polystyrene standards using tetrahydrofuran as a solvent. With too low a Mw, the resist composition may become less heat resistant. A polymer with too high a Mw may lose alkaline solubility and give rise to a footing phenomenon after pattern formation.

If a multi-component polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the multi-component copolymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, molecular weight or dispersity is acceptable.

The basic compound of formula (1)-1 or (1)-2 is advantageously used in a chemically amplified positive or negative resist composition having an acid generator added thereto. Specifically, the basic compound is added to the polymer serving as a base resin, which may be further combined with any desired components including an organic solvent, dissolution inhibitor, surfactant, crosslinker and the like to formulate a positive or negative resist composition. This positive or negative resist composition has a very high sensitivity in that the dissolution rate in developer of the polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when an acid generator is incorporated to formulate a chemically amplified positive resist composition capable of utilizing acid catalyzed reaction, the composition has a higher sensitivity and is further improved in the properties described above.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

Any conventional basic compounds may be added along with the basic compound of formula (1)-1 or (1)-2 for further suppressing the diffusion rate of acid in the resist film or correcting the pattern profile. Addition of a surfactant may improve or control the coating characteristics of the resist composition.

Suitable conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146] to [0164], and compounds having a carbamate group as described in JP 3790649.

The positive or negative resist composition may include an acid generator in order for the composition to function as a chemically amplified positive or negative resist composition in the pattern forming process defined herein. Typical of the acid generator used herein is a photoacid generator (PAG) capable of generating an acid in response to actinic light or radiation. It is any compound capable of generating an acid upon exposure to high-energy radiation. Suitable PAGs include sulfonium salts, iodonium salts, sulfonyldiazomethane, N-sulfonyloxyimide, and oxime-O-sulfonate acid generators. The acid generators may be used alone or in admixture of two or more. Exemplary acid generators are described in U.S. Pat. No. 7,537,880 (JP-A 2008-111103, paragraphs [0122] to [0142]).

While the resist composition of the invention should comprise the base polymer, the basic compound of formula (1)-1 and/or (1)-2, and the acid generator, described above, it may further comprise an organic solvent, dissolution inhibitor, crosslinker, surfactant, acetylene alcohol, and conventional basic compound, alone or in combination.

Examples of the organic solvent used herein are described in JP-A 2008-111103, paragraphs [0144] to [0145] (U.S. Pat. No. 7,537,880). Exemplary solvents include ketones such as cyclohexanone, cyclopentanone and methyl-2-n-amylketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; and lactones such as γ-butyrolactone, which may be used alone or in admixture. Exemplary surfactants are described in JP-A 2008-111103, paragraphs [0165] to [0166]. The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a weight average molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in US 2008090172 (JP-A 2008-122932, paragraphs [0155] to [0178]). Suitable acetylene alcohols are described in JP-A 2008-122932, paragraphs [0179] to [0182].

Suitable crosslinkers which can be used herein include melamine compounds, guanamine compounds, glycoluril compounds and urea compounds having substituted thereon at least one group selected from among methylol, alkoxymethyl and acyloxymethyl groups, epoxy compounds, isocyanate compounds, azide compounds, and compounds having a double bond such as an alkenyl ether group. These compounds may be used as an additive or introduced into a polymer side chain as a pendant. Hydroxy-containing compounds may also be used as the crosslinker. Of the foregoing crosslinkers, examples of suitable epoxy compounds include tris(2,3-epoxypropyl)isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film loss of resist pattern or rounding of pattern top.

In preferred embodiments, the respective components are used in the following amounts, provided that all amounts are expressed in parts by weight relative to 100 parts by weight of the base polymer. An amount of the PAG used is 0.1 to 50 parts, and more preferably 1 to 40 parts. An amount of the organic solvent used is 100 to 10,000 parts, and more preferably 200 to 8,000 parts. In positive resist compositions, an amount of the dissolution inhibitor blended is 0 to 50 parts, and more preferably 5 to 40 parts. In negative resist compositions, an amount of the crosslinker blended is 0.1 to 50 parts, and more preferably 1 to 40 parts. An amount of the surfactant blended is 0.0001 to 10 parts. An amount of the acetylene alcohol blended is 0 to 5 parts. An amount of the conventional basic compound other than the basic compounds of formulae (1)-1 and (1)-2 is 0 to 5 parts, and more preferably 0 to 4 parts. An amount of the polymeric quencher is 0 to 5 parts, and more preferably 0 to 4 parts.

Process

The positive resist composition, typically chemically amplified positive resist composition comprising a base polymer, a basic compound of formula (1)-1 and/or (1)-2, and an acid generator in an organic solvent is used in the fabrication of various integrated circuits. Pattern formation using the resist composition may be performed by well-known lithography processes. The process generally involves coating, prebaking, exposure, post-exposure baking (PEB), and development. If necessary, any additional steps may be added.

The positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, MoSi, or $SiO_2$) by a suitable coating technique such as spin coating, roll coating, flow coating, dipping, spraying or doctor coating. The coating is prebaked on a hot plate at a temperature of 60 to 150° C. for 10 seconds to 30 minutes, preferably 80 to 120° C. for 30 seconds to 20 minutes. The resulting resist film is generally 0.1 to 2.0 μm thick. The resist film is then exposed to a desired pattern of high-energy radiation such as UV, deep-UV, EB, x-ray, excimer laser light, γ-ray, synchrotron radiation or EUV (soft x-ray), directly or through a mask. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $\mu C/cm^2$. The resist film is further baked (PEB) on a hot plate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAM), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer. It is appreciated that the resist composition of the invention is best suited for micro-patterning using such high-energy radiation as KrF and ArF excimer laser, EB, EUV (soft x-ray), x-ray, γ-ray and synchrotron radiation.

In an alternative embodiment, a negative pattern may be formed via organic solvent development using a polymer having an acid labile group (for positive resist compositions). The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, amyl acetate, butenyl acetate, isoamyl acetate, propyl formate, butyl formate, isobutyl formate, amyl formate, isoamyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, amyl lactate, isoamyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable alcohols of 3 to 10 carbon atoms include n-propyl alcohol, isopropyl alcohol, 1-butyl alcohol, 2-butyl alcohol, isobutyl alcohol, tert-butyl alcohol, 1-pentanol, 2-pentanol, 3-pentanol, tert-amyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-sec-butyl ether, di-n-pentyl ether, diisopentyl ether, di-sec-pentyl ether, di-tert-amyl ether, and di-n-hexyl ether. The solvents may be used alone or in admixture. Besides the foregoing solvents, aromatic solvents may be used, for example, toluene, xylene, ethylbenzene, isopropylbenzene, tert-butylbenzene and mesitylene. Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is at a temperature of 70 to 180° C., preferably 80 to 170° C., for a time of 10 to 300 seconds. The extra shrink agent is stripped and the hole pattern is shrunk.

Where a hole pattern is formed by negative tone development, exposure by double dipole illuminations of X- and Y-direction line patterns provides the highest contrast light. The contrast may be further increased by combining dipole illumination with s-polarized illumination.

When a halftone phase shift mask (PSM) bearing a lattice-like shifter pattern is used, a pattern of holes may be formed at the intersections between gratings of the lattice-like shifter pattern after development, as described in JP-A 2011-170316, paragraph [0097] (US 20110177462). The preferred halftone PSM bearing a lattice-like shifter pattern has a transmittance of 3 to 15%. More preferably, the PSM used is a PSM including a lattice-like first shifter having a line width equal to or less than a half pitch and a second shifter arrayed on the first shifter and consisting of lines whose on-wafer size is 2 to 30 nm thicker than the line width of the first shifter, whereby a pattern of holes is formed only where the thick shifter is arrayed. Also preferably, the PSM used is a PSM including a lattice-like first shifter having a line width equal to or less than a half pitch and a second shifter arrayed on the first shifter and consisting of dots whose on-wafer size is 2 to 100 nm thicker than the line width of the first shifter, whereby a pattern of holes is formed only where the thick shifter is arrayed.

Exposure by double dipole illuminations of X- and Y-direction lines combined with polarized illumination presents a method of forming light of the highest contrast. This method, however, has the drawback that the throughput is substantially reduced by double exposures and mask exchange therebetween. To continuously carry out two exposures while exchanging a mask, the exposure tool must be equipped with two mask stages although the existing exposure tool includes a single mask stage. Higher throughputs may be obtained by carrying out exposure of X direction lines continuously on 25 wafers in a front-opening unified pod (FOUP), exchanging the mask, and carrying out exposure continuously on the same 25 wafers, rather than exchanging a mask on every exposure of a single wafer. However, a problem arises that as the time duration until the first one of 25 wafers is exposed in the second exposure is prolonged, the environment affects the resist such that the resist after development may change its size and shape. To block the environmental impact on wafers in standby until the second exposure, it is effective that the resist film is overlaid with a protective film.

To proceed with a single mask, it is proposed in Proc. SPIE Vol. 5377, p. 255 (2004) to carry out two exposures by dipole illuminations in X and Y directions using a mask bearing a lattice-like pattern. When this method is compared with the above method using two masks, the optical contrast is somewhat reduced, but the throughput is improved by the use of a single mask. As described in the literature, the method involves forming X-direction lines in a first photoresist film by X-direction dipole illumination using a mask bearing a lattice-like pattern, insolubilizing the X-direction lines by light irradiation, coating a second photoresist film thereon, and forming Y-direction lines by Y-direction dipole illumination, thereby forming holes at the interstices between X- and Y-direction lines. Although only a single mask is needed, this method includes additional steps of insolubilizing the first photoresist pattern between the two exposures, and coating and developing the second photoresist film. Then the wafer must be removed from the exposure stage between the two exposures, giving rise to the problem of an increased alignment error. To minimize the alignment error between two exposures, two exposures must be continuously carried out without removing the wafer from the exposure stage. The addition of s-polarized illumination to dipole illumination provides a further improved contrast and is thus preferably employed. After two exposures for forming X- and Y-direction lines using a lattice-like mask are performed in an overlapping manner, negative tone development is performed whereupon a hole pattern is formed.

When it is desired to form a hole pattern via a single exposure using a lattice-like mask, a quadrupole illumination or cross-pole illumination is used. The contrast may be improved by combining it with X-Y polarized illumination or azimuthally polarized illumination of circular polarization.

In the hole pattern forming process using the resist composition of the invention, when two exposures are involved, these exposures are carried out by changing the illumination and mask for the second exposure from those for the first exposure, whereby a fine size pattern can be formed at the highest contrast and to dimensional uniformity. The masks used in the first and second exposures bear first and second patterns of intersecting lines whereby a pattern of holes at intersections of lines is formed in the resist film after development. The first and second lines are preferably at right angles although an angle of intersection other than 90° may be employed. The first and second lines may have the same or different size and/or pitch. If a single mask bearing first lines in one area and second lines in a different area is used, it is possible to perform first and second exposures continuously. In this case, however, the maximum area available for exposure is one half. Notably, the continuous exposures lead to a minimized alignment error. Of course, the single exposure provides a smaller alignment error than the two continuous exposures.

When two exposures are performed using a single mask without reducing the exposure area, the mask pattern may be a lattice-like pattern, a dot pattern, or a combination of a dot pattern and a lattice-like pattern. The use of a lattice-like pattern contributes to the most improved light contrast, but has the drawback of a reduced resist sensitivity due to a lowering of light intensity. On the other hand, the use of a dot pattern suffers a lowering of light contrast, but provides the merit of an improved resist sensitivity.

Where holes are arrayed in horizontal and vertical directions, the above-described illumination and mask pattern are used. Where holes are arrayed at a different angle, for example, at an angle of 45°, a mask of a 45° arrayed pattern is combined with dipole illumination or cross-pole illumination.

Where two exposures are performed, a first exposure by a combination of dipole illumination with polarized illumination for enhancing the contrast of X-direction lines is followed by a second exposure by a combination of dipole illumination with polarized illumination for enhancing the contrast of Y-direction lines. Two continuous exposures with the X- and Y-direction contrasts emphasized through a single mask can be performed on a currently commercially available scanner.

The method of combining X and Y polarized illuminations with cross-pole illumination using a mask bearing a lattice-like pattern can form a hole pattern through a single exposure, despite a slight lowering of light contrast as compared with two exposures of dipole illumination. The method is estimated to attain a substantial improvement in throughput and avoids the problem of misalignment between two exposures. Using such a mask and illumination, a hole pattern of the order of 40 nm can be formed at a practically acceptable cost.

On use of a mask bearing a lattice-like pattern, light is fully shielded at intersections between gratings. A fine hole pattern may be formed by performing exposure through a mask bearing such a pattern and organic solvent development entailing positive/negative reversal.

On use of a mask bearing a dot pattern, although the contrast of an optical image is low as compared with the lattice-like pattern mask, the formation of a hole pattern is possible owing to the presence of black or light shielded spots.

It is difficult to form a fine hole pattern that holes are randomly arrayed at varying pitch and position. The super-resolution technology using off-axis illumination (such as dipole or cross-pole illumination) in combination with a phase shift mask and polarization is successful in improving the contrast of dense (or grouped) patterns, but not so the contrast of isolated patterns.

When the super-resolution technology is applied to repeating dense patterns, the pattern density bias between dense and isolated patterns, known as proximity bias, becomes a problem. As the super-resolution technology used becomes stronger, the resolution of a dense pattern is more improved, but the resolution of an isolated pattern remains unchanged. Then the proximity bias is exaggerated. In particular, an increase of proximity bias in a hole pattern resulting from further miniaturization poses a serious problem. One common approach taken to suppress the proximity bias is by biasing the size of a mask pattern. Since the proximity bias varies with properties of a photoresist composition, specifically dissolution contrast and acid diffusion, the proximity bias of a mask varies with the type of photoresist composition. For a particular type of photoresist composition, a mask having a different proximity bias must be used. This adds to the burden of mask manufacturing.

Then the pack and unpack (PAU) method is proposed in Proc. SPIE Vol. 5753, p171 (2005), which involves strong super-resolution illumination of a first positive resist to resolve a dense hole pattern, coating the first positive resist pattern with a negative resist film material in alcohol solvent which does not dissolve the first positive resist pattern, exposure and development of an unnecessary hole portion to close the corresponding holes, thereby forming both a dense pattern and an isolated pattern. One problem of the PAU method is misalignment between first and second exposures, as the authors point out in the report. The hole pattern which is not closed by the second development experiences two developments and thus undergoes a size change, which is another problem.

To form a random pitch hole pattern by organic solvent development entailing positive/negative reversal, a mask is used in which a lattice-like pattern is arrayed over the entire surface and the width of gratings is thickened only where holes are to be formed as described in JP-A 2011-170316, paragraph [0102]. Also useful is a mask in which a lattice-like pattern is arrayed over the entire surface and thick dots are disposed only where holes are to be formed. On use of a mask bearing no lattice-like pattern arrayed, holes are difficult to form, or even if holes are formed, a variation of mask size is largely reflected by a variation of hole size because the optical image has a low contrast.

EXAMPLE

Examples of the invention are given below by way of illustration and not by way of limitation. The abbreviation "pbw" is parts by weight. For all polymers, Mw and Mn are determined by GPC versus polystyrene standards using tetrahydrofuran solvent, and dispersity Mw/Mn is computed therefrom. For measurement of the size of pattern features, a scanning electron microscope (CD-SEM) CG-4000 (Hitachi High-Technologies Corp.) was used.

Synthesis Examples 1-1 to 1-6

Synthesis of Protected Amine Compounds 1 to 6

Protected Amine Compound 1 was synthesized by reacting dehydrocholic acid chloride with 1-(tert-butoxycarbonyl)-4-hydroxypiperidine in a standard way.

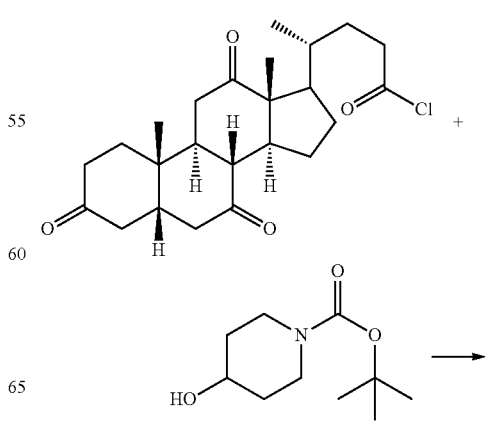

Protected Amine Compound 5

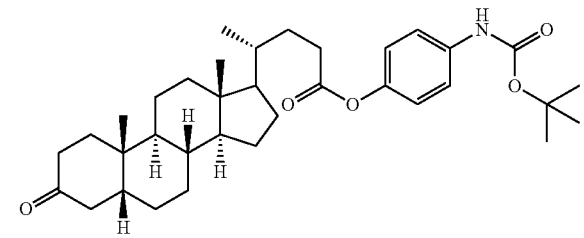

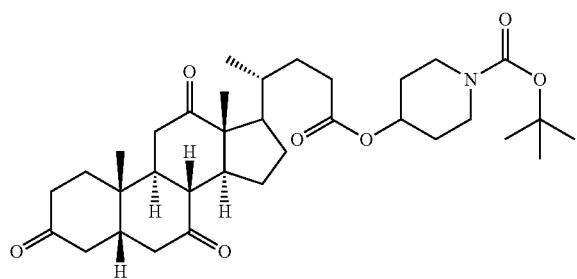

Protected Amine Compound 1

Protected Amine Compound 6

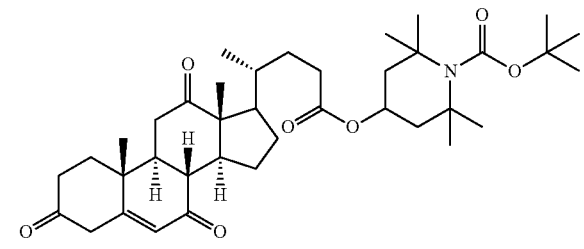

Protected Amine Compounds 2 to 6 were similarly synthesized.

Protected Amine Compounds 1 to 6 have the following structure and are ready for use in resist compositions.

Protected Amine Compound 1

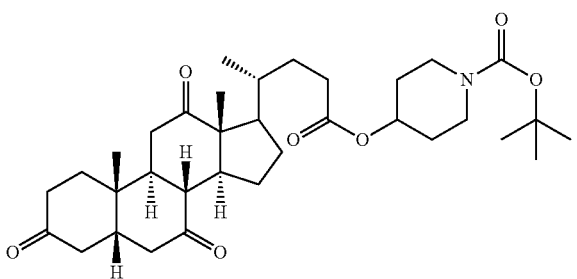

Synthesis Examples 2-1 to 2-11

Synthesis of Polymers 1 to 11

Polymers to be added to resist compositions were prepared by combining suitable monomers, effecting copolymerization reaction thereof in tetrahydrofuran solvent, pouring the reaction solution into methanol for crystallization, repeatedly washing with hexane, isolation, and drying. The resulting polymers, designated Polymers 1 to 11, were analyzed for composition by $^1$H-NMR, and for Mw and Mw/Mn by GPC.

Protected Amine Compound 2

Polymer 1

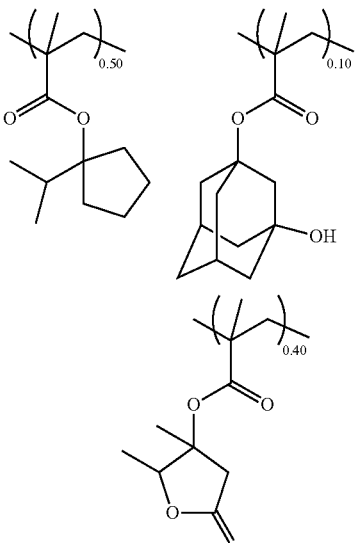

Protected Amine Compound 3

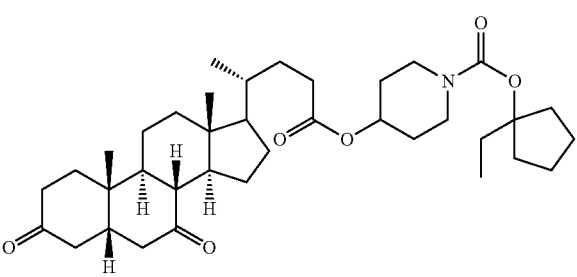

Protected Amine Compound 4

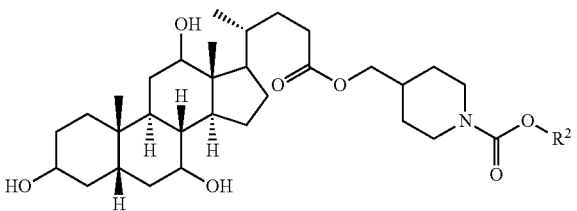

Mw = 9,600
Mw/Mn = 1.63

Polymer 2
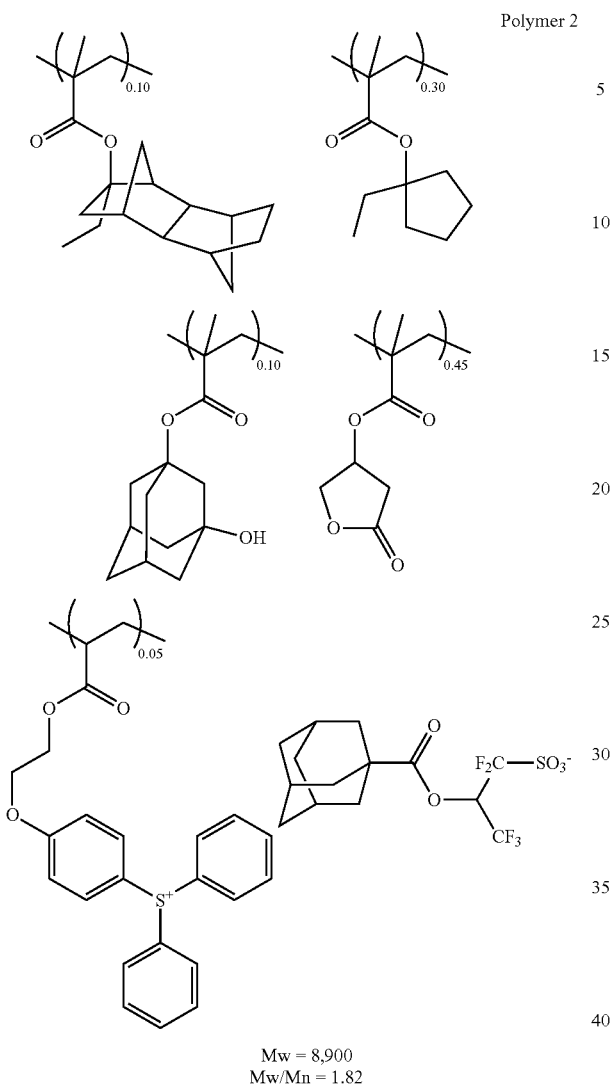
Mw = 8,900
Mw/Mn = 1.82
Polymer 3
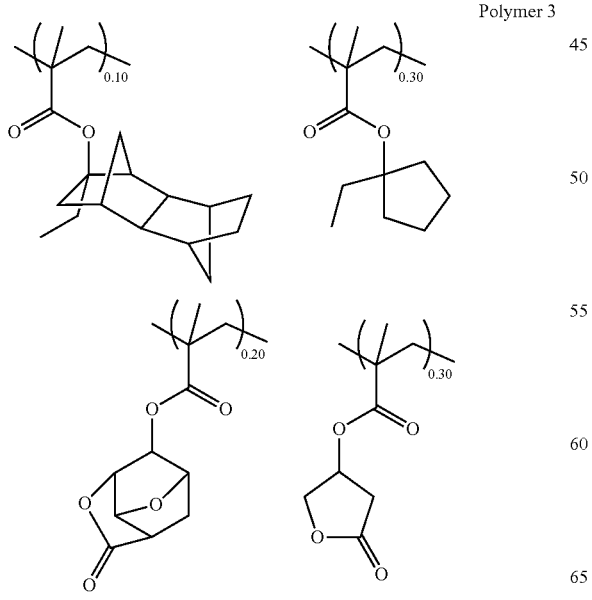
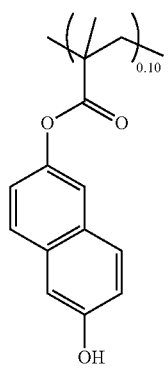
Mw = 7,500
Mw/Mn = 1.61
Polymer 4
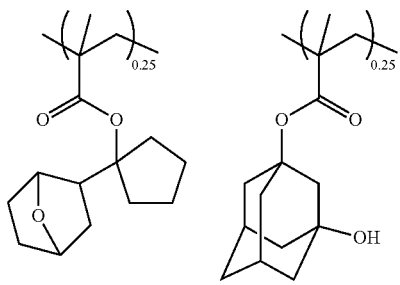
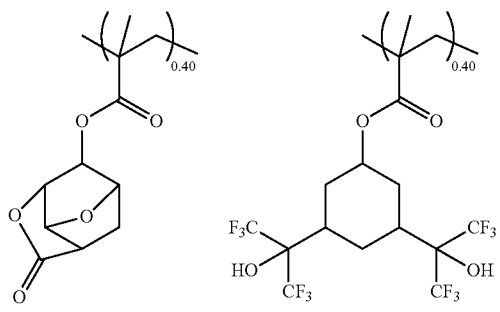
Mw = 8,900
Mw/Mn = 1.72
Polymer 5
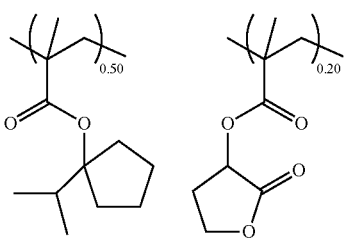

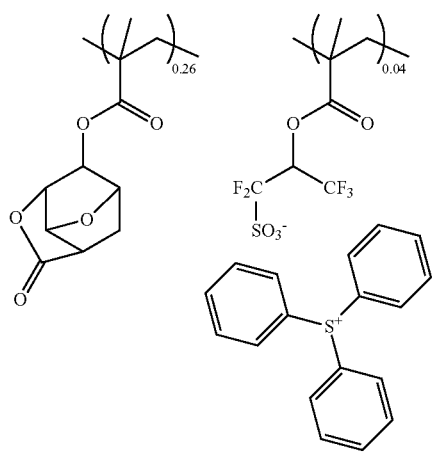
Mw = 7,800
Mw/Mn = 1.98
Polymer 6
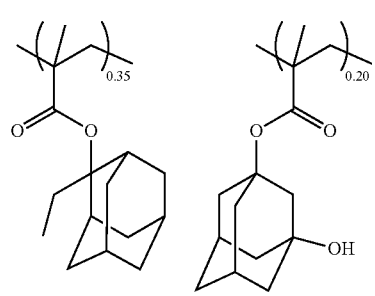
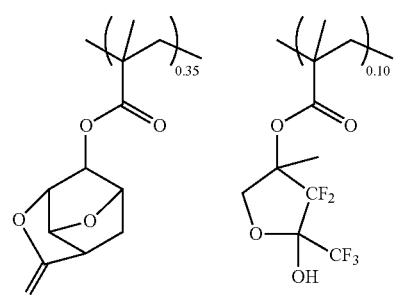
Mw = 8,500
Mw/Mn = 1.78
Polymer 7
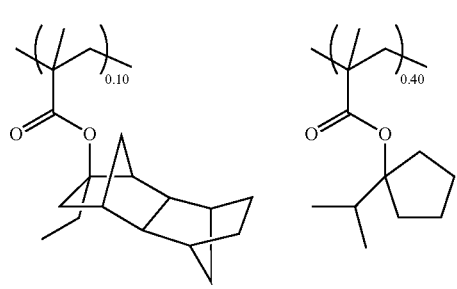
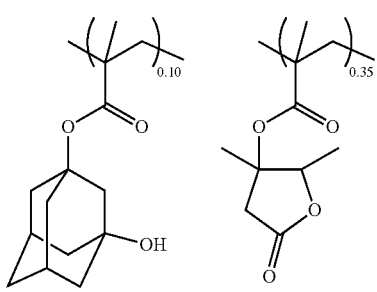
Mw = 7,900
Mw/Mn = 1.69
Polymer 8
Mw = 11,300
Mw/Mn = 1.89
Polymer 9
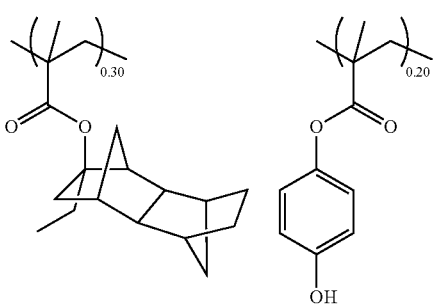

-continued

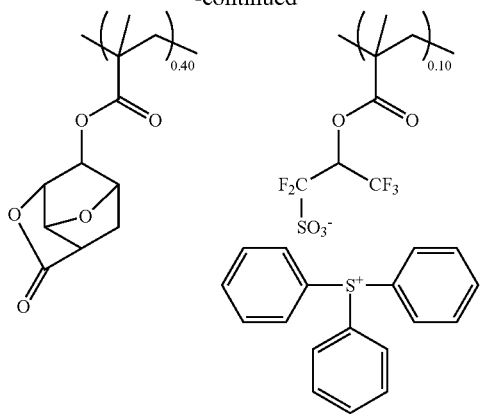

Mw = 7,600
Mw/Mn = 1.73

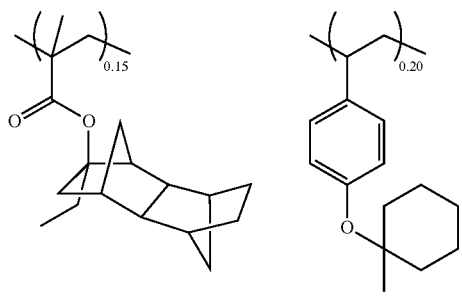

Polymer 10

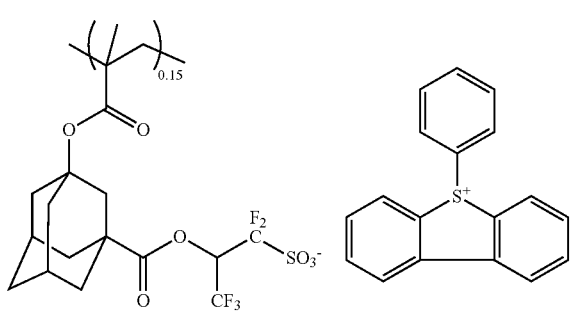

Mw = 8,500
Mw/Mn = 1.79

-continued

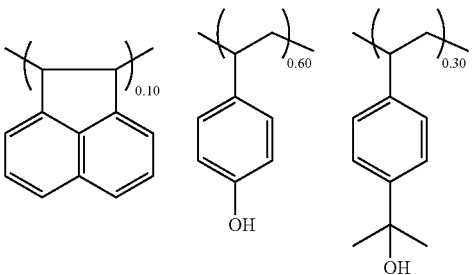

Polymer 11

Mw = 4,900
Mw/Mn = 1.78

Examples and Comparative Examples

Positive or negative resist compositions were prepared by dissolving each of the polymers synthesized above and selected components in a solvent in accordance with the recipe shown in Tables 1 to 3, and filtering through a filter having a pore size of 0.2 μm. The solvent contained 100 ppm of a surfactant FC-4430 (3M-Sumitomo Co., Ltd.). The components in Tables 1 to 3 are as identified below.

Polymers: Polymers 1 to 11 as Identified Above

Organic Solvents:
 propylene glycol monomethyl ether acetate (PGMEA)
 propylene glycol monoethyl ether (PGEE)
 propylene glycol monomethyl ether (PGME)
 cyclohexanone (CyH)
 cyclopentanone (CyP)

Acid Generators: PAG1 and PAG2

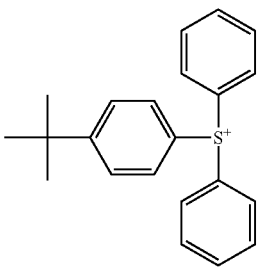

PAG 1

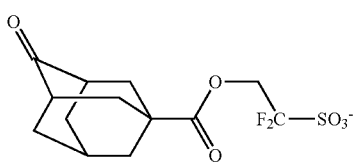

PAG 2

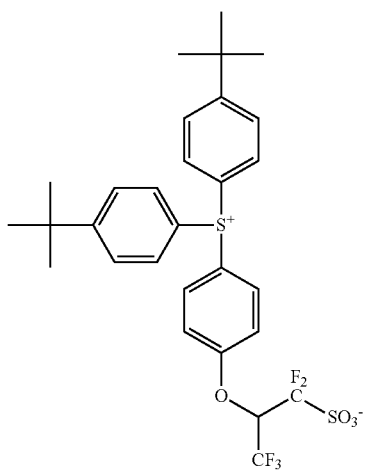

Comparative Ammonium Salt 1

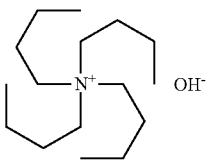

Comparative Ammonium Salt 2

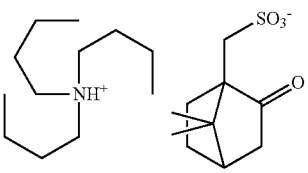

Basic Compounds:

Protected Amine Compounds 1 to 6 as Identified Above

Comparative Amine 1, Comparative Protected Amines 1, 2, Comparative Sulfonium Salt 1 and Comparative Ammonium Salts 1, 2 as Identified Below Water-Repellent Polymer:

Water-repellent polymer 1

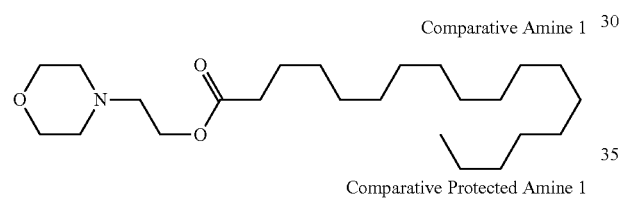

Mw = 8,900
Mw/Mn = 1.96

Comparative Amine 1

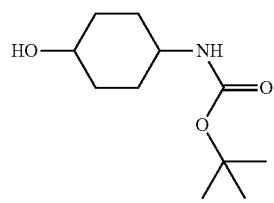

Comparative Protected Amine 1

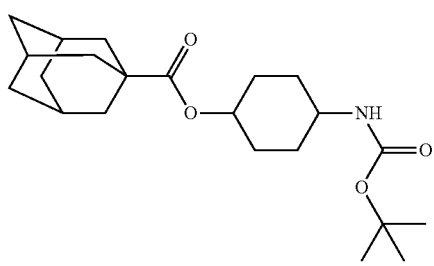

Comparative Protected Amine 2

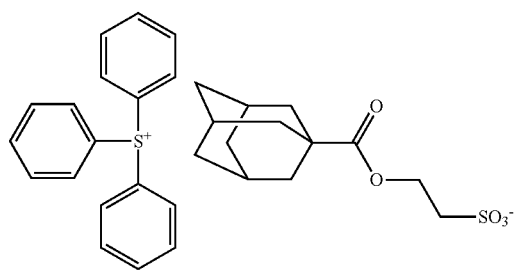

Comparative Sulfonium Salt 1

ArF Immersion Lithography Patterning Test 1

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions in Table 1 was spin coated, then baked on a hot plate at 100° C. for 60 seconds to form a resist film of 80 nm thick.

Using an ArF excimer laser immersion lithography scanner NSR-S610C (Nikon Corp., NA 1.30, σ 0.98/0.78, 35° dipole illumination, azimuthally polarized illumination), the resist film was exposed through a 6% halftone phase shift mask bearing a 40-nm line-and-space pattern (on-wafer size) in a varying exposure dose. The resist film was baked (PEB) at the temperature shown in Table 1 for 60 seconds and then developed for 30 seconds with a 2.38 wt % TMAH aqueous solution, yielding a positive line-and-space pattern.

Sensitivity was the exposure dose at which a 40-nm line-and-space pattern was formed. Using CD-SEM, the pattern was measured for roughness (LWR). The results are shown in Table 1.

TABLE 1

| | | Polymer (pbw) | Acid generator (pbw) | Basic compound (pbw) | Water-repellent polymer (pbw) | Organic solvent (pbw) | PEB temp. (° C.) | Sensitivity (mJ/cm$^2$) | LWR (nm) |
|---|---|---|---|---|---|---|---|---|---|
| Example | 1-1 | Polymer 1 (100) | PAG1 (10.0) | Protected Amine Compound 1 (4.00) | Water-repellent polymer 1 (4.0) | PGMEA(2,200) GBL(300) | 90 | 32 | 2.1 |
| | 1-2 | Polymer 1 (100) | PAG1 (10.0) | Protected Amine Compound 2 (4.00) | Water-repellent polymer 1 (4.0) | PGMEA(2,200) GBL(300) | 90 | 34 | 2.3 |
| | 1-3 | Polymer 1 (100) | PAG1 (10.0) | Protected Amine Compound 3 (4.00) | Water-repellent polymer 1 (4.0) | PGMEA(2,200) GBL(300) | 90 | 38 | 2.5 |
| | 1-4 | Polymer 1 (100) | PAG1 (10.0) | Protected Amine Compound 4 (4.00) | Water-repellent polymer 1 (4.0) | PGMEA(2,200) GBL(300) | 90 | 38 | 2.8 |
| | 1-5 | Polymer 1 (100) | PAG1 (10.0) | Protected Amine Compound 5 (4.00) | Water-repellent polymer 1 (4.0) | PGMEA(2,200) GBL(300) | 90 | 33 | 2.9 |
| | 1-6 | Polymer 1 (100) | PAG1 (10.0) | Protected Amine Compound 6 (4.00) | Water-repellent polymer 1 (4.0) | PGMEA(2,200) GBL(300) | 90 | 31 | 2.7 |
| | 1-7 | Polymer 2 (100) | — | Protected Amine Compound 6 (4.00) | Water-repellent polymer 1 (4.0) | PGMEA(2,200) GBL(300) | 95 | 35 | 2.2 |
| | 1-8 | Polymer 3 (100) | PAG1 (10.0) | Protected Amine Compound 6 (4.00) | Water-repellent polymer 1 (4.0) | PGMEA(2,200) GBL(300) | 95 | 36 | 2.2 |
| | 1-9 | Polymer 4 (100) | PAG1 (10.0) | Protected Amine Compound 6 (4.00) | Water-repellent polymer 1 (4.0) | PGMEA(2,200) GBL(300) | 95 | 37 | 3.0 |
| | 1-10 | Polymer 5 (100) | — | Protected Amine Compound 6 (4.00) | Water-repellent polymer 1 (4.0) | PGMEA(2,200) GBL(300) | 90 | 45 | 2.8 |
| | 1-11 | Polymer 6 (100) | PAG2 (14.0) | Protected Amine Compound 6 (4.00) | Water-repellent polymer 1 (4.0) | PGMEA(2,200) GBL(300) | 95 | 39 | 2.9 |
| | 1-12 | Polymer 7 (100) | PAG2 (14.0) | Protected Amine Compound 6 (4.00) | Water-repellent polymer 1 (4.0) | PGMEA(2,200) GBL(300) | 90 | 33 | 3.0 |
| | 1-13 | Polymer 8 (100) | PAG2 (14.0) | Protected Amine Compound 6 (4.00) | Water-repellent polymer 1 (4.0) | PGMEA(2,200) GBL(300) | 85 | 39 | 2.4 |
| Comparative Example | 1-1 | Polymer 1 (100) | PAG1 (10.0) | Comparative Amine 1 (2.20) | Water-repellent polymer 1 (4.0) | PGMEA(2,200) GBL(300) | 90 | 32 | 4.3 |
| | 1-2 | Polymer 1 (100) | PAG1 (10.0) | Comparative Protected Amine 1 (2.20) | Water-repellent polymer 1 (4.0) | PGMEA(2,200) GBL(300) | 90 | 30 | 4.8 |
| | 1-3 | Polymer 1 (100) | PAG1 (10.0) | Comparative Protected Amine 2 (2.20) | Water-repellent polymer 1 (4.0) | PGMEA(2,200) GBL(300) | 90 | 36 | 4.1 |
| | 1-4 | Polymer 1 (100) | PAG1 (10.0) | Comparative Sulfonium Salt 1 (3.50) | Water-repellent polymer 1 (4.0) | PGMEA(2,200) GBL(300) | 90 | 26 | 3.6 |
| | 1-5 | Polymer 1 (100) | PAG1 (10.0) | Comparative Ammonium Salt 1 (1.90) | Water-repellent polymer 1 (4.0) | PGMEA(2,200) GBL(300) | 90 | 27 | 3.7 |
| | 1-6 | Polymer 1 (100) | PAG1 (10.0) | Comparative Ammonium Salt 2 (2.10) | Water-repellent polymer 1 (4.0) | PGMEA(2,200) GBL(300) | 90 | 26 | 3.8 |

ArF Immersion Lithography Patterning Test 2

On a substrate (silicon wafer), a spin-on carbon film ODL-50 (Shin-Etsu Chemical Co., Ltd.) having a carbon content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, the resist composition shown in Table 2 was spin coated, then baked on a hot plate at 100° C. for 60 seconds to form a resist film of 80 nm thick.

Using an ArF excimer laser immersion lithography scanner NSR-610C (Nikon Corp., NA 1.30, σ 0.98/0.78, 35° cross-pole illumination, azimuthally polarized illumination), exposure was performed in a varying dose through a 6% halftone phase shift mask bearing a lattice-like pattern of dots with a one side size of 55 nm arranged at a pitch of 100 nm (on-wafer size). After the exposure, the wafer was baked (PEB) at the temperature shown in Table 2 for 60 seconds and developed in n-butyl acetate for 30 seconds. Subsequent spin drying yielded a negative hole pattern having a diameter of 45 nm.

Sensitivity was the exposure dose at which a 45-nm hole pattern was formed. Using CD-SEM, the diameter of 20 holes was measured, from which CDU was computed as size variation. The results are shown in Table 2.

TABLE 2

| | | Polymer (pbw) | Acid generator (pbw) | Basic compound (pbw) | Water-repellent polymer (pbw) | Organic solvent (pbw) | PEB temp. (° C.) | Sensitivity (mJ/cm$^2$) | CDU (nm) |
|---|---|---|---|---|---|---|---|---|---|
| Example | 2-1 | Polymer 8 (100) | PAG2 (10.0) | Protected Amine Compound 1 (2.93) | Water-repellent polymer 1 (4.0) | PGMEA(2,000) GBL(400) | 90 | 52 | 2.8 |
| | 2-2 | Polymer 8 (100) | PAG2 (10.0) | Protected Amine Compound 2 (2.93) | Water-repellent polymer 1 (4.0) | PGMEA(2,000) GBL(400) | 90 | 51 | 2.6 |
| Comparative Example | 2-1 | Polymer 8 (100) | PAG2 (10.0) | Comparative Amine 1 (2.93) | Water-repellent polymer 1 (4.0) | PGMEA(2,000) GBL(400) | 90 | 57 | 4.5 |
| | 2-2 | Polymer 8 (100) | PAG2 (10.0) | Comparative Protected Amine 1 (2.93) | Water-repellent polymer 1 (4.0) | PGMEA(2,000) GBL(400) | 90 | 48 | 4.9 |
| | 2-3 | Polymer 8 (100) | PAG2 (10.0) | Comparative Protected Amine 2 (2.93) | Water-repellent polymer 1 (4.0) | PGMEA(2,000) GBL(400) | 90 | 50 | 4.4 |
| | 2-4 | Polymer 8 (100) | PAG2 (10.0) | Comparative Sulfonium Salt 1 (2.93) | Water-repellent polymer 1 (4.0) | PGMEA(2,000) GBL(400) | 90 | 48 | 3.6 |
| | 2-5 | Polymer 8 (100) | PAG2 (10.0) | Comparative Ammonium Salt 1 (2.93) | Water-repellent polymer 1 (4.0) | PGMEA(2,000) GBL(400) | 90 | 46 | 3.8 |
| | 2-6 | Polymer 8 (100) | PAG2 (10.0) | Comparative Ammonium Salt 2 (2.93) | Water-repellent polymer 1 (4.0) | PGMEA(2,000) GBL(400) | 90 | 44 | 3.8 |

EB Writing Test

Each of the resist compositions in Table 3 was spin coated onto a silicon substrate, which had been vapor primed with hexamethyldisilazane (HMDS), and pre-baked on a hot plate at 110° C. for 60 seconds to form a resist film of 80 nm thick. Using a system HL-800D (Hitachi Ltd.) at a HV voltage of 50 keV, the resist film was exposed imagewise to EB in a vacuum chamber.

Immediately after the image writing, the resist film was baked (PEB) on a hot plate at 90° C. for 60 seconds and developed in a 2.38 wt % TMAH aqueous solution for 30 seconds to form a pattern.

In the case of positive resist film, the resolution is a minimum trench size at the exposure dose that provides a resolution as designed of a 120-nm trench pattern. In the case of negative resist film, the resolution is a minimum isolated line size at the exposure dose that provides a resolution as designed of a 120-nm isolated line pattern. It is noted that Examples 3-1, 3-2 and Comparative Example 3-1 are positive resist compositions, and Example 3-3 and Comparative Example 3-2 are negative resist compositions. The results are shown in Table 3.

TABLE 3

| | | Polymer (pbw) | Acid generator (pbw) | Basic compound (pbw) | Organic solvent (pbw) | PEB temp. (° C.) | Sensitivity (μC/cm$^2$) | Resolution (nm) |
|---|---|---|---|---|---|---|---|---|
| Example | 3-1 | Polymer 9 (100) | — | Protected Amine Compound 1 (2.10) | PGMEA(2,000) GBL(200) PGME(300) | 90 | 32 | 80 |
| | 3-2 | Polymer 10 (100) | — | Protected Amine Compound 1 (2.10) | PGMEA(400) CyH(1,600) CyP(500) | 75 | 52 | 70 |
| | 3-3 | Polymer 11 (100) | PAG1 (15.0) | Protected Amine Compound 1 (2.10) | PGMEA(2,000) GBL(200) PGME(300) | 90 | 44 | 70 |
| Comparative Example | 3-1 | Polymer 9 (100) | — | Comparative Amine 1 (1.20) | PGMEA(400) CyH(2,000) PGME(100) | 90 | 38 | 90 |
| | 3-2 | Polymer 11 (100) | PAG1 (15.0) | Comparative Amine 1 (1.20) | PGMEA(2,000) GBL(200) PGME(300) | 90 | 45 | 90 |

It is demonstrated in Tables 1 to 3 that resist compositions comprising specific protected amine compounds form patterns of satisfactory profile having an improved resolution and minimal LWR.

Japanese Patent Application No. 2014-237527 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A chemically amplified resist composition comprising a base polymer, an acid generator, and a basic compound having the general formula (1)-1 and/or (1)-2:

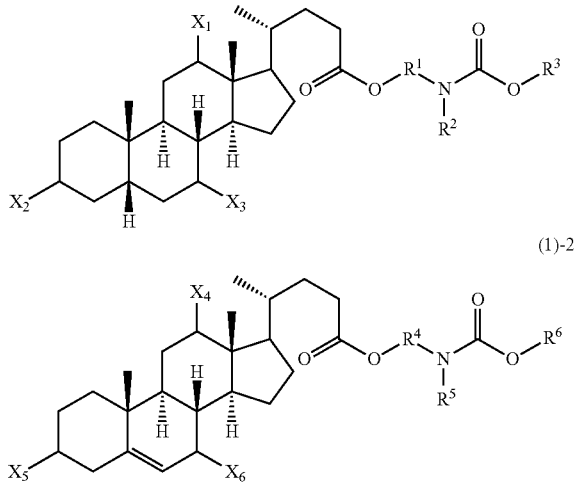

wherein $R^1$ and $R^4$ each are a single bond, a straight, branched or cyclic $C_1$-$C_{20}$ alkylene, $C_6$-$C_{10}$ arylene, $C_2$-$C_{20}$ alkenylene, or $C_2$-$C_{20}$ alkynylene group, $R^2$ and $R^5$ each are hydrogen or a straight, branched or cyclic $C_1$-$C_{12}$ alkyl group, or $R^2$ may bond with $R^1$ to form a ring, and $R^5$ may bond with $R^4$ to form a ring, $R^3$ and $R^6$ each are an acid labile group, $X_1$ to $X_6$ each are hydrogen, hydroxyl, alkoxy, acyloxy' or carbonyl group.

2. The resist composition of claim 1, further comprising an organic solvent, the composition being a chemically amplified positive resist composition.

3. The resist composition of claim 2, further comprising a dissolution inhibitor.

4. The resist composition of claim 1, further comprising an organic solvent, the composition being a chemically amplified negative resist composition.

5. The resist composition of claim 4, further comprising a crosslinker.

6. The resist composition of claim 1, further comprising a surfactant.

7. A process for forming a pattern comprising the steps of applying the resist composition of claim 1 onto a substrate, baking to form a resist film, exposing the resist film to high-energy radiation, and developing the exposed film with a developer.

8. The process of claim 7 wherein the high-energy radiation is ArF excimer laser radiation of wavelength 193 nm or KrF excimer laser radiation of wavelength 248 nm.

9. The process of claim 7 wherein the high-energy radiation is electron beam or extreme ultraviolet radiation of wavelength 3 to 15 nm.

* * * * *